(12) United States Patent
Oliver et al.

(10) Patent No.: US 12,290,618 B2
(45) Date of Patent: May 6, 2025

(54) SCENT DISPENSERS/ABSORBERS AND SCENT CARTRIDGES THEREFOR

(71) Applicant: NOVIA PRODUCTS, LLC, Limerick, ME (US)

(72) Inventors: Corey Oliver, Limington, ME (US); William Webster, Portland, ME (US); Randy Oliver, Limerick, ME (US); David Gallant, Newfield, ME (US); Denise Oliver, Limington, ME (US)

(73) Assignee: Novia Products, LLC, Limerick, ME (US)

( * ) Notice: Subject to any disclaimer, the term of this patent is extended or adjusted under 35 U.S.C. 154(b) by 0 days.

(21) Appl. No.: 18/634,727

(22) Filed: Apr. 12, 2024

(65) Prior Publication Data
US 2024/0269335 A1 Aug. 15, 2024

Related U.S. Application Data

(63) Continuation-in-part of application No. 17/991,612, filed on Nov. 21, 2022, which is a
(Continued)

(51) Int. Cl.
*A61L 9/12* (2006.01)
*A61L 9/012* (2006.01)

(52) U.S. Cl.
CPC ............... *A61L 9/12* (2013.01); *A61L 9/012* (2013.01); *A61L 2209/12* (2013.01); *A61L 2209/133* (2013.01)

(58) Field of Classification Search
None
See application file for complete search history.

(56) References Cited

U.S. PATENT DOCUMENTS

| 1,481,325 A | 1/1924 | Le Gris |
| 3,134,544 A | 5/1964 | Copley |

(Continued)

FOREIGN PATENT DOCUMENTS

| EP | 0335669 B1 | 6/1993 |
| EP | 0691113 B1 | 1/1996 |

OTHER PUBLICATIONS

International Search Report for PCT/US2021/33740 entitled "Scent Dispensers/Absorbers and Scent Cartridges Therefor," mailed on Oct. 1, 2021 (4 pages).
(Continued)

*Primary Examiner* — Jelitza M Perez
(74) *Attorney, Agent, or Firm* — Clark Hill PLC

(57) ABSTRACT

A scent dispenser/absorber includes a container, an invertible lid reversibly attached to an open end of the container, a vented cage, and a scent cartridge housed within the cage. In an "off" condition or state, the scent cartridge/cage combination is received in an interior chamber of the container, where the scent cartridge is out of communication with the surrounding environment and therefore incapable of performing scent dispensing or absorbing functions. The scent dispenser/absorber can be switched to an "on" condition or state by manually inverting the lid and, in some cases, the associated cage/scent cartridge combination, such that the scent cartridge can be positioned externally of the container, where it can communicate with the surrounding environment to perform a desired scent dispensing or absorbing function. In an "on" condition, scent molecules originating from an odorant contained in the scent cartridge are diffused into the surrounding environment.

111 Claims, 27 Drawing Sheets

Related U.S. Application Data continuation-in-part of application No. PCT/US2021/033740, filed on May 21, 2021.

(60) Provisional application No. 63/459,156, filed on Apr. 13, 2023, provisional application No. 63/132,303, filed on Dec. 30, 2020, provisional application No. 63/091,786, filed on Oct. 14, 2020, provisional application No. 63/028,433, filed on May 21, 2020.

(56) References Cited

U.S. PATENT DOCUMENTS

| | | | |
|---|---|---|---|
| D250,801 S | 1/1979 | Bergen et al. | |
| 4,137,200 A | 1/1979 | Wood et al. | |
| 4,374,571 A * | 2/1983 | Hirvela | A61L 9/12 239/57 |
| 4,601,403 A | 7/1986 | Pollitz | |
| 4,957,810 A | 9/1990 | Eleouet et al. | |
| 5,064,653 A | 11/1991 | Sessions et al. | |
| D351,650 S | 10/1994 | Vavra | |
| 5,388,762 A | 2/1995 | Bryson, Sr. | |
| D372,770 S | 8/1996 | Foreman | |
| 5,610,674 A | 3/1997 | Martin | |
| 5,611,165 A | 3/1997 | Blaha et al. | |
| D387,734 S | 12/1997 | Hawkins, Jr. et al. | |
| 5,837,377 A | 11/1998 | Sheu et al. | |
| 5,880,216 A | 3/1999 | Tanihara et al. | |
| 5,898,475 A | 4/1999 | Martin | |
| 5,973,221 A | 10/1999 | Collyer et al. | |
| D422,481 S | 4/2000 | Bertani | |
| 6,277,401 B1 | 8/2001 | Bello et al. | |
| 6,617,014 B1 | 9/2003 | Thomson | |
| D493,875 S | 8/2004 | Groene et al. | |
| 6,889,870 B2 | 5/2005 | De Laforcade | |
| 6,991,848 B2 | 1/2006 | Thomson | |
| 6,997,355 B2 | 2/2006 | Duquet et al. | |
| 7,048,966 B2 | 5/2006 | Thomson | |
| D550,840 S | 9/2007 | Anderson et al. | |
| D568,715 S | 5/2008 | Gustafson et al. | |
| D575,711 S | 8/2008 | Johannsen | |
| 8,251,299 B1 | 8/2012 | Irvin | |
| D676,551 S | 2/2013 | Desai et al. | |
| 8,544,766 B2 | 10/2013 | Webster et al. | |
| D710,699 S | 8/2014 | Phelps | |
| D791,426 S | 7/2017 | Petersen | |
| D794,765 S | 8/2017 | Brandenburg et al. | |
| 9,821,082 B1 | 11/2017 | Swartz et al. | |
| D830,530 S | 10/2018 | Webster et al. | |
| D849,049 S | 5/2019 | Niven et al. | |
| D910,159 S | 2/2021 | Webster et al. | |
| 10,912,855 B2 | 2/2021 | Webster et al. | |
| 11,207,439 B2 | 12/2021 | Webster et al. | |
| 2002/0018884 A1 | 2/2002 | Thomson | |
| 2002/0113909 A1 | 8/2002 | Sherwood | |
| 2004/0144811 A1 | 7/2004 | Pennaneac'h et al. | |
| 2006/0216492 A1 | 9/2006 | Thomson | |
| 2007/0187524 A1 | 8/2007 | Sherwood | |
| 2007/0224232 A1 | 9/2007 | Sherwood | |
| 2010/0059071 A1 | 3/2010 | Dorsey | |
| 2010/0314465 A1 | 12/2010 | Webster | |
| 2011/0147478 A1 | 6/2011 | Bernstein | |
| 2013/0206861 A1 | 8/2013 | Webster et al. | |
| 2013/0292484 A1 * | 11/2013 | Jackson | B05B 17/0646 239/4 |
| 2017/0312380 A1 | 11/2017 | Webster et al. | |
| 2019/0125916 A1 | 5/2019 | Webster | |

OTHER PUBLICATIONS

International Written Opinion for PCT/US2021/33740 entitled "Scent Dispensers/Absorbers and Scent Cartridges Therefor," mailed on Oct. 1, 2021 (12 pages).
www.scentair.com/products/index.php?subSectionID=2, Dated May 26, 2009.
ScentWave SWD-1000 Technical Specifications.
ScentStream SXD-5020 Technical Specifications.
ScentPop Technical Specifications.
International Preliminary Report on Patentability for PCT/US2021/33740 entitled "Scent Dispensers/Absorbers and Scent Cartridges Therefor," mailed on Nov. 17, 2022 (13 pages).
"8-in-1 Excel Calm Quil Natural Calming Charm Collar for Dogs"; Amazon.com pp. 1-3. The Wayback Machine; access on May 23, 2020; https://web.archive.org/web/20100823084008/jttps://www.amazon/Excel-Natural-Calming Charm Collar/dp/B00251C8ts (Year 2010).
U.S. Appl. No. 62/480,948, entitled "Packaging for Scented Devices," filed Apr. 3, 2017.

* cited by examiner

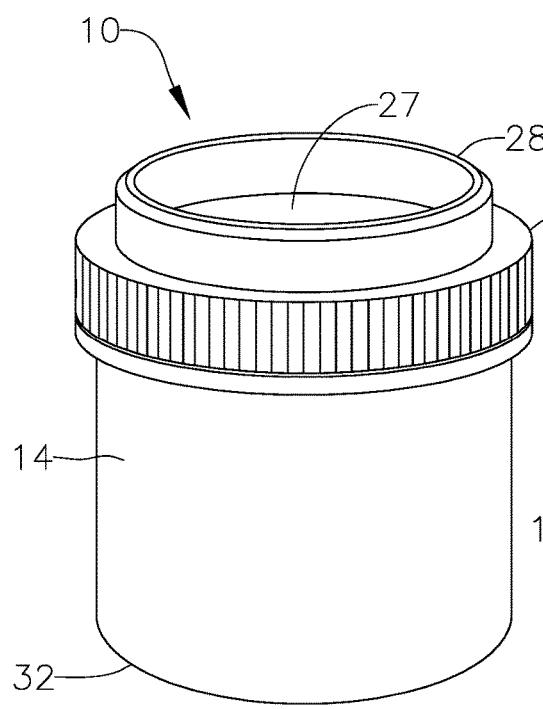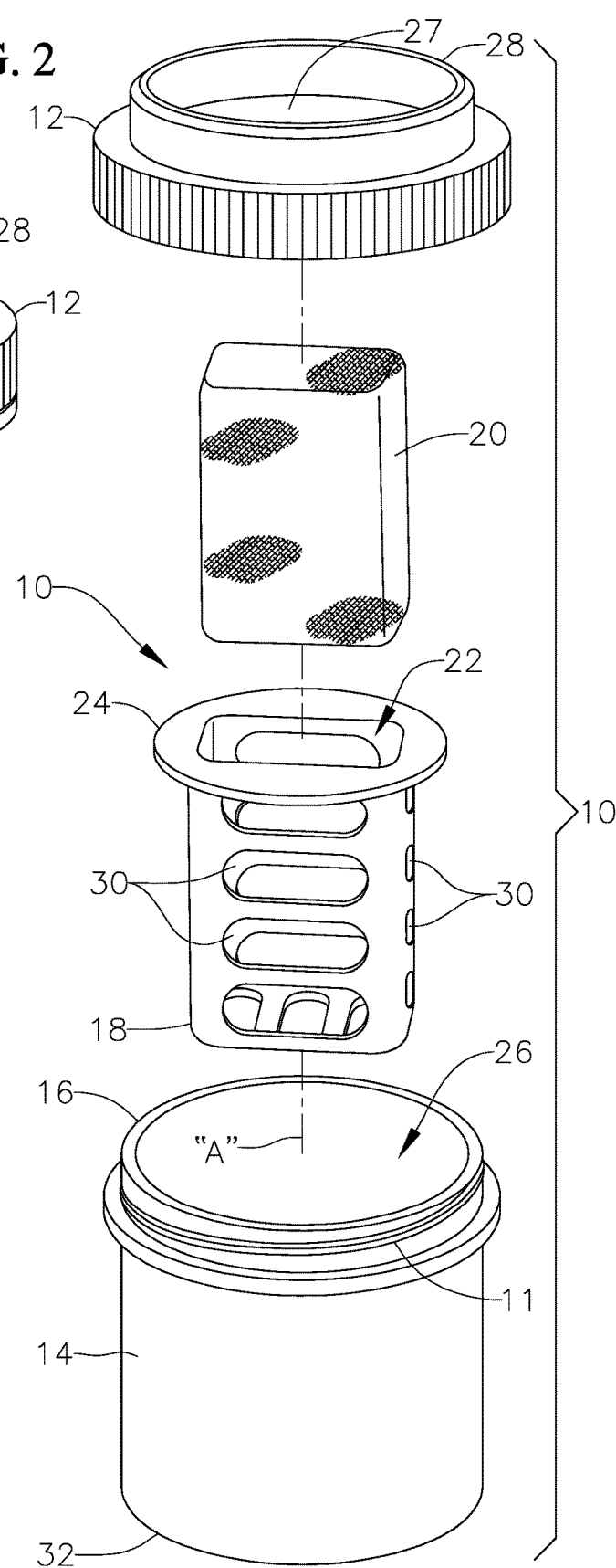

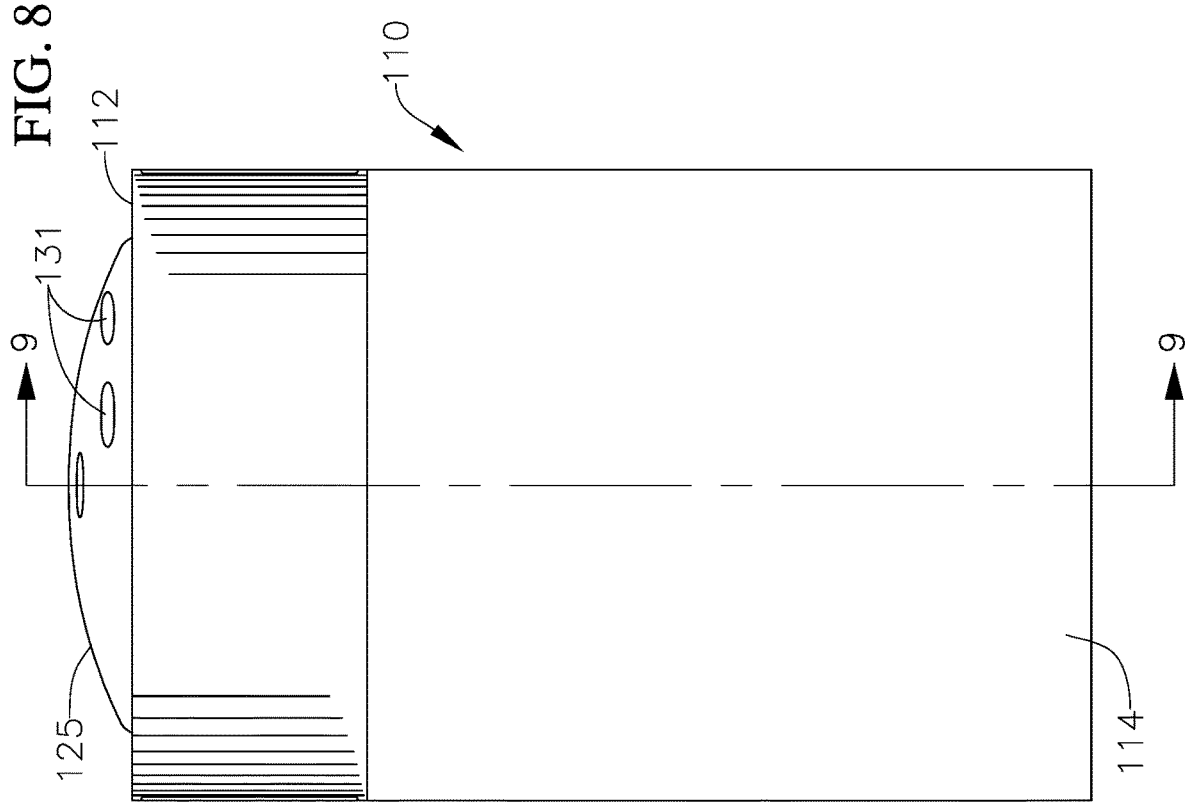
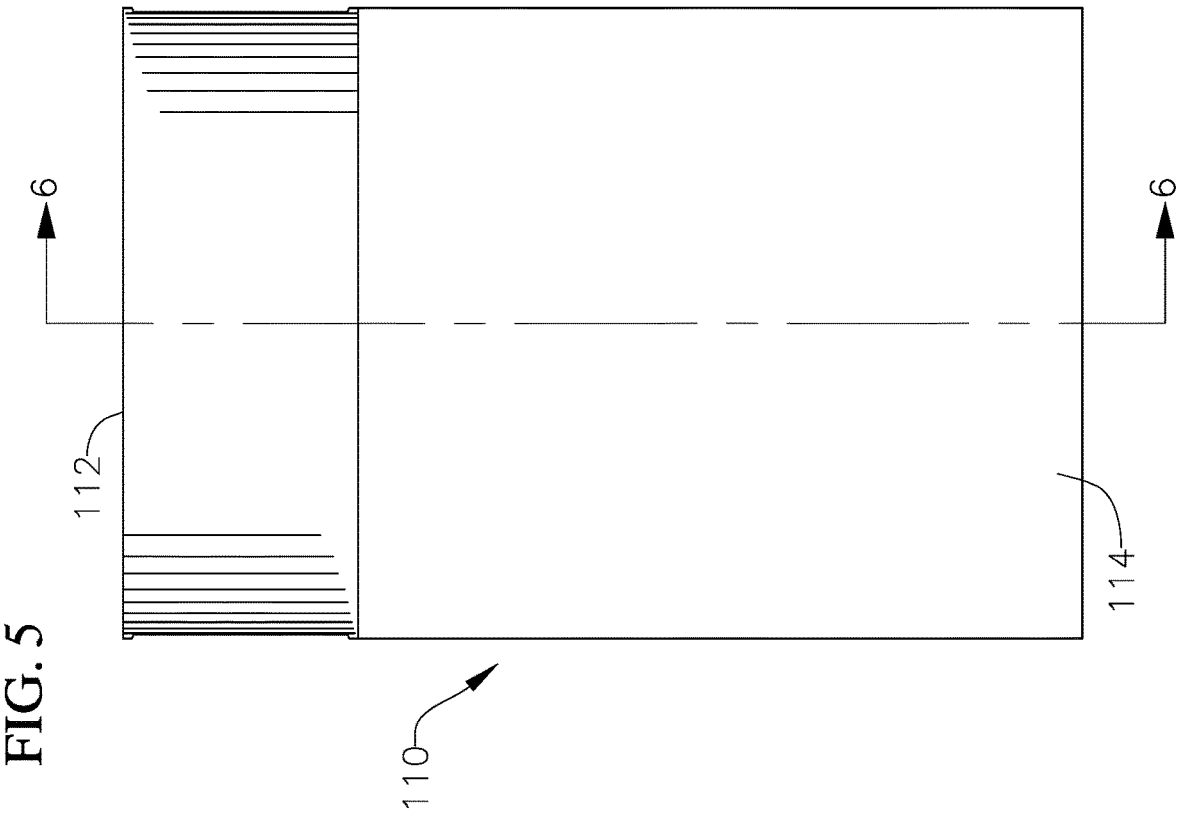

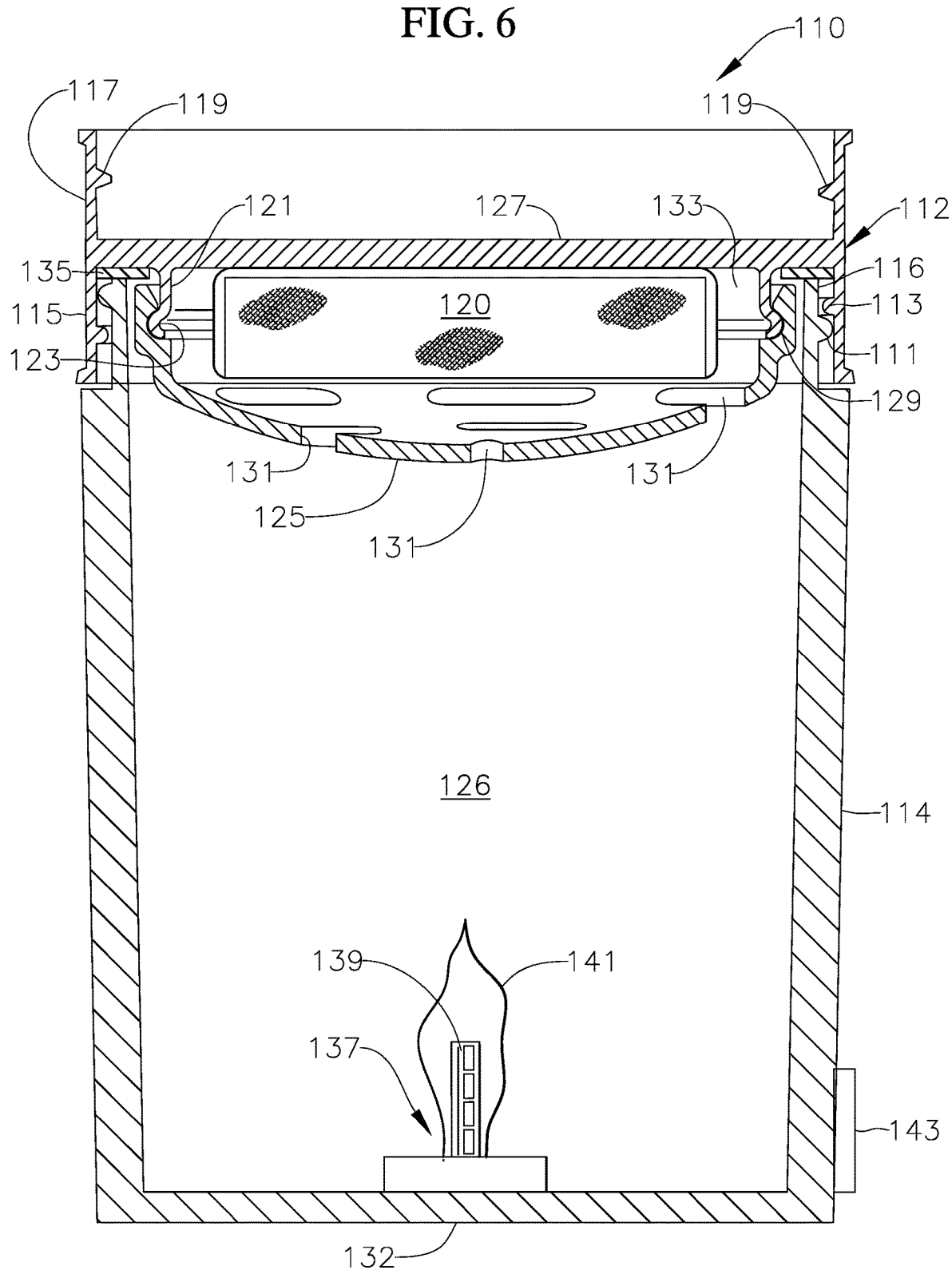

SCENT DISPENSERS/ABSORBERS AND SCENT CARTRIDGES THEREFOR

CROSS-REFERENCE TO RELATED APPLICATIONS

This application claims priority to U.S. Provisional Patent Application Ser. No. 63/459,156 filed Apr. 13, 2023 and is a continuation-in-part of U.S. non-provisional patent application Ser. No. 17/991,612 filed Nov. 21, 2022, which is a continuation-in-part of PCT Patent Application Serial No. PCT/US2021/033740 filed May 21, 2021, which claims priority to U.S. Provisional Patent Application Ser. No. 63/028,433 filed May 21, 2020, U.S. Provisional Patent Application Ser. No. 63/091,786 filed Oct. 14, 2020, and U.S. Provisional Patent Application Ser. No. 63/132,303 filed Dec. 30, 2020 and incorporates by reference the entire disclosure of each of the aforesaid applications.

FIELD OF THE INVENTION

The present invention relates to dispensers of scents into the environment and/or absorbers of odors from the environment.

BACKGROUND OF THE INVENTION

Various forms of dispensers of scents into the environment, such as household or other building interior environments, or devices for removing odors from such environments, are known in the art. Many of these dispensers and/or devices have a multi-component design requiring them to be assembled with the use of independent fasteners and/or tools.

Devices are known which carry and emit scent (typically as a vapor) to the ambient environment. In some cases, these known devices are in the form of foams, fibers, gels, or porous materials that have been loaded with scents, typically in the form of a liquid or a solid. Such scented devices are often housed in a vessel or receptacle which contains the scent-containing foams, fibers, gels, or porous materials. In use, these known devices are often designed and adapted to deliver wet air to a room or other large space.

SUMMARY OF THE INVENTION

An object of at least one embodiment of the present invention is to provide a versatile scent-dispensing/absorbing apparatus that is efficient and effective in use, while maintaining simplicity and economics of manufacture and operation.

Embodiments of the present invention have, as an additional object, the ability to dispense scents via molecules (i.e., "dry air"), free from mists, sprays, aerosols and liquid, while requiring no "active" driving mechanisms such as volatile organic compounds (i.e., VOCs), chemicals, electricity, heat, or similar propellant enablers to achieve diffusion. The ability to minimize propellants, especially moisture-based ones in accordance with this object, is advantageous in that it may mitigate the spread of contagious disease, such as the one which plagued the world during the recent COVID crisis.

Another object of embodiments of the present invention is to provide scents dedicated to different functions, such as study aid scents, holiday scents, soothing scents, teleconferencing scents, desk/work scents, wellness related scents, smell retraining therapy as a treatment protocol for anosmia and hyposmia, etc.

A further object of embodiments of the present invention is to provide for personal, portable scent diffusers that can be used anywhere and at any time.

It is yet another object of embodiments of the present invention to allow essential oils to be diffused in pure, unadulterated form without artificial propellants. In accordance with this object, embodiments of the present invention accomplish scent dispensing/absorbing functions with ambient air used as the propellant.

Another object of at least one embodiment of the present invention is to provide and enable the transfer of oil-based scents, while minimizing or eliminating a user's interaction with any liquid-state scent material.

Yet another object of at least some of the embodiments of the present invention is to ensure that the odorant scents diffused from a device are the same as those initially infused therein, thereby minimizing adulteration of the diffused scent.

It is still a further object of various embodiments of the present invention to operate free of liquids, with such embodiments utilizing scent cartridges containing a minimal amount of liquid odorants. In accordance with this object, embodiments of the present invention operate via a diffusion process free of liquid droplets or aerosols.

It is yet a further object of embodiments of the present invention to provide a device that can be easily and manually switched or toggled between "on" and "off" configurations, while also allowing for the controlled direct transmission of scent (i.e., varying the rate of diffusion/absorption).

An additional object of various embodiments of the present invention is to provide scent-absorbing or diffusing functions lasting multiple months in typical use.

It is yet another object of at least one embodiment of the present invention to provide a device that is compatible with any odorant used now or in the future.

A still further object of various embodiments of the present invention is to provide a device designed such that essential oils are dispensed in a way that avoids damage to finished surfaces or fabrics.

An additional object of various embodiments of the present invention is to allow for personal and portable scent diffusion, whereby scent can be delivered, without batteries or plug-in electricity, directly to the personal space of an individual, such as while the individual is driving a vehicle or is seated at a desk, rather than to an entire room or similar large space.

A not necessarily final object of at least one embodiment of the present invention is to provide a scent insert adapted for use with a scent dispenser and configured to control: 1) the length of effective time of scent diffusion; 2) the intensity of the diffused scent; and 3) the exponential decay curve of the diffused scent (e.g., promoting generally longer, linear curves).

In accordance with the aforementioned objects, an embodiment of the present invention relates to a novel "dry air" scent dispenser, which includes a cylindrical container, a reversible lid, a vented cage and a scent cartridge. The scent cartridge fits inside the cage, which can then be attached to one side of the lid. The lid is configured to be received by the container in two different conditions (i.e., an "off" condition and an "on" condition). In the "off" condition, the cage and scent cartridge are confined inside the container, where they do not interface with the outside air to absorb/dispense scents. To switch to the "on" condition, a user removes the lid, inverts it such that the scent cartridge and cage are outside the container and then places the lid back on the container in an inverted position. In such an "on" condition or inverted position, scents are dispensed to/absorbed from the surrounding air. When not in use, the lid can be inverted once more by a user and replaced on the container to return the device to its original position and therefore its "off" condition.

In one particular embodiment, the aforementioned insert is placed in (i.e., encased or otherwise enclosed within) a fabric form, examples of which include, but are not limited to, a pillow, cushion, pouch, sachet or similar enclosure. In use, scent molecules originating from the odorant are passively and continuously released from the insert's reticulated, hydrophilic inner core. The scent molecules released from the inner core of the insert pass through the insert's thermoplastic outer skin and then the fabric form, before being diffused into the surrounding environment to provide a faithful iteration of the original odorant or scent for sampling, fragrancing or other purposes, such as aroma therapy and insomnia therapy. In such an embodiment of the present invention, the thermoplastic membrane functions as a barrier between the fabric form and the insert's scent-laden inner core, thereby inhibiting wicking of scent from the inner core to the fabric form. Scent residue on the fabric form due to such wicking is undesirable because it could result in increased diffusion rates and unpleasant feel, while potentially damaging foreign objects coming into contact with such residue. The same barrier functionality is realized in accordance with an alternate embodiment of the present invention in which the thermoplastic membrane is incorporated into the fabric form before being combined with the reticulated, hydrophilic composite material of the inner core.

Another embodiment of the present invention involves an apparatus for dispensing or absorbing scent, comprising a housing having an open end, a closed end opposite the open end, and an interior chamber between the open and closed ends. The apparatus also includes an invertible lid having an associated compartment configured to allow the egress or ingress of scent therefrom or thereto. The lid is attachable to the open end of the housing in a first orientation, in which the lid's compartment is positioned entirely within the interior chamber of the housing between the lid and the closed end of the housing, and in a second orientation, in which the lid's compartment is positioned externally of the housing.

In accordance with another particular embodiment of the present invention, a scented material is in the form of a combination, which comprises a reticulated hydrophilic composite material; an optional odorant contained within the composite material; and a thermoplastic membrane surrounding or enveloping the composite material. The reticulated hydrophilic composite material may be in the form of a subcombination, which comprises a hydrophobic scaffold made from a hydrophobic material, and a hydrophilic material which coats the hydrophobic material.

A still further embodiment of the present invention involves another combination, namely, the aforementioned scented material and a fabric enclosure that envelops the scented material. The fabric enclosure can form part of a useful article (e.g., a pillow, cushion or the like)

The present invention also involves scent dispensing methods, a number of which include the step of providing an apparatus which includes: a housing having an open end, a closed end opposite the open end, and an interior chamber between the open and closed ends; an invertible lid having an associated compartment configured to allow the discharge of scent therefrom, the lid being attachable to the open end of the housing in a first orientation, in which the lid's compartment is positioned entirely within the interior chamber of the housing between the lid and the closed end of the housing, and in a second orientation, in which the lid's compartment is positioned externally of the housing. These methods further include the steps of providing the lid's compartment with a scented material and selecting a scent adapted to perform any one or more of a variety of functions, such as attracting game, calming a pet animal, aiding medical diagnostics of a patient, facilitating aroma therapy of an individual (e.g., smell retraining therapy), facilitating the dieting of an individual, and facilitating insomnia therapy of an individual.

A not-necessarily-final embodiment of the present invention involves a system that includes a collection of interchangeable scent cartridges adapted for use in combination with at least one type of compatible scent dispenser, which could be configured to simultaneously receive a plurality of scent cartridges having the same or different scents. When two or more scent cartridges are combined for use in a single dispenser and each cartridge is provided with a scent different from the others, a user of the dispenser can design customized composite (i.e., hybrid) scents.

The system also includes a repository for the collection of interchangeable scent cartridges, as well as a subscription service for users of at least one type of compatible scent dispenser, the subscription service allowing users to place orders for one or more of the interchangeable scent cartridges, which can be implemented as lightweight and compact discs. Due to their lightweight and compact design, the scent cartridges or discs can be removed at will from their associated dispensers, stored in small foil lined bags (such as those they are shipped in), and reused at will. In this way, a new scent cartridge, or the same scent cartridge, can be inserted or reinserted into the same or a different dispenser, thereby providing a user with the flexibility to indulge a variety of different and diverse scent-sampling experiences.

An object of another embodiment of the present invention is to provide a versatile scent-dispensing/absorbing apparatus that is efficient and effective in use, while maintaining simplicity and economics of manufacture and operation. This object, when achieved in accordance with the present invention, results in a commercially viable product.

The present invention has, as an additional object, the ability to dispense scents via molecules (i.e., "dry air"), rather than via droplets, moisture, etc., while requiring no "active" driving mechanisms such as volatile organic compounds (i.e., VOCs), chemicals, electricity, heat or similar propellant enablers to achieve diffusion. In view of recent public healthcare crises, minimizing propellants, especially those moisture-based ones, may help to mitigate the spread of contagious disease.

A further object of the present invention is to provide for personal, portable scent diffusers that can be used anywhere and at any time. For example, the present invention is manifested by a device that can be easily and manually switched between "on" and "off" configurations.

In accordance with the aforementioned objects, the present invention relates to a novel "dry air" scent dispenser, which includes a disc-shaped base, a detachable and invertible lid, a vented cage, and a scent cartridge housed in a compartment formed in the base. The lid can be interchangeably screwed on or otherwise attached to an open end or a closed end of the base, depending upon whether the scent dispenser is in its "off" condition or "on" condition. In the "off" condition, the lid is applied to the open end of the base such that it covers the vented cage to thereby prevent the scent cartridge from interfacing with the outside air (i.e., surrounding atmosphere) to absorb/dispense scents. To switch to the "on" condition, a user removes the lid (e.g., by unscrewing it), whereby the scent cartridge and cage are exposed to the surrounding atmosphere. The lid can then be screwed onto the closed end of the base in an inverted position for storage and potential attachment to a foreign object (e.g., a sun visor for a motor vehicle). In such an "on" condition, scents are dispensed to/absorbed from the surrounding atmosphere. When not in use, the lid can be removed from the closed end of the base and reattached to the base's open end, thereby covering the cage and scent cartridge so as to return the scent dispenser to its "off" condition.

BRIEF DESCRIPTION OF THE DRAWINGS

For a better understanding of the present invention, reference is made to the following detailed description of various exemplary embodiments considered in conjunction with the accompanying drawings, in which:

FIG. 1 is a perspective view of a scent dispenser/absorber in an "off" condition, the scent dispenser/absorber being constructed in accordance with an exemplary embodiment of the present invention;

FIG. 2 is an exploded perspective view of the scent dispenser/absorber of FIG. 1;

FIG. 5 is a side elevational view of another embodiment of a scent dispenser/absorber constructed in accordance with the present invention, the scent dispenser/absorber being shown in FIG. 5 in an "off" condition;

FIG. 6 is a cross-sectional view of the scent dispenser/absorber of FIG. 5, the cross-section being taken through section line 6-6 in FIG. 5 and looking the direction of the arrows;

FIG. 8 is a side elevational view of the scent dispenser/absorber of FIGS. 5-7, the scent dispenser/absorber being shown in FIG. 8 in an "on" condition;

DETAILED DESCRIPTION OF VARIOUS EXEMPLARY EMBODIMENTS

Figure 3:
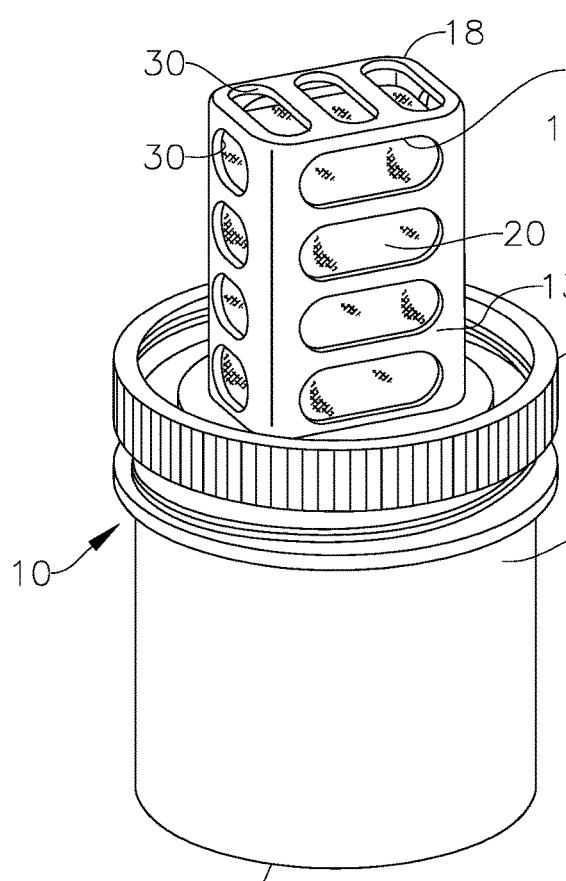
FIG. 3 is a perspective view of the scent dispenser/absorber of FIGS. 1 and 2 in an "on" condition.

Reference will now be made to the various embodiments of the present invention illustrated in FIGS. 1-31. Whenever specified hereinbelow, similar or like reference numbers (increased by, for example, one hundred, two hundred, etc.) may be used in the figures to indicate similar or like structure and/or functionality. It should be understood that the figures depict the various embodiments of the present invention for purposes of illustration only, with the further understanding that some illustrated features are depicted schematically due, for instance, to scaling constraints. One skilled in the art will readily recognize from the following description that alternative embodiments of the structures and methods illustrated in FIGS. 1-31 may be employed, without departing from the objects of the invention described hereinabove.

All terms defined herein should be afforded their broadest possible interpretation, including any implied meanings as dictated by a reading of this specification, as well as any words that a person having skill in the art and/or a dictionary, treatise, or similar authority would assign thereto. For instance, the terms, "for example", "e.g.", "optionally", as used herein, are intended to be used to introduce non-limiting examples, while the phrases "in one embodiment" and "in some embodiments" as used herein do not necessarily refer to the same embodiment(s), although they may. Furthermore, the phrases "in another embodiment" and "in some other embodiments" as used herein do not necessarily refer to a different embodiment, although they may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. Throughout the specification, the meaning of "a," "an," and "the" includes plural references. The terms "comprises" and "comprising" when used herein specify that certain features are present in that embodiment; however, this phrase should not be interpreted to preclude the presence or inclusion of additional steps, operations, features, components, and/or groups thereof.

With the foregoing prefatory comments in mind, reference is now made to FIG. 1, showing a scent dispenser/absorber 10 in a closed or "off" condition, in which a lid 12 is securely fixed to container (i.e., housing) 14. As shown in FIG. 1, the lid 12 can be secured and removably attached to an open end 16 of container 14 in a first orientation (i.e., a closed position), which coincides with the "off" condition of the scent dispenser/absorber 10. In the exemplary embodiment illustrated in FIGS. 1 and 2, as well as in FIGS. 3 and 4, container 14 has external threads 11 on its open end 16 (see FIGS. 2 and 4), while lid 12 has complementary mating internal threads 13 on a skirt 15 of the lid 12 (see FIG. 4) to securely join the lid 12 to the container 14 via a threaded connection (i.e., the lid 12 and container 14 are threadedly attached to one another by threads 11, 13). However, the joinder of the lid 12 and the container 14 may be accomplished via any number of known alternative joining methods, such as dimples, snap fits, press fits, notches, friction fits, pins, magnets, etc. Lid 12 and/or container 14 can be made from glass, polypropylene or related materials with similar properties. As will be described hereinafter, the lid 12 and container 14 can be separated and then joined in a second (i.e., inverted) orientation. To increase enjoyment, the container 14 and/or lid 12 can have a variety of amusing colors, shapes and designs (see, for instance, FIG. 17).

Referring now to FIG. 2, an exploded view of the scent dispenser/absorber 10 is shown. Specifically, the parts are ordered to show their orientation when scent dispenser/absorber 10 is in its "off" condition. A cage 18 is configured to receive scent cartridge (i.e., insert) 20 inside an internal or interior space (i.e., compartment) 22, whereby cage 18 secures and protects the scent cartridge 20. In an embodiment, the cage 18 includes an open end defined by a surrounding, apertured flange 24, the function of which will be described hereinbelow.

When the scent dispenser/absorber 10 is in its "off" condition (i.e., with lid 12 threadedly attached to the open end 16 of container 14), both the cage 18 and the scent cartridge 20 are confined, in an airtight manner, within an inner chamber 26 of the container 14. The inner chamber 26 is sized and shaped such that the scent dispenser/absorber 10 is sufficiently spacious for receiving the cage 18 and the scent cartridge 20 of specified dimensions. When the scent dispenser/absorber 10 is in its "off" condition, the scent cartridge 20 is cut-off (i.e., isolated) from the external environment by cap (i.e., cover) 27, whereby scents emanating from scent cartridge 20 cannot escape from the inner chamber 26 of container 14. The cap 27 also functions as a mounting surface for the flange 24 of the cage 18, which is therefore carried by the lid 12. When the scent dispenser/absorber 10 is configured to operate as an absorber of scents, undesirable odors will be unable to be absorbed by scent cartridge 20 as long as the lid 12 is in its closed position and the scent dispenser/absorber 10 is therefore in its "off" condition.

Figure 4:
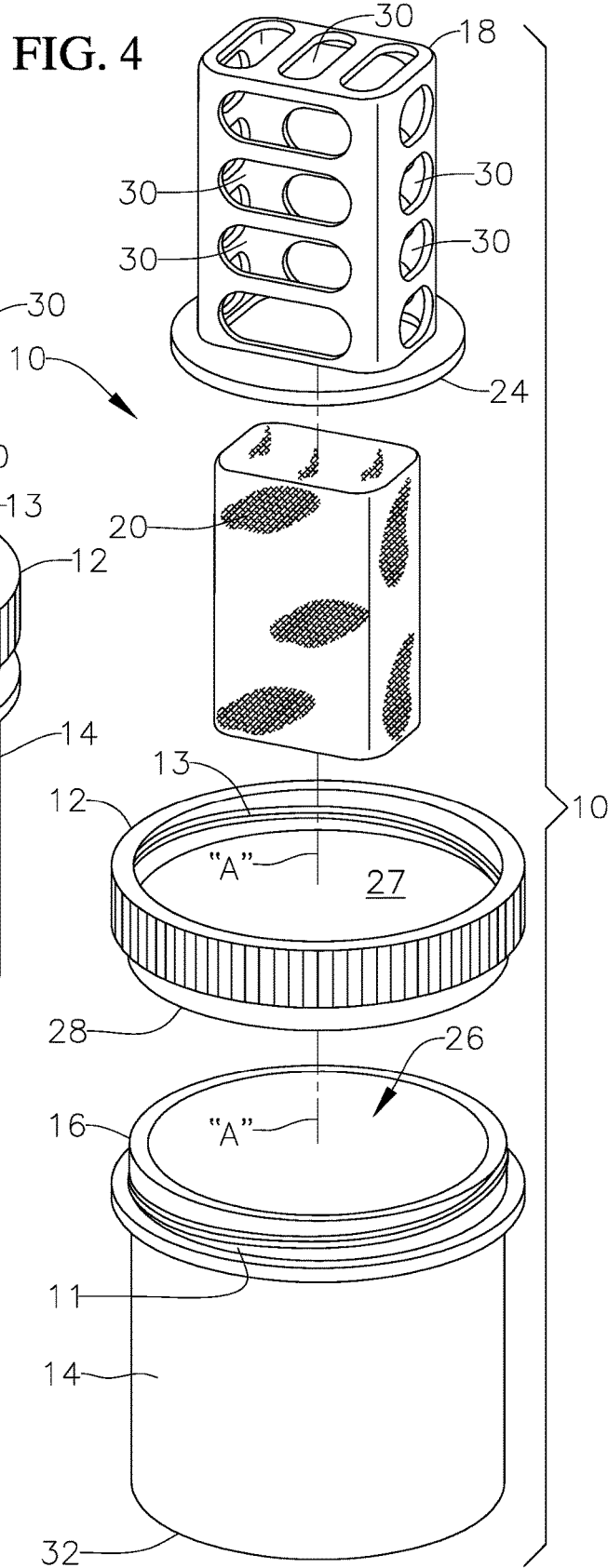
FIG. 4 is an exploded perspective view of the scent dispenser/absorber of FIG. 3.

Referring now to FIGS. 3 and 4, the scent dispenser/absorber 10 is shown in its "on" condition. Switching the scent dispenser/absorber 10 from its "off" condition to its "on" condition can be accomplished by removing the lid 12 and inverting it, whereby the cage 18 and the scent cartridge 20 project outwardly from the lid 12 and externally of the container 14. To position the lid 12 on the open end 16 of the container 14, the lid 12 is provided with a skirt-like ring 28, which functions to center the lid 12 on the open end 16 of the container 14 where it movably sits when the scent dispenser/absorber 10 is in its "on" condition.

When the scent dispenser/absorber 10 is in use in its "on" condition, the scent cartridge 20 communicates with the outside environment via a plurality of vents 30 in the cage 18. In a scent-dispensing mode, the vents 30 allow scent to migrate from the scent cartridge 20 to the surrounding environment. Conversely, in a scent-absorbing mode, the vents 30 would allow scent to migrate from the surrounding environment to the scent cartridge 20.

When not in use, the scent dispenser/absorber 10 can be manually switched from its "on" condition back to its "off" condition by removing the lid 12, inverting it and then reattaching the lid 12 to the container 14 via the aforementioned threaded connection or any other suitable form of connection known in the art. In such an "off" condition, the cage 18 and the scent cartridge 20 are positioned entirely within the inner chamber 26 of the container 14 between the open end 16 thereof and a closed end 32 thereof.

In some embodiments, the lid 12 removably receives the cage 18 by, for instance, a bayonet-type connection, whereby the cage 18 can be removed to expose the open end 24 of cage 18 and to therefore permit removal or replacement of the scent cartridge 20 and/or the cage 18. In an embodiment, the scent cartridge 20 is removable and insertable through the open end of the cage 18 (i.e., the end defined by the apertured flange 24). In an alternate embodiment, the cage 18 is permanently attached to lid 14 by, for instance, a suitable adhesive or any other mechanism known in the art. In further embodiments, the cage 18 can have a door (not shown), whereby the cage 18 can be manually opened for removal or replacement of the scent cartridge 20. In a further embodiment, the cage 18 is constructed from separable halves (not shown) such that the cage 18 can be opened by separating its two halves (e.g., via a plurality of joints or the like). In the various embodiments and configurations described herein, the cage 18 can be made from glass, polypropylene or related materials with similar properties.

Another exemplary embodiment of the present invention is illustrated in FIGS. 5-10. As an initial observation, it is noteworthy that the embodiment of FIGS. 5-10 incorporates a number of structural features similar, if not identical, to counterparts in the embodiment of FIGS. 1-4. In view of such similarities, and in order to facilitate consideration and discussion of the embodiment shown in FIGS. 5-10, structural features of such embodiment that are similar or identical to their counterparts in the embodiment of FIGS. 1-4 will be identified using the same reference number increased by one hundred. It should also be noted that any such counterpart feature of the embodiment shown in FIGS. 5-10 will perform the same function as its corresponding feature in the embodiment of FIGS. 1-4, unless otherwise stated.

Figure 7:
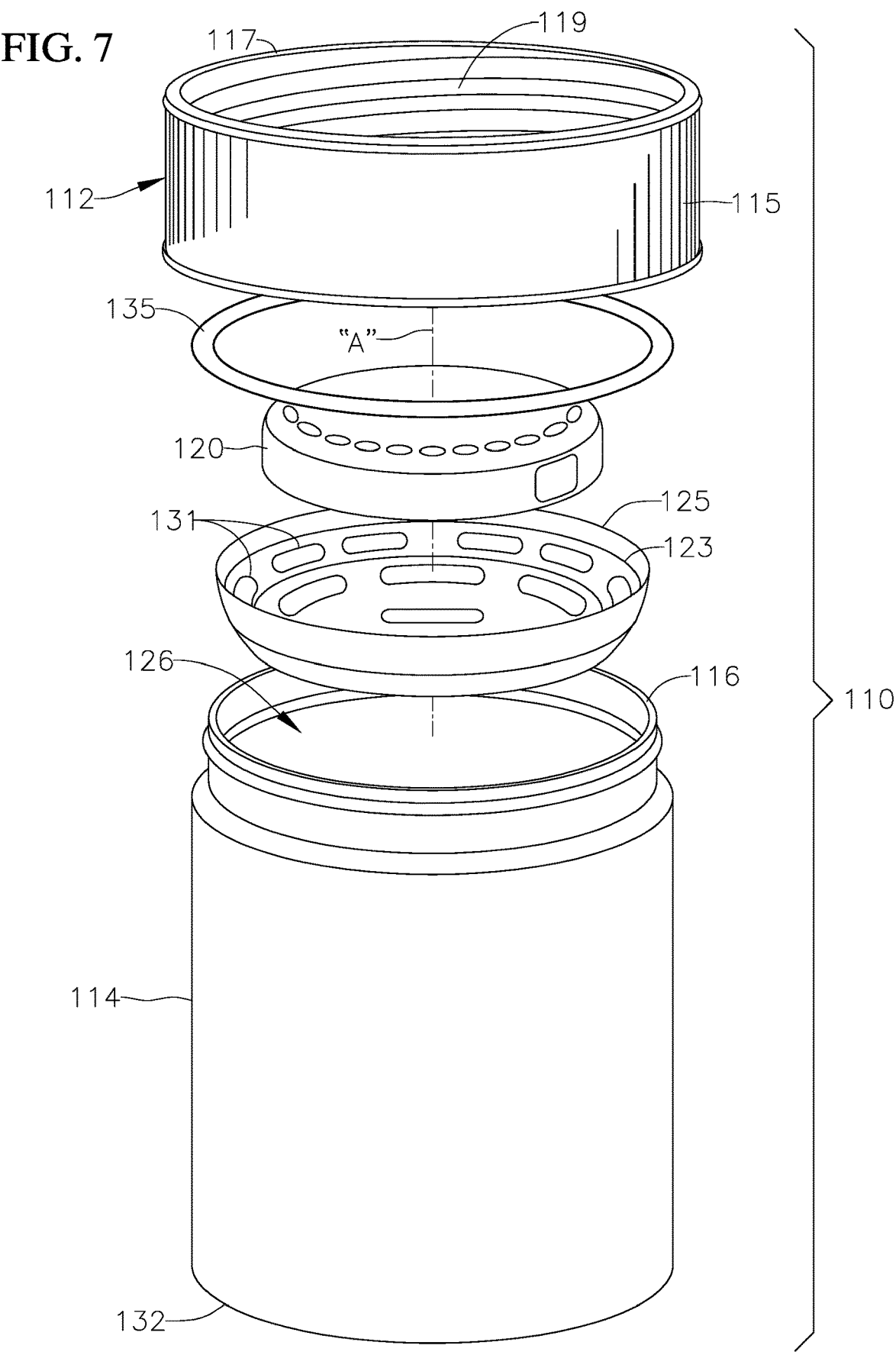
FIG. 7 is an exploded perspective view of the scent dispenser/absorber of FIGS. 5 and 6.

Referring now to FIGS. 5-7, a scent dispenser/absorber 110 is shown in a closed or "off" condition, in which lid 112 is secured and removably attached to an open end 116 of container (i.e., housing) 114 in a first orientation (i.e., a closed position), which coincides with the "off" condition of the scent dispenser/absorber 110. In the exemplary embodiment illustrated in FIGS. 5-7, container 114 has external threads 111 on its open end 116 (see FIGS. 6 and 7), while lid 112 has complementary mating internal threads 113 on skirt 115 of the lid 112 (see, for instance, FIG. 6) to securely join the lid 112 to the container 114 via the threaded connection created by the threads 111, 113. However, the same form of joinder may be accomplished via any number of known joining methods, such as dimples, snap fits, press fits, notches, friction fits, pins, magnets, etc. Lid 112 and/or container 114 can be made from glass, polypropylene or related materials with similar properties. As will be described hereinafter, the lid 112 and the container 114 can be separated and then joined in a second (i.e., inverted) orientation. To increase enjoyment, the container 114 and/or lid 112 can have a variety of amusing colors, shapes and designs.

With particular reference to FIGS. 6 and 7, in which the scent dispenser/absorber 110 is shown in its "off" condition, lid 112 includes a cap (i.e., cover) 127 from which the skirt 115 extends in a first axial direction relative to imaginary axis "A" (see FIG. 7). Another skirt 117 extends from the cap 127 of the lid 112, but in a second axial direction opposite the first axial direction. In other words, the skirts 115, 117 extend from the cap 127 of the lid 112 in opposite axial directions.

As can be seen in FIG. 6, when the scent dispenser/absorber 110 is in its "off" condition, the external threads 111 on the open end 116 of container 114 are threadedly engaged with the internal threads 113 on the skirt 115 of the lid 112. Similar internal threads 119 are provided on the skirt 117 of the lid 112 for a purpose to be described hereinafter. The cap 127 of the lid 112 is also provided with a mounting rim 121 having an annular lip 123 projecting radially outwardly from the mounting rim 121 for a purpose to be described hereinafter.

A domed and apertured diffuser 125 is releasably attached to the mounting rim 121 of the lid 112. More particularly, and with particular reference now to FIG. 6, the diffuser 125 has an annular trough 129 sized and shaped such that the trough 129 can be releasably engaged by the lip 123 on the mounting rim 121 of the lid 112. Apertures 131 are provided in the diffuser 125 for a purpose to be described hereinafter. As shown in FIG. 6, the diffuser 125 and, hence, the apertures 131 therein project downwardly into inner chamber 126, when the scent dispenser/absorber is in its "off" condition.

With continued reference to FIGS. 6 and 7, the lid 112 and diffuser 125 cooperate to form a compartment 133 (see FIG. 6) sized and shaped to receive a scent cartridge 120. When the scent dispenser/absorber 110 is in its "off" condition as shown in FIGS. 5-7, the scent cartridge 120 is confined, in an airtight manner, within an inner or interior chamber 126 of the container 114. The airtight connection between the lid 112 and container 114 is facilitated by the provision of an O-ring (i.e., gasket) 135, which is sandwiched between the open end 116 of the container 114 and the cap 127 of the lid 112. When the scent dispenser/absorber 110 is in its "off" condition, the scent cartridge 120 is cut-off from the external environment by the cap 127 of the lid 112, whereby scents emanating from scent cartridge 120 cannot escape from the inner chamber 126.

With continued reference to FIG. 6, the inner chamber 126 is adapted (i.e., sized and shaped) to house a flameless, scent-free imitation candle 137, the aesthetics of which would be available with or without the functional benefits of dispensing scent. Such aesthetics can be achieved by mounting a light source (i.e., a light-emitting diode "LED") 139 on closed end 132 of the container 114. For increased immersion, the light source 139 can be projected through a flame-shaped globe 141, which can be colored such that globe 141 imitates a real flame. In one embodiment, the container 114 can be partially or fully transparent to allow light emitted from the light source 139 to radiate outwardly. A remote or manually-operated switch 143 can control the operation (i.e., the "on" and "off" states) of light source 139, which may function as a night light, for example. In an alternate embodiment, the light source 139 can be located outside container 114. In other alternate embodiments, decorative modifications, such as a tinted paper filter or decorative patterns (not shown) can be placed as follows: around the light source 139; inside the container 114; and/or on the exterior of the scent dispenser in order to emit different colors and/or patterns of light. These optional patterns, etc. could be permanent or adapted to be interchanged with other decorative elements. For instance, a Halloween theme could be adopted by providing a pattern with Jack-o-lanterns, witches, etc. In one embodiment, such patterns and the like can be interchanged by simply unscrewing the lid 112, removing one pattern and replacing it with another (e.g., a pattern with a Thanksgiving theme could be provided subsequent to the use of a pattern having a Halloween theme).

It should be noted that the inner chamber 126 of the container 114 is configured such that the scent cartridge 120 and/or a number of replacement cartridges (not shown) can be stored within the container 114 during shipping or storage, for instance. It should also be noted that when the scent dispenser/absorber 110 is configured to operate as an absorber of scents, undesirable odors will be unable to be absorbed by scent cartridge 120 as long as the lid 112 is in its closed position and the scent dispenser/absorber 110 is therefore in its "off" condition.

Figure 9:
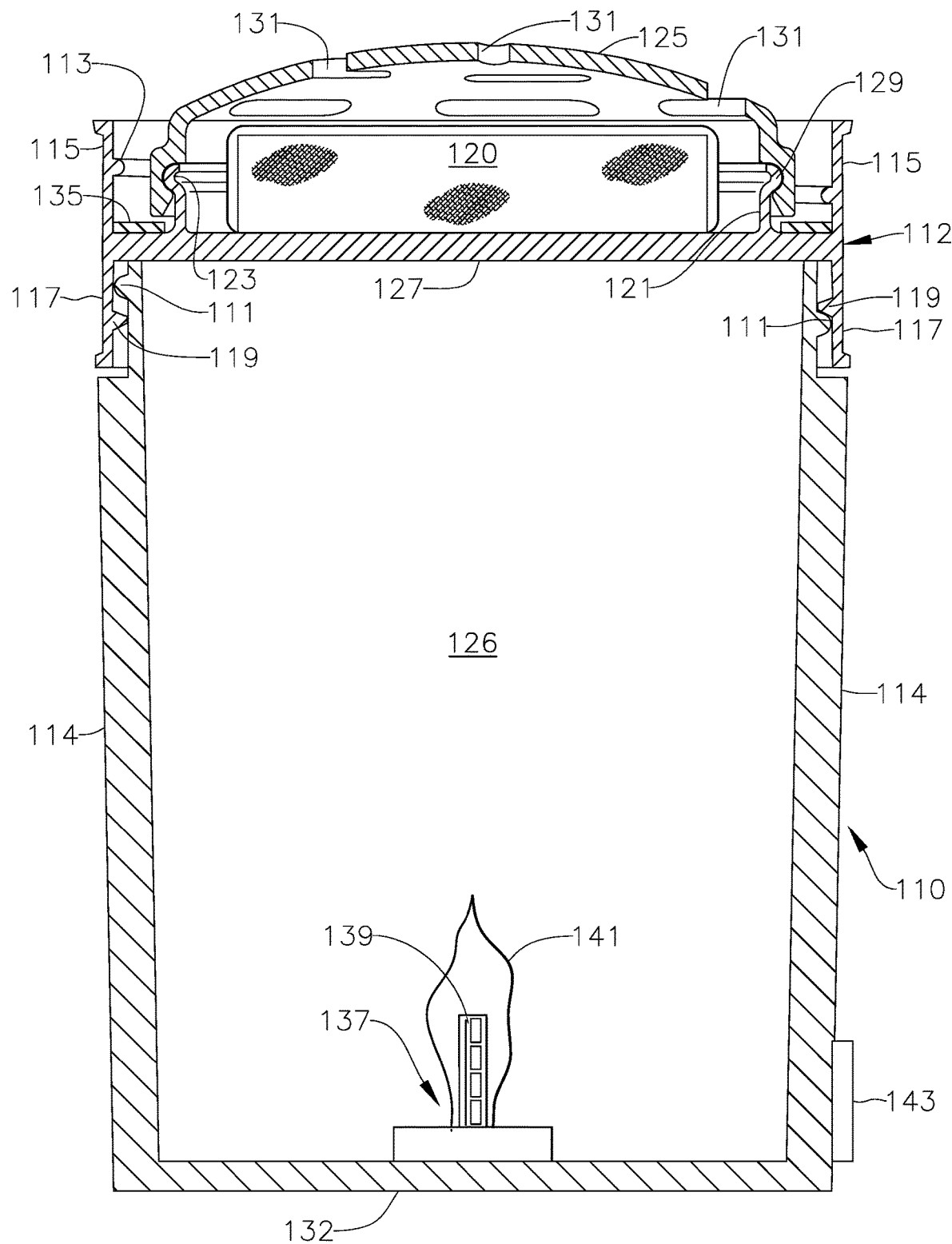
FIG. 9 is a cross-sectional view of the scent dispenser/absorber of FIG. 8, the cross-section being taken through section line 9-9 in FIG. 8 and looking the direction of the arrows.
Figure 10:
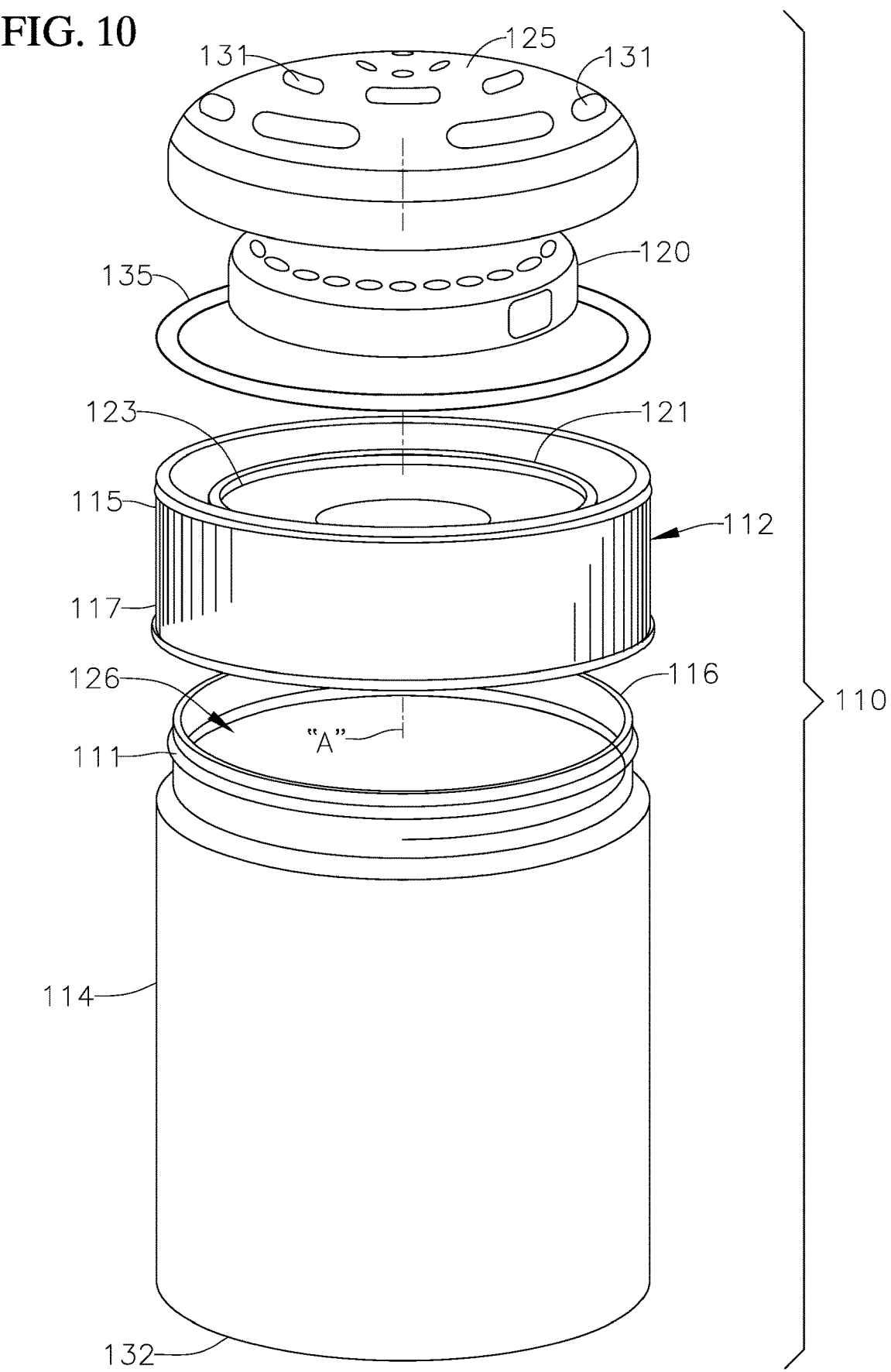
FIG. 10 is an exploded perspective view of the scent dispenser/absorber of FIGS. 8 and 9.

Referring now to FIGS. 8-10, the scent dispenser/absorber 110 is shown in its "on" condition. Switching the scent dispenser/absorber 110 from its "off" condition to its "on" condition can be accomplished by removing the lid 112 and inverting it, whereby the diffuser 125 and the scent cartridge 120 project outwardly from the lid 112 and externally of the container 114. When the scent dispenser/absorber 110 is in its "on" condition, the lid 112 is securely attached to the open end 116 of the container 114 via the engagement of threads 111, 119, while the scent cartridge 120 communicates with the outside environment via the apertures 131 in diffuser 125. In a scent-dispensing mode, the apertures 131 allow scent to migrate from the scent cartridge 120 to the surrounding environment. Conversely, in a scent-absorbing mode, the apertures 131 would allow scent to migrate from the surrounding environment to the scent cartridge 120.

When not in use, the scent dispenser/absorber 110 can be manually switched from its "on" condition back to its "off" condition by removing the lid 112, inverting it and then reattaching the lid 112 to the container 114 via the engagement of threads 111, 113. In such an "off" condition, the diffuser 125 and the scent cartridge 120 are positioned entirely within the inner chamber 126 of the container 114 between the open end 116 thereof and the closed end 132 thereof.

The scent dispenser/absorber 110 is especially adapted for use in combination with a cupholder in a land, sea or air vehicle. So as to adapt the scent dispenser/absorber 110 for such uses, the container 114 can be sized and shaped to be received within common cupholders, the size and shape of the container 114 comporting with the associated dimensions of such cupholders. In connection with such uses, the lid 112 of the scent dispenser/absorber 114 will be securely attached to the container 114 due to the threaded connection created by threads 111, 113, 119, whether the scent dispenser/absorber 110 is in its "on" condition or its "off" condition.

The scent cartridges 20, 120 may be made of foam or any other suitable material (e.g., reticulated hydrophilic polyurethane foam composite, preferably about ⅜ of an inch in thickness) adapted to absorb or adsorb a volatile scented substance. In the exemplary embodiments that follow, the scent cartridges 20, 120 perform scent dispensing functions using evaporation to emit scent molecules as "dry air" (i.e., without droplets). In such "dry air" embodiments, the scent cartridges 20, 120 are infused with odorant such that odorant molecules spread throughout the surface of the material of the scent cartridges 20, 120. With the scent dispenser/absorbers 10, 110 in their "off" conditions (see FIGS. 1 and 2 and FIGS. 5-7, respectively) evaporation of the odorant molecules will be contained within the containers 14, 114, respectively, thereby filling the inner chambers 26, 126 around the scent cartridges 20, 120, respectively. In such a condition, the scent dispenser/absorbers 10, 110 are adapted for storage and/or transportation.

In one embodiment, the scent cartridges 20, 120 comprise reticulated hydrophobic polyurethane foam (Product No. RT030CHRSC1) from Ionac (Woodbridge INOAC Technical Products, 100 Carol Place, Moonachie, NJ 07074), which material provides the scaffolding for the scent cartridges 20, 120. It is a desirable material for the scaffolding of the scent cartridges 20, 120 because scent molecules only weakly interact with it. Due to the fact that polyurethane molecules are not volatile at typical pressures and temperatures, the odorant scent released from the scent cartridges 20, 120 into the inner chambers 26, 126 of the containers 14, 114, respectively, will not be adulterated by the scaffolding (i.e., the aforementioned polyurethane foam).

To prepare the scent cartridges 20, 120, the foam or scaffolding material can be coated with a thin layer of prepolymer, such as Dow Chemical's HYPOL JM 5005, which can then be reacted with water molecules to form a hydrophilic polyurethane surface coating. The large hydrophilic polyurethane molecules are non-volatile and do not contribute to the scents produced. The hydrophilic polyurethane is polar in nature and has a degree of affinity for scent molecules.

As the hydrophilic polyurethane surface coating is curing, $CO_2$ out gassing results in a larger surface area. On the surface of the reticulated material, the scent adheres along the hydrophilic polyurethane surface due to their polar interactions. There is a large surface area available for evaporation and a "headspace" within the material that generally contains a high level of "dry air" scented vapor. Through this process, the scent cartridges 20, 120 can release a high quality representation of the original scent, while ensuring that the scent lasts a long time. Various thicknesses (e.g, ⅜") and pore sizes (e.g., 30 pores per inch) of reticulated base material are options.

The result is that when the scent dispenser/absorbers 10, 110 are switched to their "on" conditions, as described above, a faithful iteration of the original odorant scent will be released for sampling or other purposes when used in conjunction with scent cartridges 20, 120. In other words, the aforementioned sampling step is carried out in an environment in which essentially ambient air contains scent molecules, but no liquid. Thus, the scent dispenser/absorbers 10, 110 allow scents to be stored, transported and sampled in a non-liquid form, the subsequent sampling being performed in a "passive" manner.

Furthermore, when coupled with the ability of the presently proposed scent dispensers (e.g., the scent dispenser/absorbers 10, 110) to be sealed when not in use, a longer effective scent life can be achieved. This is in addition to the fact that the inventive scent inserts (e.g., the scent cartridges 20, 120) also affect the scent diffusion curve, which would further advance the goal of increasing the life of the scenting function of their associated scent dispensers.

While the scent cartridges 20, 120 have been described with reference to a particular embodiment thereof, it should be understood by those skilled in the art that various changes may be made and equivalents may be substituted without departing from the true spirit and scope of the present invention. For instance, the scent dispenser/absorbers 10, 110 are adapted for use with other types of scent capturing and diffusing media, such as the scent cell disclosed in U.S. Patent Application Publication No. 2017/0312380 (see especially Paragraphs [0048] to [0050]), U.S. Pat. No. 8,544,766 (see especially Column 6, lines 30-59) and U.S. Pat. No. 6,617,014, all three of which patent publications are incorporated herein by reference in their entireties. In addition, the scent cartridges 20, 120 can be replaced by, for example, a scent cartridge adapted to absorb and/or adsorb a volatile scented substance, while allowing the ready passage of air therethrough. In some embodiments, the scent cartridges 20, 120 would contain an amount of volatile scented substance, such as those used in perfumes, as well as those used for attracting game, for calming a pet, for functioning as a diet aid, for aroma therapy, for medical applications, or for other uses which are known or may become known, such as providing cannabis-derived and/or hemp-derived scents, fragrances, etc. In other embodiments, the scent cartridges 20, 120 would be designed such that the scented substance may be added directly to the scent cartridges 20, 120 to replenish or change the scent.

By way of further example, the scent cartridges 20, 120 may be made of any material that can carry and release volatile scented substances. In some embodiments, it could be made of an absorbent fibrous material or closed cell foam having air passages penetrating therethrough. In other embodiments, the scent cartridges 20, 120 could be made of an open-cell foam that presents an appreciable ratio of surface area to volume of foam, with higher ratios typically being preferred. In such embodiments, the foam may be a hydrophilic foam or have a hydrophilic material exposed at the surfaces of its cells. Other suitable embodiments could utilize an open-cell foam composite made of substantially hydrophobic foam to provide structure to the composite and substantially hydrophilic foam exposed at the surfaces of its cells, such as the foam described in U.S. Pat. No. 6,617,014, whose disclosure in that regard is incorporated herein by reference.

In yet other embodiments, the scent cartridges 20, 120 may comprise a nonwoven fibrous material substrate coated with, for example, a substantially hydrophilic foam coating which is exposed at the surface and in interstitial spaces within the nonwoven fibrous material. The interstitial spaces within the nonwoven fibrous material form air passages penetrating therethrough to allow the flow of air. Examples of suitable nonwoven fibrous materials include, without limitation, cotton, felt, silk, or combinations thereof. As will be recognized by persons of ordinary skill in the relevant art, such embodiments would be useful when the volatile scented substances employed to impart scent or alternative odor to the scent cartridges 20, 120 are of the types that may react with and degrade some hydrophobic foams (see, for example, U.S. Pat. No. 8,544,766, whose disclosure in that regard is incorporated herein by reference).

One possible process for producing a non-woven, fibrous scent cartridge involves contacting a substrate of nonwoven fibrous material with a prepolymer emulsion and then polymerizing or curing the emulsion. By way of further example, the substrate can be dipped or immersed in the prepolymer emulsion, which can also be applied by brushing or otherwise coating onto the substrate. In an embodiment of such a process, the substrate of nonwoven fibrous material may be provided as a sheet or block and then coated with the prepolymer emulsion, followed by polymerization or curing of the emulsion to form the substantially hydrophilic foam on the nonwoven fibrous substrate. The substrate can then be cut into appropriately sized and shaped pieces to produce a scent cartridge (e.g., scent cartridge 20 or scent cartridge 120) suitable for use with its associated scent dispenser (e.g., the scent dispenser/absorber 10 or the scent dispenser/absorber 110).

Figure 11:
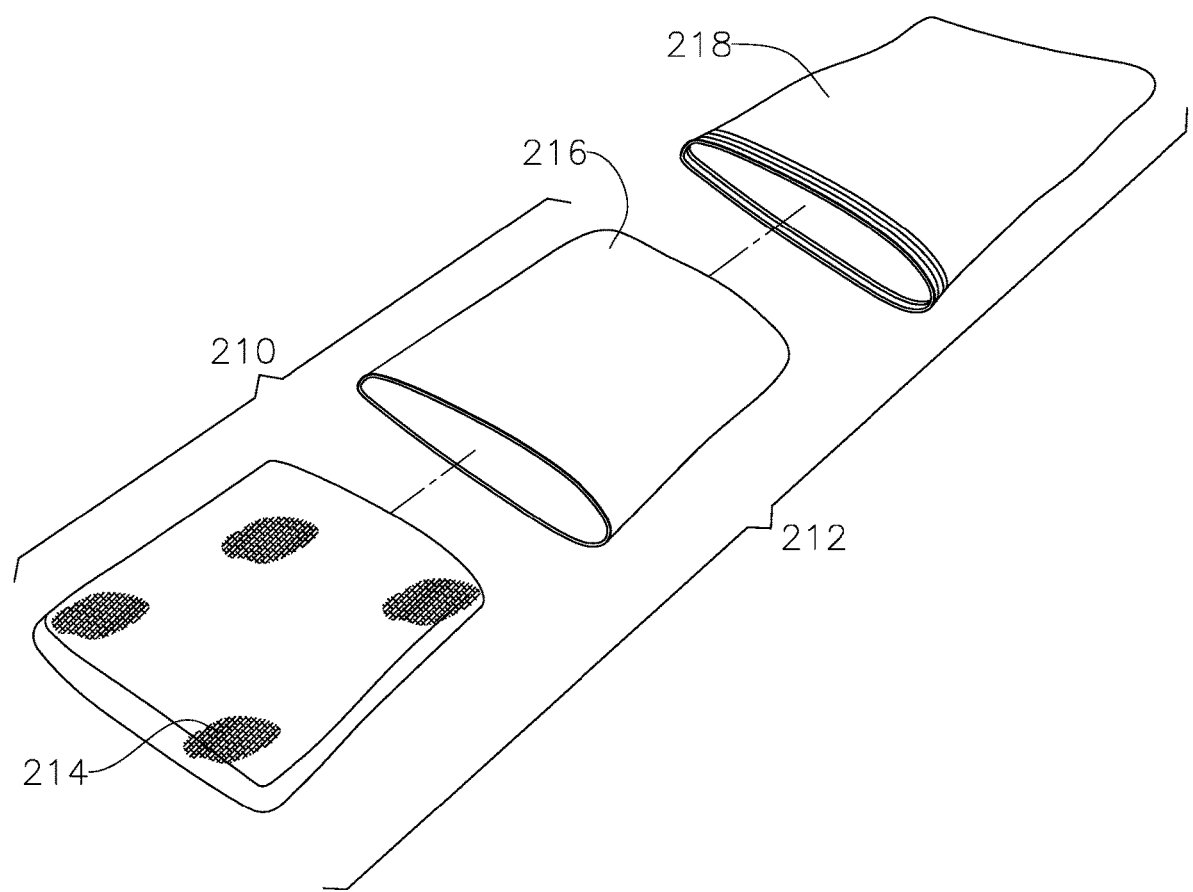
FIG. 11 is an exploded view, shown in perspective, which schematically illustrates various steps in the manufacture of a scent-dispensing insert (i.e., subcombination) and an end product incorporating same (i.e., combination), both of which are representative of other aspects of the present invention.
Figure 12:
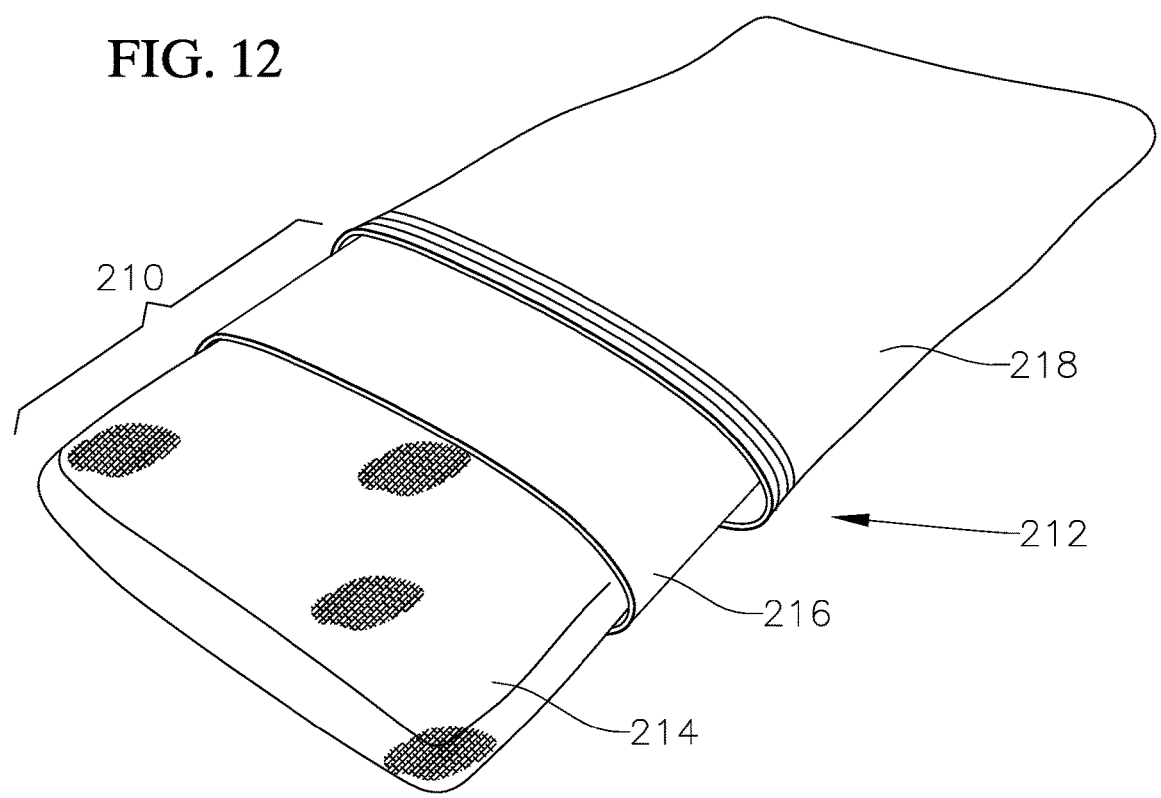
FIG. 12 is a partial exploded view, shown in perspective, of the end product produced by the manufacturing steps illustrated schematically in FIG. 11.

Suitable scent cartridges can be constructed in accordance with still further embodiments thereof. For instance, and with reference to FIGS. 11 and 12, another alternative scent cartridge arrangement is illustrated, along with a method of making same. With particular reference to FIG. 11, there is shown a series of illustrations corresponding to various steps in the manufacture of a scent-dispensing insert 210 and a product 212 incorporating the insert 210. More particularly, and referring still to FIG. 11, the initial step in the manufacturing process involves providing a reticulated, hydrophilic composite material 214, such as a foam composite made up of a scaffold of an open cell hydrophobic material having a plurality of surfaces defining a plurality of pores (e.g., in a range of from about thirty pores per inch to about fifty pores per inch), and a coating of a substantially hydrophilic foam material disposed upon the surfaces of the hydrophobic foam. The resulting foam composite exhibits the structural characteristics of the hydrophobic foam and the absorbency characteristics of the hydrophilic foam. Other suitable materials are disclosed in, for example, U.S. Pat. No. 6,617,014, whose entire disclosure is incorporated herein by reference, as well as in U.S. Pat. No. 10,912,855, whose entire disclosure is incorporated herein by reference. The size and shape of the composite material 214 would be dependent upon its intended end use, examples of which will be discussed hereinafter.

While not depicted in FIG. 11, the next step in the manufacturing process involves loading, at least partially, an appropriately sized and shaped piece of the aforementioned composite material 214 with a liquid odorant. By way of example, the liquid odorant can be a volatile scented substance, such as those identified hereinabove, as well as those useful for aroma or insomnia therapy, for medical diagnostic applications and/or for animal husbandry (i.e., pet calming) purposes by, for instance, having the scent emulate that of the pet owner.

Returning now to FIG. 11, the next step in the manufacturing process involves enveloping, encasing, enwrapping or otherwise enclosing the scented composite material 214 in a heat-sealable, thermoplastic membrane or film 216 having a permeability that allows scent molecules originating from the odorant to be released from the composite material in a passive and continuous (i.e., without manual or mechanical manipulation) manner. In use in combination with the composite material 214, the thermoplastic membrane or film 216 performs a metering function in that it prevents, or at least inhibits, the release of liquid, while permitting the release of scent molecules, thereby delivering scent to a user in a dry format free from mists, sprays, aerosols and liquid. To facilitate their combination, the scented composite material 214 and the thermoplastic membrane or film 216 can be shaped to complement one another.

Suitable thermoplastic materials include, but are not limited to, the following copolymers: high density polyethylene (HDPE); low density polyethylene (LDPE); polypropylene (PP); and ethylene vinyl acetate (EVA), all of which would have a thickness determined by their intended end use. In an embodiment, the heat-sealable thermoplastic membrane has a thickness of about 3 millimeters to about 6 millimeters. In a preferred embodiment, adsorbency of at least one unit of weight of scent per one unit of weight of core material is achieved.

One specific example of a suitable thermoplastic film is 3M's CoTran Ethylene Vinyl Acetate Membrane Film 9712, 18.5% VA, 2 mil, translucent, no corona treatment. Other suppliers of suitable thermoplastic materials for use in practicing the present invention include, but are not limited to, the following companies: Bemis Company; Berry Plastics; Sigma Plastics; and Sealed Air Corporation. Regardless of the supplier and type of thermoplastic film that is utilized, the resulting combination (i.e., the scent-dispensing insert 214) includes an inner core, which is in the form of the scent-laden composite material 214, and an outer skin, which is in the form of the thermoplastic membrane or film 216 heat-sealed around the inner core.

The thermoplastic membrane or film 216 can have an opaque surface (not shown) capable of being printed on for advertising and/or informational purposes, for instance. In other embodiments, adding the heat-sealable, thermoplastic membrane to the core material enables the placement of imagery or other content on the surface of the product associated with the scent contained therein. By exploiting the association of scent with images, an enhanced sensory experience can be provided to the user.

The resulting combination, in addition to carrying the desired scent in a non-liquid state for use in, for example, the scent dispensers 10, 110, achieves multiple advantages. For instance, the combination of the foam composite and the thermoplastic membrane achieves a synergy that further increases the lifetime of the scented product. Both the foam composite and the membrane reduce evaporation rates. The effective lifetime, as a function of the capacity of the scented material, therefore increases.

The foam composite holds and releases scent molecules over time, doing so while reducing the effective evaporation rate of the scent and lengthening the duration of release relative to other passive diffusion methods that do not utilize the foam composite material of the present invention. The foam composite also serves to physically retain the scent, helping to prevent leaks and spills. The thermoplastic membrane also contributes to preventing leaks and/or spills.

The inventive combination also does not allow odorant oils in the substrate to wick out because the thermoplastic membrane functions to cause the scent molecules to permeate through the tortuous paths in the non-porous (i.e., solid) film structure membrane. This functionality of the thermoplastic membrane allows scent molecules to be discharged (i.e., diffused) therefrom in gaseous form as dry, but scented, air. In some embodiments, the thermoplastic membrane would stop any scent-associated liquids from escaping, even when the inventive scent insert is dropped.

In use, the heat-sealable, thermoplastic membrane creates an additional barrier for the scent molecules. While one side (i.e., the exterior side) is open to the atmosphere and has a low concentration of scent molecules, the other side (i.e., the interior side) has a much higher concentration of scent molecules. Provided the evaporation rate is high relative to the diffusion of scent molecules through the membrane, there will be minimal residual scent adhering to the membrane itself.

A further advantage of the present invention is that the thermoplastic membrane can be overfilled, either accidentally or intentionally, while still not permitting scent to escape. Additionally, the presently proposed invention reduces the amount of scenting liquid needed. This reduces the amount of liquid the user needs to interact with, while also minimizing the weight and cost of associated product shipments (e.g., in connection with the library concept disclosed herein). In some embodiments, replacement scent can be provided in 1 oz bottles weighing as little as 0.75 grams.

The combination of a reticulated hydrophilic polyurethane foam composite heat sealed in an EVA thermoplastic membrane has notable advantages. Typically, EVA is used to meter scents in their liquid or solid states by using EVA beads or EVA bags of fluid. However, when used in combination with the foam as presently proposed, the scent is evaporated within the EVA enclosure, thereby creating a condition that provides a concentration of scent on the inside of the EVA that is similar to the vapor pressure of the scent being delivered. This condition (i) controls the rate of diffusion relative to the evaporation rate of the scent, thereby enabling longer durations of use, and (ii) minimizes the amount of scent adhering to the outer (i.e., exterior) surface of the membrane. Among other effects, this condition enables manual handling of the scented product or combination (e.g., the scent cartridges 20, 120), while leaving minimal residual scent on a user's hands, clothes or any other surfaces the EVA may be placed in contact with.

A scent that has a lower vapor pressure would diffuse in its liquid state through an EVA bead or bag until a substantial film builds up on the outer surface to slow or halt diffusion. In contrast, the foam of the present invention would adsorb liquid scent, and the rate of diffusion through the thermoplastic film would be limited only by what could already evaporate from the foam matrix at a given temperature; consequently, the rate at which molecules reach the surface of the thermoplastic membrane would be similar to the rate at which they are evaporating from the surface. Additionally, there is no surface film on, for instance, the scent dispensing insert 210.

For the particular end use disclosed herein (see FIG. 12), the aforementioned core/skin combination (i.e., the scent-dispensing insert 210) would be appropriately sized, shaped and scented to function as a scent-dispensing insert for a pillow, cushion or pouch 218 having a fabric covering or casing. Thus, the next step in the manufacturing process would involve placing the scent-dispensing insert 210 inside the fabric-covered pillow, cushion or pouch 218, where the insert 210 would provide a long-lasting, high-fidelity scent-dispensing experience (see FIGS. 11 and 12).

As explained above, adding the heat-sealable, thermoplastic membrane to the core material provides an additional containment means for the liquid scent when adsorbed in the foam composite. This effect protects against the escape of scent liquid when the product is, for instance, dropped. This result is desirable for multiple reasons. For instance, customers or other end users can handle scented products without getting an appreciable amount of scent on their skin, clothes, etc. Furthermore, the scented product can be placed on a finished surface (e.g., a table) with minimal to low risk of damaging the finish with scent. This being the case, the present invention can provide diffusion, even while touching finished surfaces, without harming those surfaces. Similarly, the present invention can be used in conjunction with fabrics without wicking out or damaging the fabrics.

When used in combination with a pillow or cushion (see, for instance, FIG. 12), the thermoplastic outer skin 216 of the insert 210 can be provided with anti-microbial and/or anti-fungal properties, for hygienic purposes. The insert 210 can simply be placed inside the pillow or cushion 218; or it can be attached to the pillow's or cushion's fabric covering or casing by sewing, stitching or any other conventional attachment means. In use, scent molecules originating from the odorant are passively and continuously released from the reticulated, hydrophilic inner core 214 of the insert 210. The scent molecules released from the inner core 214 of the insert 210 pass through the thermoplastic outer skin 216 of the insert 210 and then through the fabric casing of the pillow or cushion 218, before being diffused into the surrounding environment to provide a faithful iteration of the original odorant or scent. As mentioned above, wicking of scent from the inner core 214 to the fabric of the pillow or cushion 218 is inhibited by the thermoplastic outer skin 216, which functions as a barrier between the fabric and the inner core. Scent residue on the fabric is to be avoided because it could result in increased diffusion rates and unpleasant feel, while potentially damaging foreign objects coming into contact with such residue. For cleaning and/or sanitizing purposes, the fabric could be of a washable variety.

When used in combination with a pouch, the size of the insert 210 would be reduced to account for the reduced size of the pouch, which would typically be smaller than that of a pillow or cushion. The pouch could be adapted for releasable attachment to a dog pen, for example, where it would emit a scent (e.g., a scent reminiscent of the pet's owner) selected to have a calming effect on the pet housed in the pen.

In some embodiments, evaporation rates for personal scenting applications in accordance with the present invention range from about 5 mg to about 25 mg per day. In an embodiment, a scent dispenser made in accordance with an embodiment of the present invention could be specially adapted for use with a desk. Such a dispenser would be desirable to increase productivity, soothe a user and operate as a light source if, for instance, combined with an LED light.

Similar objectives can be achieved by adapting the inventive device for use in a car or other land, sea or air vehicle. This could entail both driving-related scents, as well as such features as adapting the dimensions of the device to fit into a conventional cupholder. By way of further example, the device, especially when in the form of a pouch, could be adapted for use as a hanging household and/or vehicle air freshener.

It should be understood that the volume of the foam-like inner core 214 of the insert 210 can be varied to control the effective life and/or the scent diffusion capacity of the insert 210. The permeability and/or thickness of the thermoplastic outer skin 216 can also be selected to control the effective (i.e., operational) life and/or the scent diffusion capacity of the insert 210. By way of example, the active life and rate of diffusion may be varied by adjusting membrane/film properties, such as thickness, vinyl acetate concentrations, number of layers, etc. Adding the heat-sealable, thermoplastic membrane to the core material allows for the further control of the rate of evaporation by, for example, adjusting the material or the physical construction of the membrane/film itself. Other factors capable of controlling diffusion rates and capacities include, but are not limited to, the volume and surface area of foam in conjunction with variations of the surface area of membrane material. These factors enable the device to be better adapted to meet the diffusion needs of the wide variety of scent uses. For EVA specifically, the permeability of typical odorant molecules is generally higher when used with higher concentrations of VA. Certain plastics have negligible permeabilities by comparison. The effects of varying further parameters will be demonstrated in the Examples section below, as well as by the following representative parameters. The thermoplastic membrane may comprise one or more polymers selected from the group consisting of HDPE; LDPE; PP and EVA. When the polymer is EVA, the EVA can be selected such that the EVA has (i) a VA concentration in a range of from about 3.5% to about 18.5% of the EVA, and (ii) a thickness in a range of from about 2 millimeters to about 6 millimeters. When the polymer is HDPE, the HDPE can have a thickness in a range of from about 1 millimeter to about 6 millimeters. When the polymer is LDPE, the LDPE can have a thickness in a range of from about 1 millimeter to about 6 millimeters. The hydrophobic core of the scaffold can have (i) a volume in a range of from about 0.1 cubic inches to about 4 cubic inches (or, more preferably, from about 0.5 cubic inches to about 2.25 cubic inches), and (ii) a weight in a range of from about 150 milligrams to about 6 grams. The hydrophobic core of the scaffold absorbs liquid odorant and releases scent molecules emanating therefrom, the scent molecules being discharged from the scaffold through the hydrophilic coating thereof. The scent molecules emanating from the liquid odorant (e.g., an amount of liquid odorant in a range of from about 50 milligrams to about 12 grams) create a relatively low level of residual scent on the outer surface of the thermoplastic membrane, which level is dependent upon the liquid odorant's evaporation rate (e.g., in a range of from about 5 mg to about 25 mg per day).

While in some embodiments, such as those disclosed hereinabove, the insert 210 functions as an interior attachment to a useful article, in other embodiments the insert 210 can be adapted to function as an exterior attachment to a useful article, such as various different types of articles worn by a user (e.g., backpacks, jewelry, belts, etc.). The insert 210 can also be used to produce scents designed to improve an individual's memory, as well as a learning experience that an individual may be undertaking (even when such an experience is undertaken during sleep).

Figure 14:
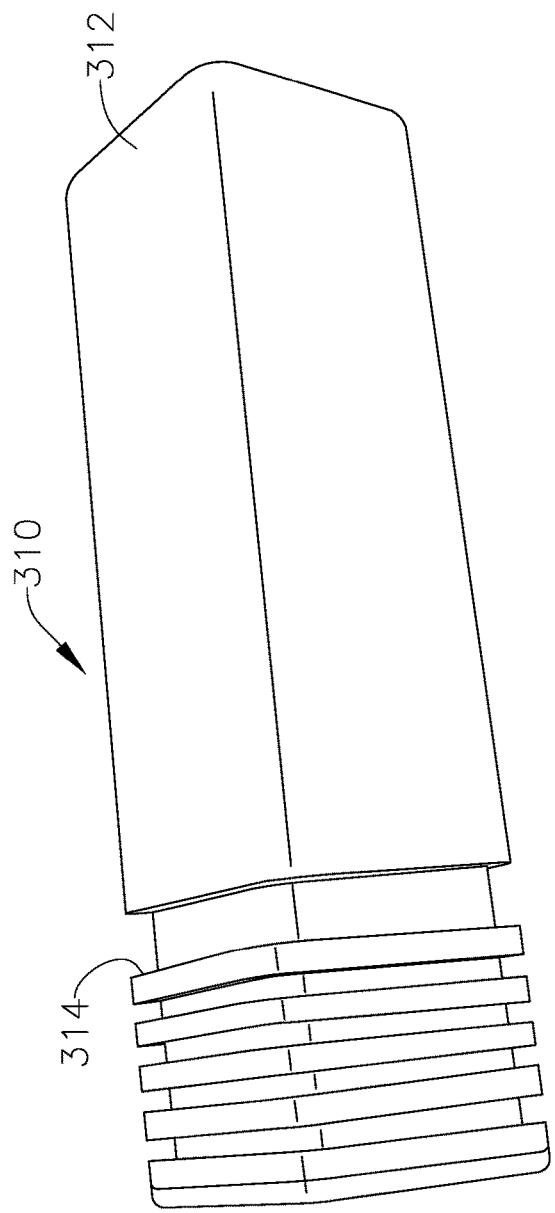
FIG. 14 shows a further embodiment of a scent dispenser/absorber constructed in accordance with yet another aspect of the present invention, the scent dispenser/absorber of FIG. 14 being shown in an "off" condition.
Figure 15:
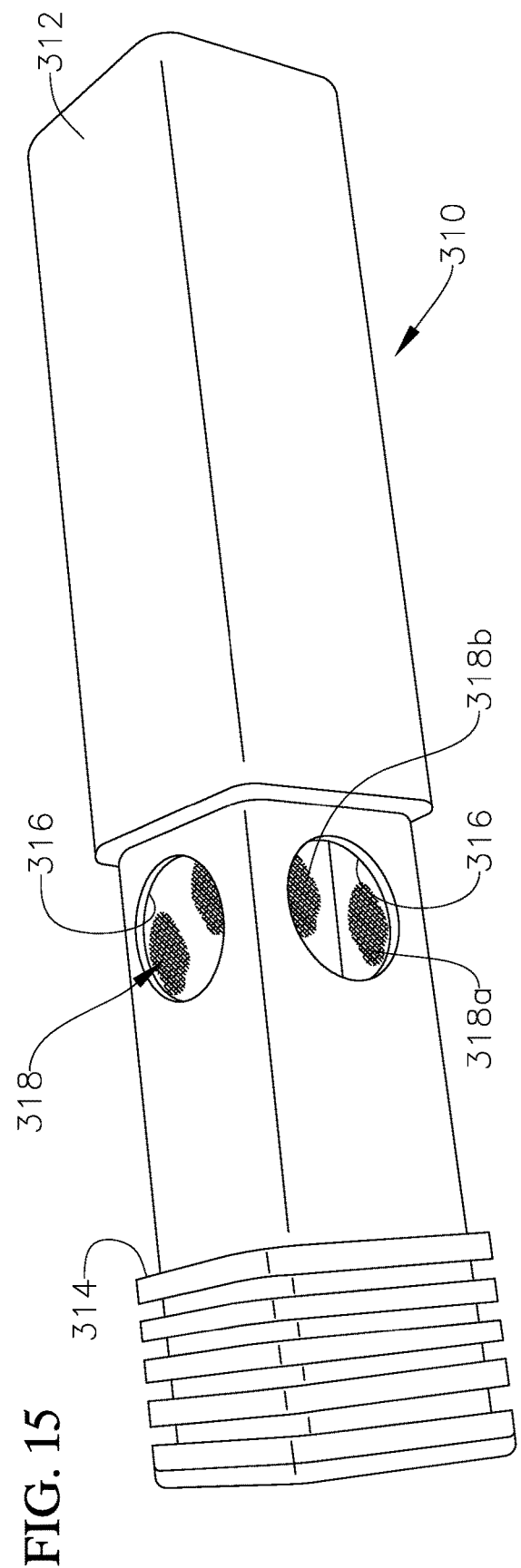
FIG. 15 shows the scent dispenser/absorber of FIG. 14 in a fully "on" condition.
Figure 16:
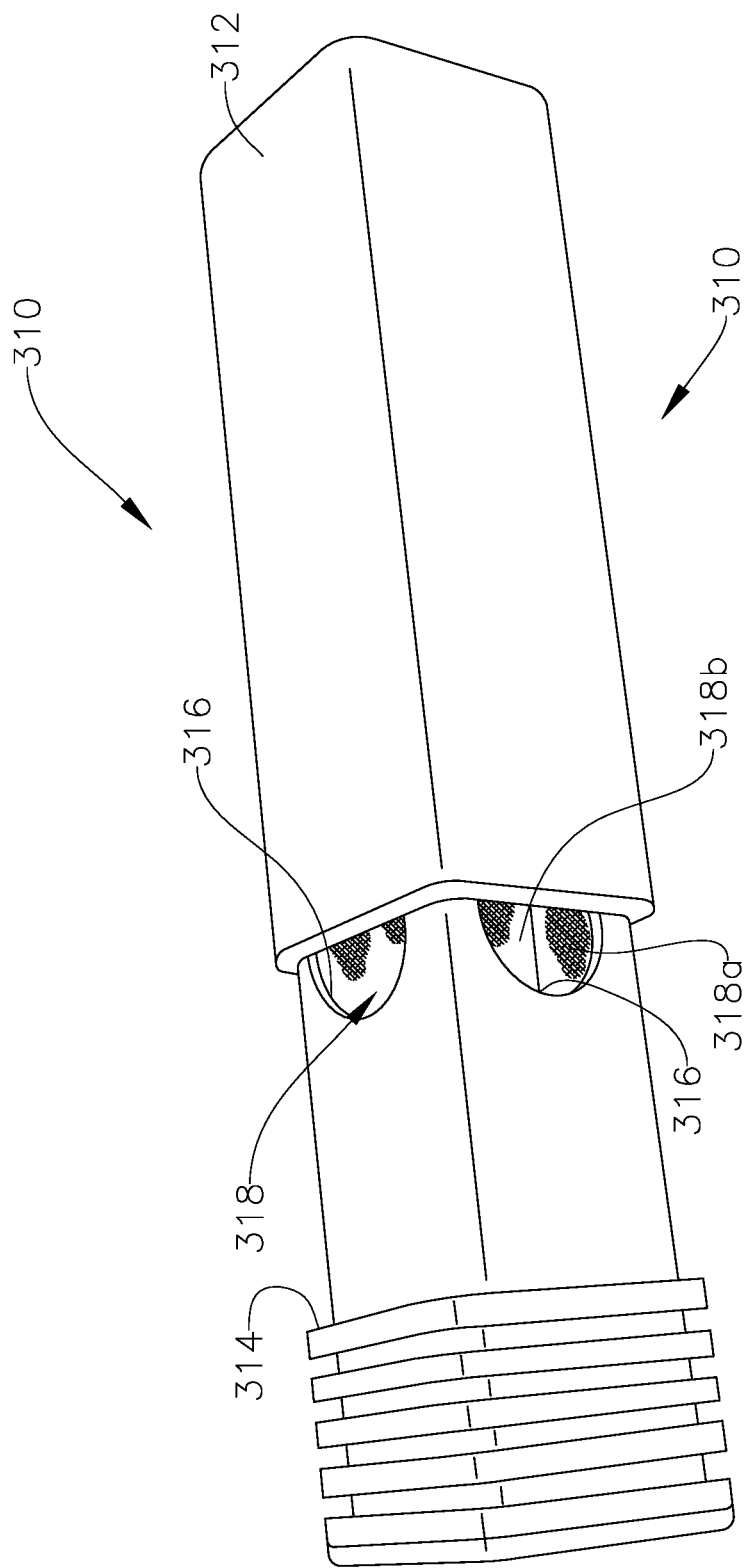
FIG. 16 shows the scent dispenser/absorber of FIGS. 14 and 15 in a partially "on" condition.

FIGS. 14-16 show a non-invertible scent dispenser/absorber 310. For example, the scent dispenser/absorber 310 can be transitioned between a fully closed position (i.e., "off" condition) as shown in FIG. 14, and a fully open position (i.e., "on" condition) as shown in FIG. 15. In operation, a housing 312 works in telescopic fashion with an interior casing 314, such that the housing 312 operates as a piston and the casing 314 as a cylinder. To transition between the closed position illustrated in FIG. 14 and the open position illustrated in FIG. 15, a user can grip the casing 314 and pull it outward from the housing 312. As the casing 314 is extended in such a telescopic fashion, ports 316 on the casing 314 are completely exposed to the open air, thereby placing scent cartridge 318 in communication with the surrounding environment. While the scent cartridge 318 can be provided as a single integrated part, it may also have a multi-part construction as shown in, for example, FIGS. 15 and 16, which show a pair of scent cartridges 318*a* and 318*b* arranged back-to-back within the casing 314. If the scent cartridges 318*a* and 318*b* are provided with different scents, any of the ports 316 aligned solely with scent cartridge 318*a* would emit one scent, while any of the ports 316 aligned solely with the scent cartridge 318*b* would emit a different scent and any of the ports 316 aligned with both of the scent cartridges 318*a* and 318*b* would emit a customizable, composite (i.e., hybrid) scent. This customizable, scent-mixing can also be employed by other non-invertible scent dispensers, such as those disclosed in the aforementioned U.S. Pat. No. 8,544,766. It should also be noted that the amount of scent diffusion can be limited by positioning the casing 314 such that the ports 316 are partially exposed to the air and partially blocked by the housing 312 (see, for instance, FIG. 16).

Figure 17:
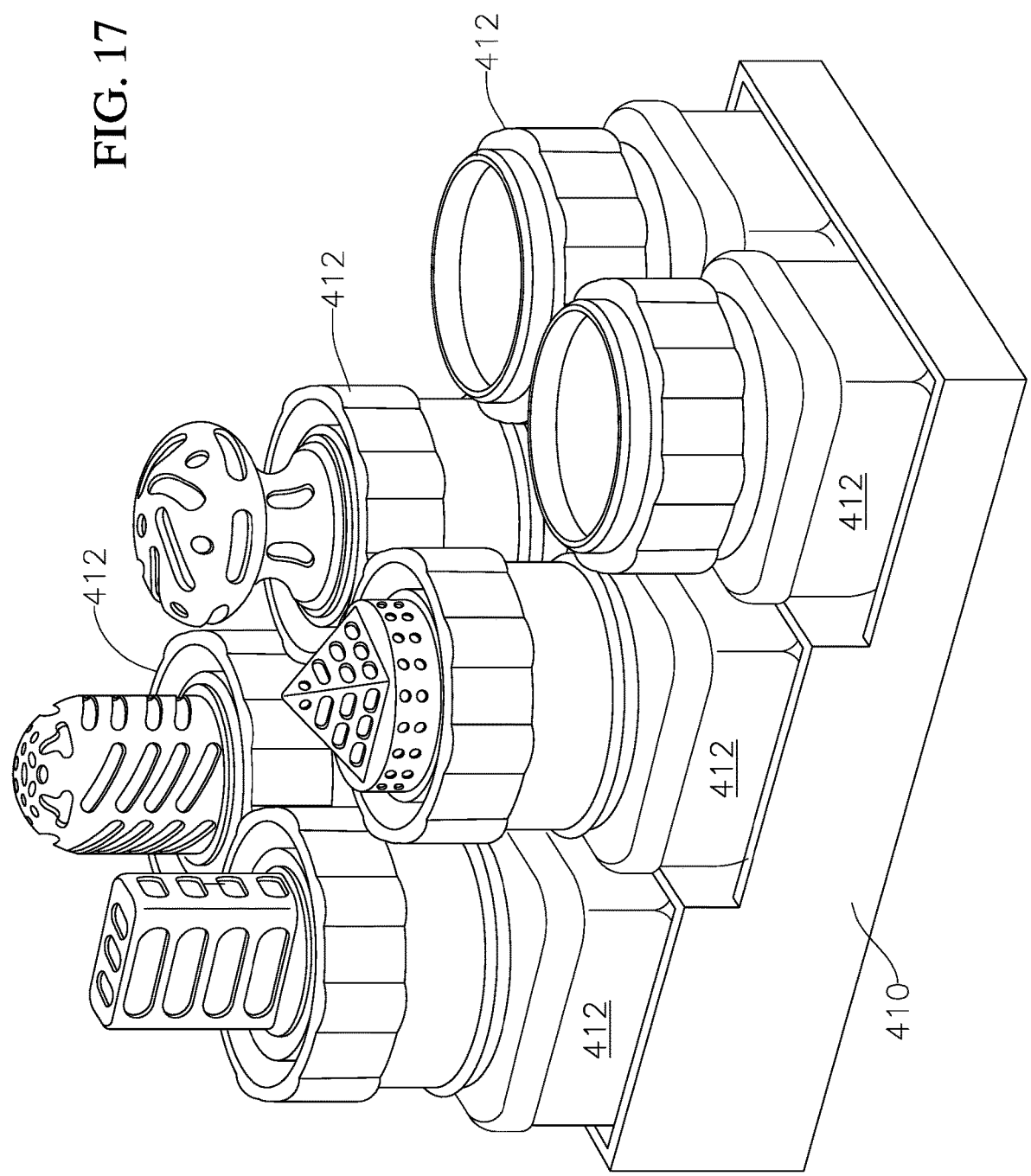
FIG. 17 shows a kit, including a plurality of scent dispensers/absorbers arranged on a stand with some of the scent dispensers/absorbers being shown in "on" conditions and some of the scent dispensers/absorbers being shown in "off" conditions.

FIG. 17 shows a pack or kit which includes a rack-like stand 410 configured to store a plurality of scent dispensers/absorbers 412, some of which are shown in "on" conditions and others of which are shown in "off" conditions. In use, the various scent dispensers/absorbers 412 can incorporate scents associated with various times of day. Some or all of the scent dispensers/absorbers 412 might even be equipped with means to play sounds associated with the scents to be dispensed.

In an embodiment, the stand 410 of FIG. 17 and/or similar displays could be used as part of a broader system and/or method to provide desirable scents to a user in the form of a repository (i.e., library) of replaceable and interchangeable scent cartridges (not shown), such as scent cartridges 20, 120. In an embodiment, such replaceable and interchangeable scent cartridges could be provided on a per unit basis, or as part of a subscription service, as replacements for existing scent cartridges, or they could contain different scents. In an embodiment, the repository could have a replenishable stock (e.g., a seasonally-varying selection) of interchangeable and/or replaceable scent cartridges, with new scents being provided over time by the repository (i.e., scent library) itself, or by third parties selling their own scent inserts or cartridges through the scent library or otherwise. In an embodiment, the repository could be organized (physically or categorically) into a plurality of sub-categories, each being associated with different activities (e.g., study aide scents, holiday scents, anxiety relief scents, soothing scents, video call scents, meeting scents, desk work scents, etc.). The interchangeable scent cartridges could also tie into the so-called wellness movement. In an embodiment, a subscription service could also be associated with a given sub-category (e.g., providing different scents from the sub-category over time). In another embodiment, interchangeable and replaceable scent cartridges could be supplied to a user randomly (i.e., without the user's prior knowledge of the scents provided). Alternatively, a known scent could be automatically provided to a user on a periodic basis as a "refill."

In an embodiment, the replaceable and interchangeable scent cartridges could be provided in combination with replacement cages that would be essentially identical to cage 18 (see, for example, FIGS. 2-4). The replacement cages of such a combination could be distributed from the scent library together with an associated interchangeable and replaceable scent cartridge (e.g., with the interchangeable and replaceable scent cartridge lodged inside the replacement cage), thereby forming a sub-assembly or subcombination. For a user's convenience, the resulting combination or subcombination could be kept in one piece to be selectively attached to, for instance, the lid 12 of scent/dispenser absorber 10 (see, for example, FIGS. 2-4).

In other embodiments, the interchangeable and replaceable scent cartridges would not be associated with a replacement cage 18 and would instead be adapted to be swapped into the cage 18 of a user's previously purchased scent dispenser/absorber 10. In one embodiment, this could be achieved by removing the cage 18 from the lid 12, removing the previous scent cartridge 20 or replaceable and interchangeable scent cartridge (if any), optionally disinfecting the cage 18, inserting a new interchangeable and replaceable scent cartridge 20 and reattaching the cage 18 to the lid 12. In another embodiment, the interchangeable and replaceable scent cartridge 20 could slide into and out of the cage 18, or it could be inserted via a door in the cage 18 as described hereinabove.

The interchangeable and replaceable scent cartridges, whether provided alone or in combination with a replacement cage 18, could be adapted for use with scent dispenser/absorber 10, which itself could be used individually or as a member of a family of scent dispensers/absorbers. In an alternate embodiment, a display similar to the rack 410 of FIG. 17 could be used to hold interchangeable and replaceable scent cartridges when they are not in use, provided the individual compartments of the rack are modified to seal scent molecules therein. The rack and/or its compartments could be labeled or have indicia associated with specific scents, so that a user could quickly see where the various scent-specific scent cartridges or cartridge/cage combinations are stored.

In some embodiments, scent cartridges 20, 120, or the interchangeable and replaceable scent cartridges could be used with associated containers. These containers could, for example, be specially adapted to seal scent molecules inside, thereby maintaining the integrity of the interchangeable and replaceable scent cartridges. In an embodiment, these containers would house the interchangeable and replaceable scent cartridge(s) during transit to an end user or other distribution point, the containers being specially adapted to retain scent molecules while being inert thereto. Furthermore, such shipping containers could serve a dual function by providing the end user with a handy storage mechanism for their interchangeable and replaceable scent cartridges when they are not in use. In use, multiple shipping containers could be adorned stylistically and then placed in a rack/base, leading to an arrangement similar to that shown in FIG. 17. In this manner, a user can accumulate his or her own collection of scents from which they can select at their convenience for use in connection with scent dispenser/absorber 10. Alternatively, an array of scent dispensers/absorbers similar to scent dispenser/absorber 110 could constitute the arrangement of FIG. 17.

Figure 13:
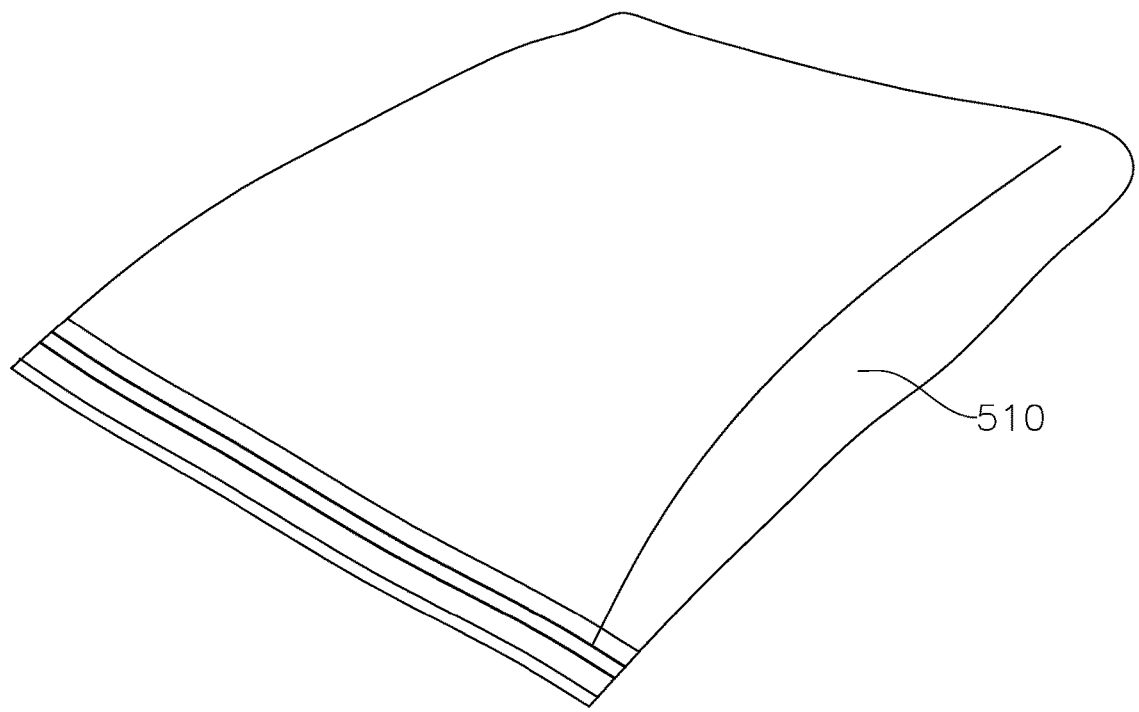
FIG. 13 is a perspective view of a package useful for storing and shipping scent cartridges, such as those used in connection with the various embodiments of the present invention illustrated in FIGS. 1-12.

An alternative packaging specially adapted for shipping scent cartridges is shown in FIG. 13, which depicts a resealable foil bag 510 whose inner surface is adapted to be inert to any reaction with respect to scent molecules of, for instance, scent cartridges 20, 120. The foil bag 510 (e.g., the Static Shielding Bag 1000 series sold by SCS) thereby functions to eliminate losses and to preserve the potency of scent for the eventual user. The size and shape of the foil bag 510 can be chosen to accommodate one or more scent cartridges having a variety of different sizes and shapes, such as those depicted in FIGS. 18-20 and 21-23, respectively.

Figure 18:
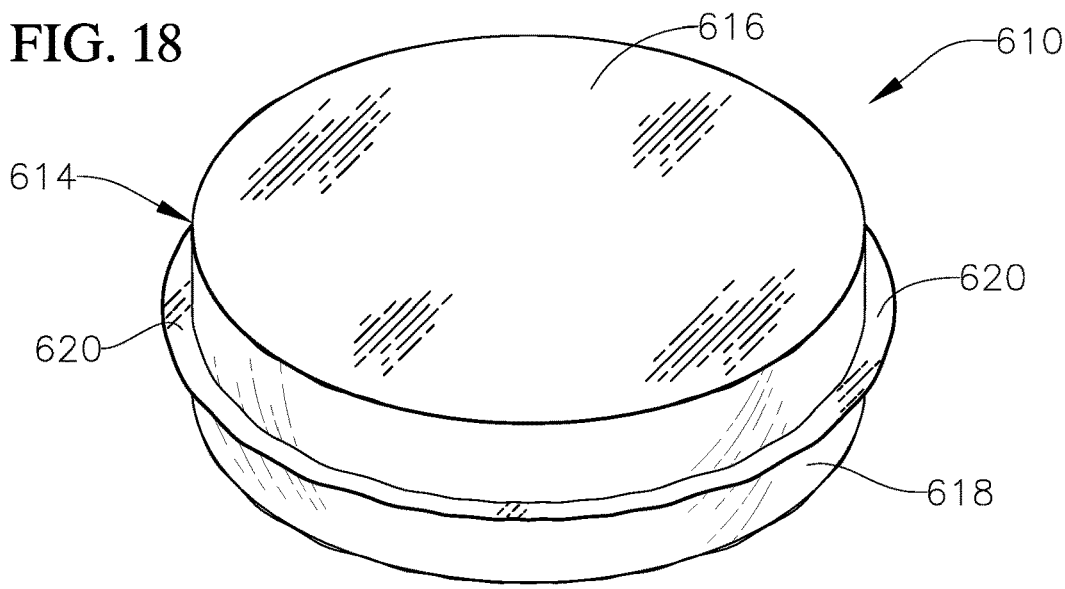
FIG. 18 is a top perspective view of an alternate scent cartridge made in accordance with an embodiment of the present invention.
Figure 19:
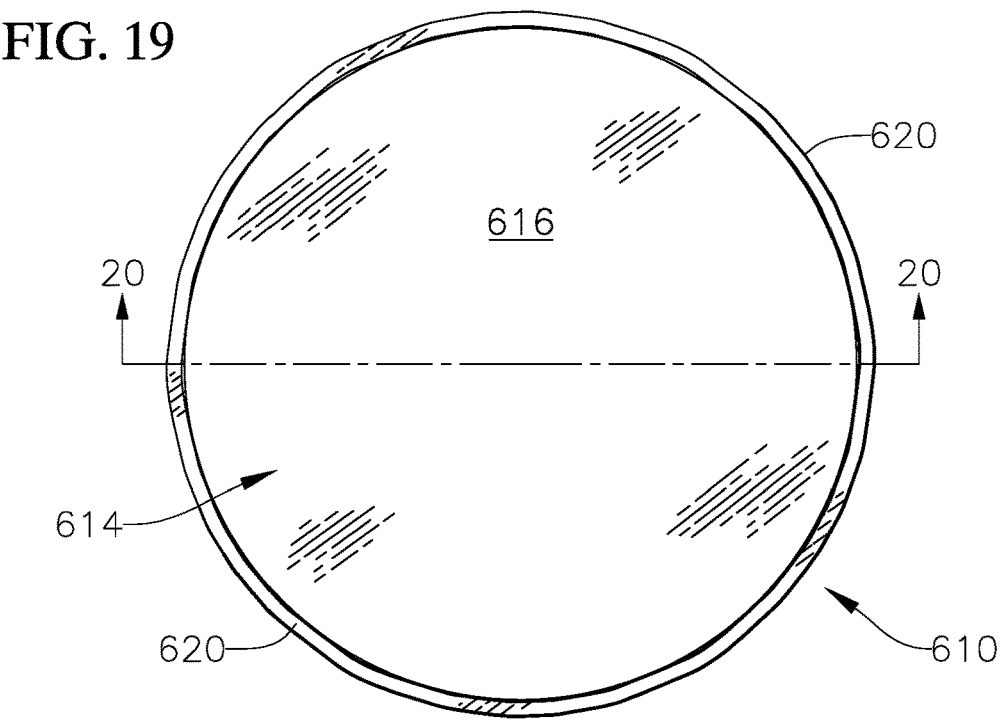
FIG. 19 is a top plan view of the scent cartridge of FIG. 18.
Figure 20:
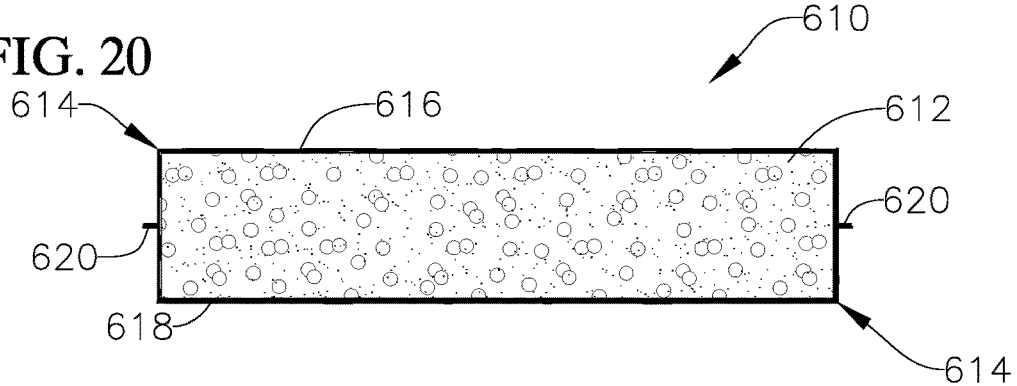
FIG. 20 is a lateral cross-sectional view of the scent cartridge of FIG. 19 taken along section line 20-20.

With reference to FIGS. 18-20, there is shown a scent cartridge or insert 610 having a round, disc-like shape. The scent cartridge 610, like the various scent cartridges disclosed hereinabove, but especially the one disclosed in conjunction with FIGS. 11 and 12, includes an inner core of a reticulated, hydrophilic composite material 612 (see FIG. 20) and an outer skin made from a heat-sealable, thermoplastic membrane 614. In the embodiment depicted in FIGS. 18-20, the thermoplastic membrane 614 is formed by heat-sealing a pair of circle-shaped sheets 616, 618 together such that they form seal 620, while enveloping the composite material 612 in the manner described above in conjunction with FIGS. 11 and 12, for example.

Figure 21:
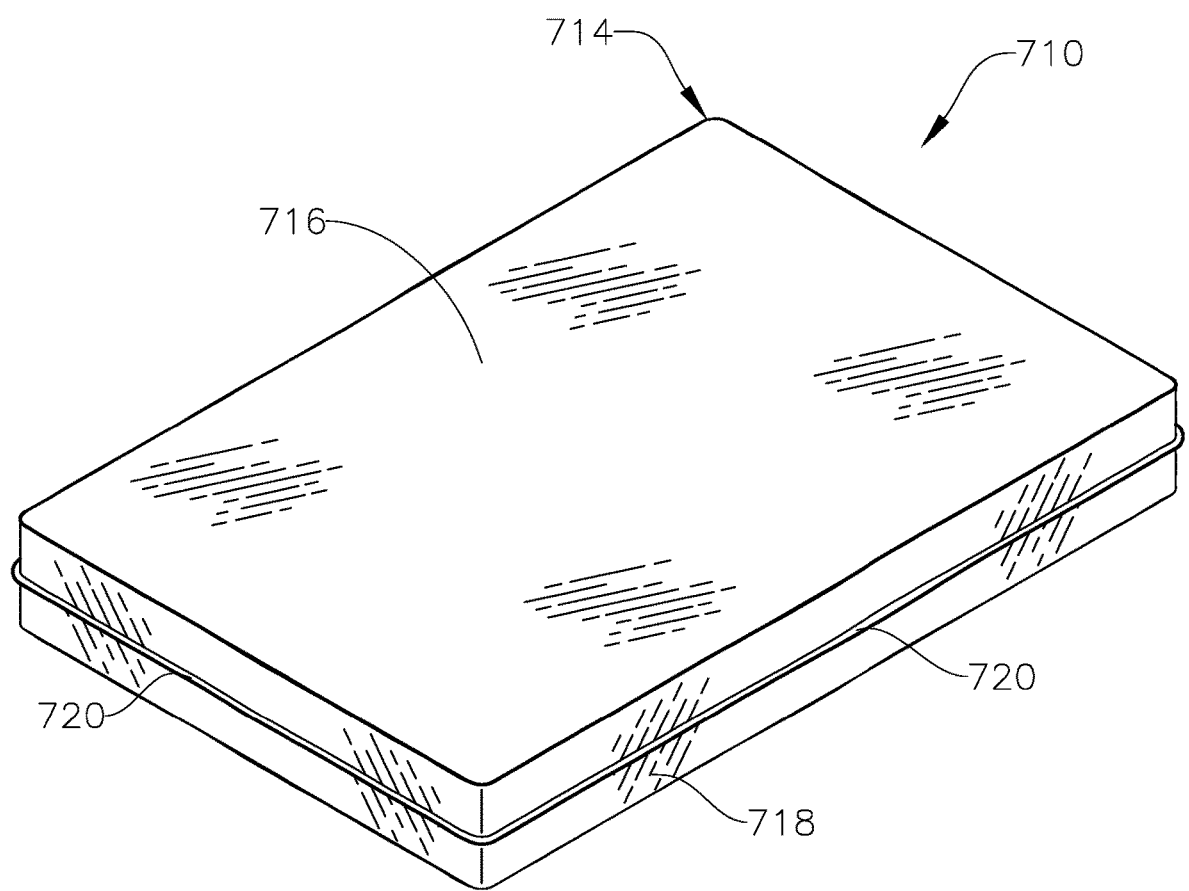
FIG. 21 is a top perspective view of another alternative scent cartridge made in accordance with an embodiment of the present invention.
Figure 22:
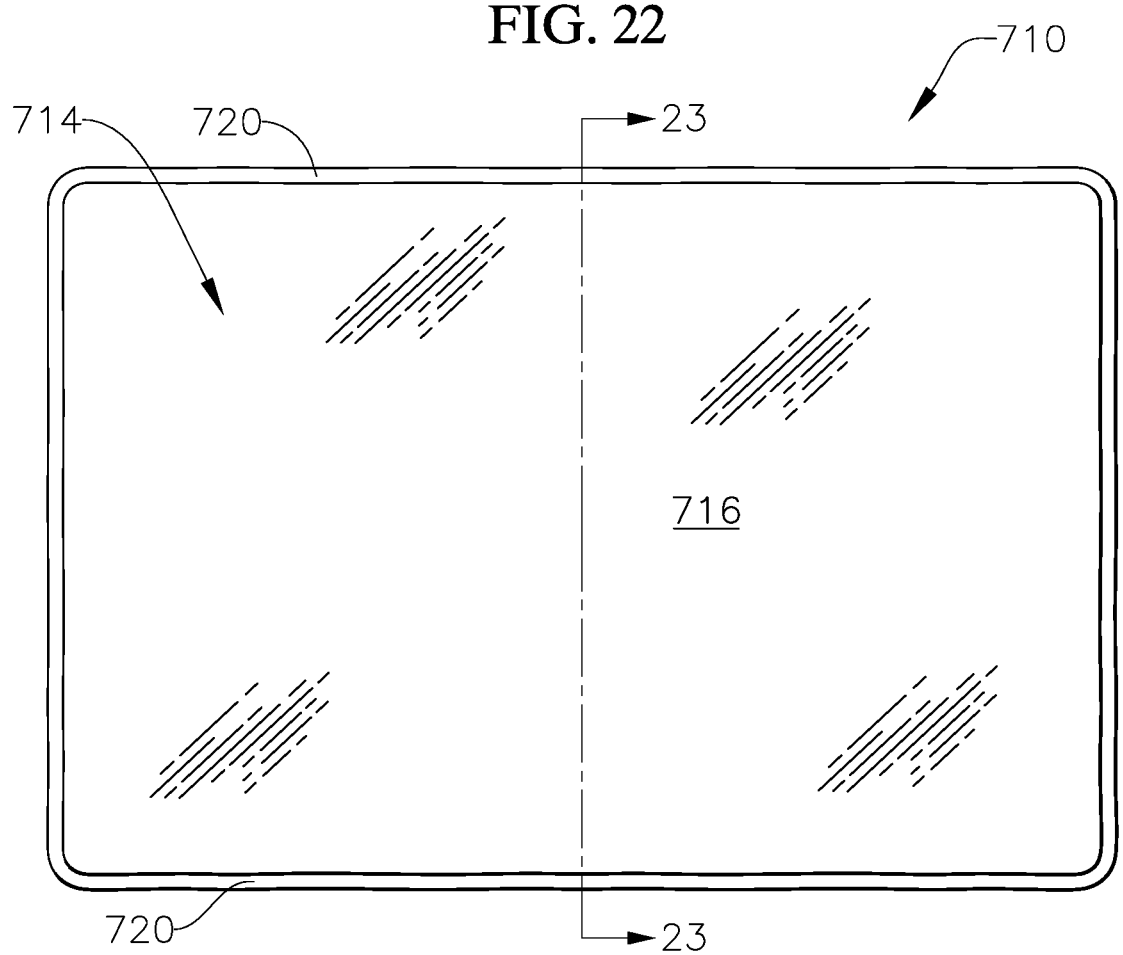
FIG. 22 is a top plan view of the scent cartridge of FIG. 21.
Figure 23:
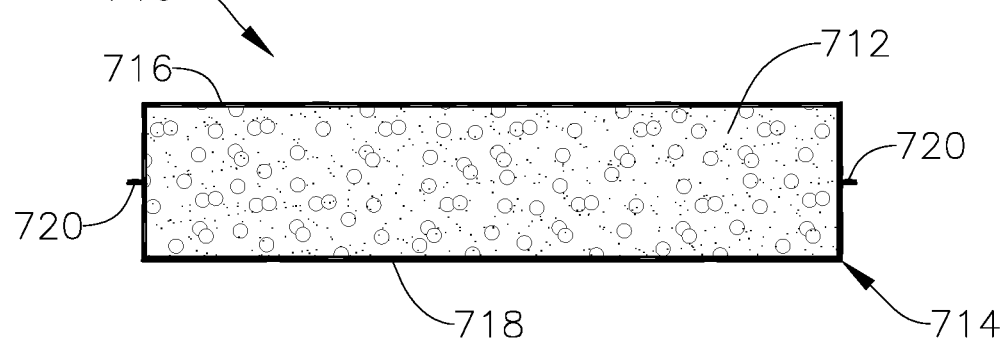
FIG. 23 is a lateral cross-sectional view of the scent cartridge of FIG. 22 taken along section line 23-23.

Referring now to FIGS. 21-23, there is shown a scent cartridge or insert 710 having a rectangular, block-like shape. Like the scent cartridge 610, the scent cartridge 710 includes an inner core of a reticulated, hydrophilic composite material 712 (see FIG. 23) and an outer skin made from a heat-sealable, thermoplastic membrane 714. In the embodiment depicted in FIGS. 21-23, the thermoplastic membrane 714 is formed by heat-sealing a pair of rectangle-shaped sheets 716, 718 together such that they form seal 720, while enveloping the composite material 712 in the manner described above in conjunction with FIGS. 11 and 12, for example.

Figure 28:
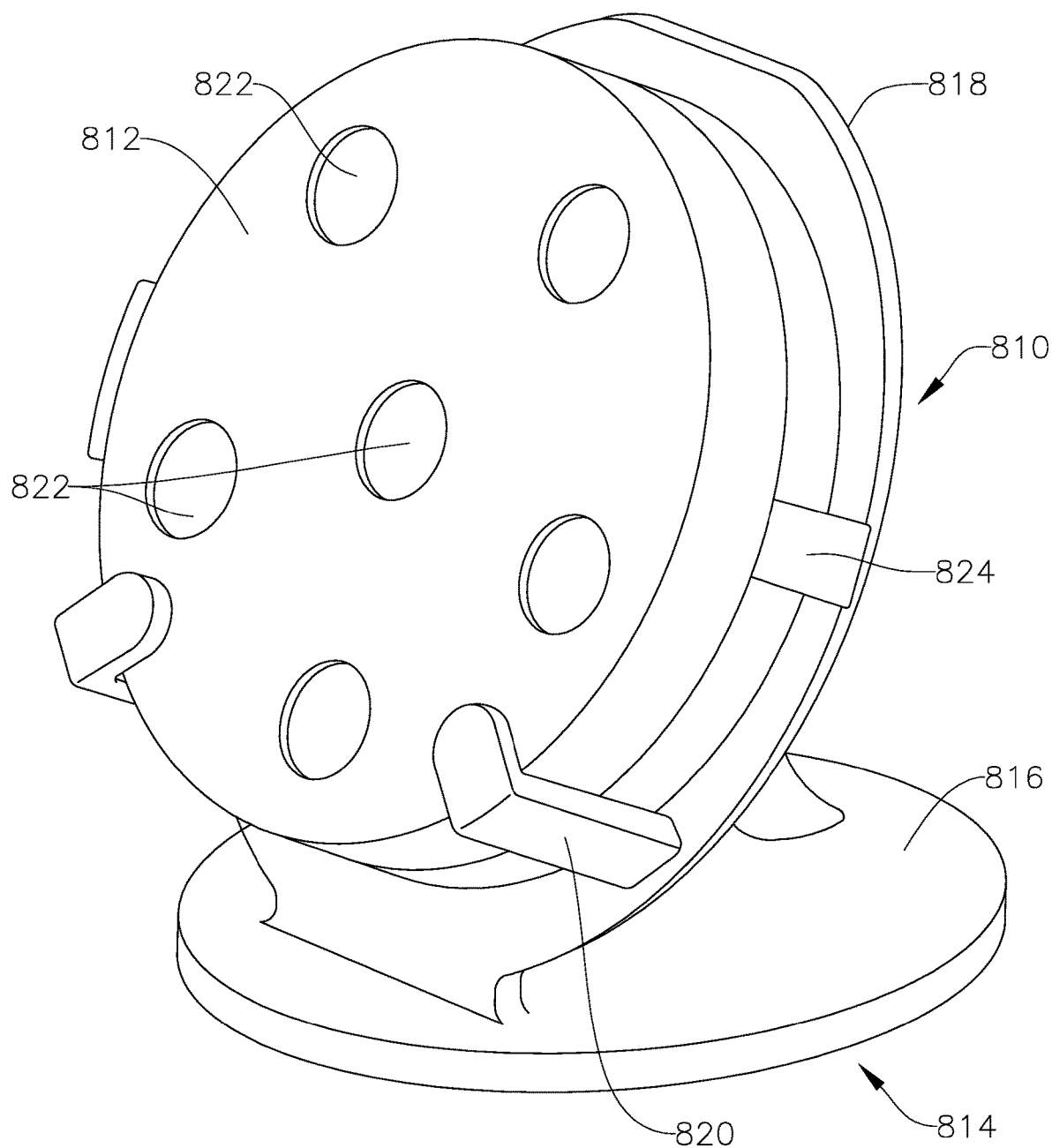
FIG. 28 is a perspective view of a scent dispenser/holder combination, the scent dispenser being shown in an "on" position in accordance with an embodiment of the present invention.
Figure 29:
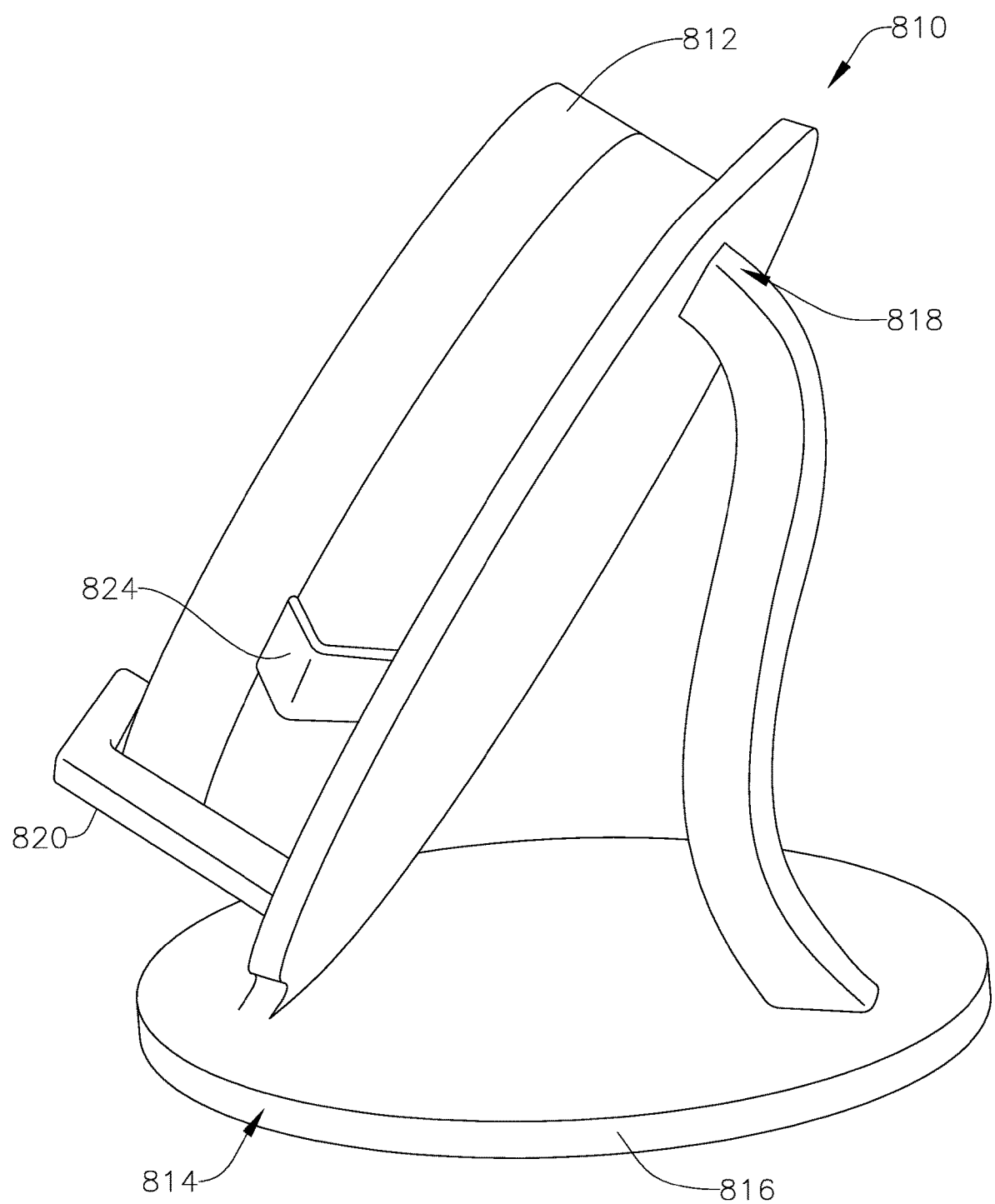
FIG. 29 is a side perspective view of the scent dispenser/holder combination shown in FIG. 28.
Figure 30:
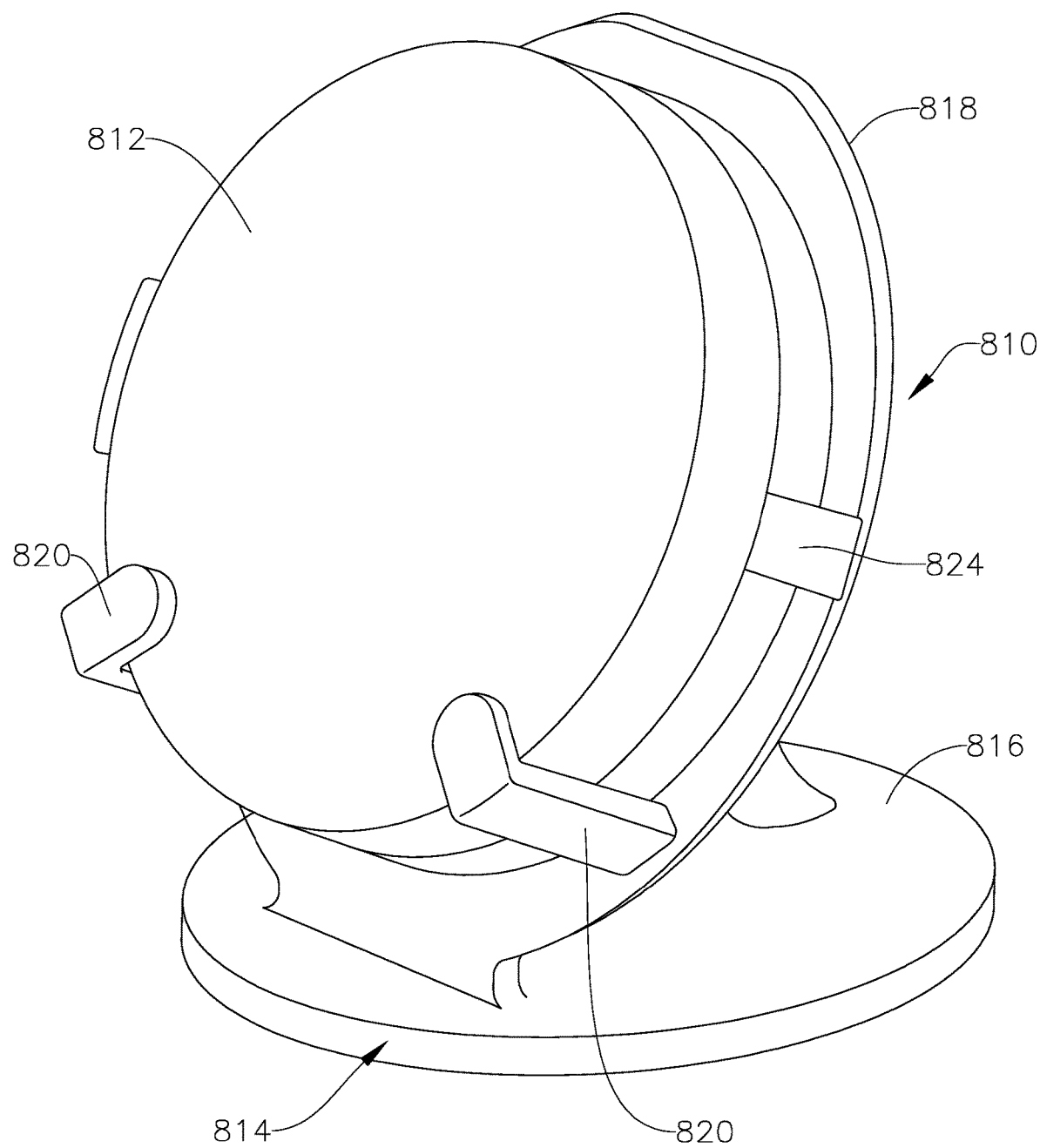
FIG. 30 is a perspective view of the scent dispenser/holder combination of FIGS. 28 and 29, the scent dispenser being shown in an "off" position in accordance with an embodiment of the present invention.

FIGS. 28-30 show various views of a scent dispenser/holder combination 810, which includes a scent dispenser 812, which can be loaded with one of the inventive scent cartridges described above, mounted on a stand 814. Stand 814 includes a base 816 and a cradle 818 angled with respect to base 816 (see, especially, FIG. 29). Cradle 818 includes fingers 820 adapted to grip scent dispenser 812 and secure it in place. Scent dispenser 812 has apertures 822 through which scent can be dispensed. In certain embodiments, scent dispenser 812 includes tabs 824 which can, for instance, be used to open the scent dispenser 812 to access its interior, such as for the purpose of changing out the scent cartridge (not shown) housed therein. FIG. 28 shows the scent dispenser 812 in an "on" position, wherein its apertures 822 are exposed to open air and scent can be freely dispensed. On the other hand, FIG. 30 shows the scent dispenser 812 in an "off" position, wherein the scent dispenser 812 is placed face-down on stand 814 by a user, thereby blocking the apertures 822 and preventing the egress of scent.

Figure 31:
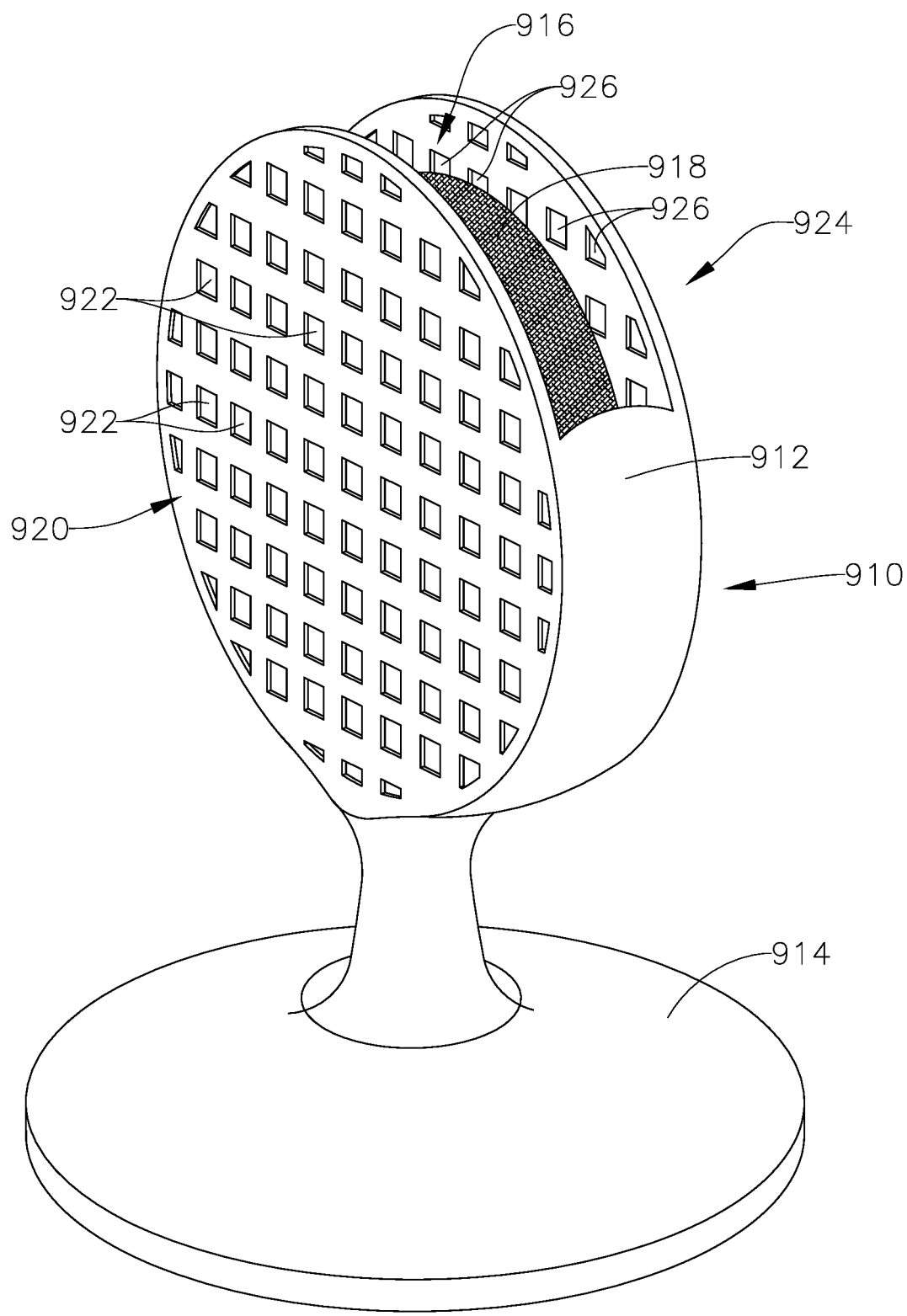
FIG. 31 is a perspective view of an alternate scent dispenser/holder combination in accordance with an embodiment of the present invention.

FIG. 31 shows an alternate "vertical" scent dispenser/holder combination 910, which includes a cradle 912 and a stand 914, which can be permanently fixed together in one piece, or removably coupled from one another. Cradle 912 includes an arcuate slot 916 adapted to receive a replaceable scent cartridge 918, which can be selectively removed and replaced as needed. Scent cartridge 918 can be the same as one or more of the scent cartridges described hereinabove in accordance with various embodiments of the present invention. Cradle 912 includes a front face 920 having front openings 922 and a rear face 924 having rear openings 926. Compared to the embodiment of FIGS. 28-30, which has a uni-directional configuration for emitting scents, scent dispenser/holder combination 910 has a "multi-directional" scent emitting configuration. For instance, scent can exit through front openings 922, rear openings 926 and/or arcuate slot 916.

In the embodiment depicted in FIG. 31, the width of arcuate slot 916 is selected to accommodate a single scent cartridge 918. However, in alternate embodiments, this width can be adjusted, for instance, to accommodate more than one scent cartridge. If all cartridges contain the same scent, the strength of that scent may be increased depending upon the number of cartridges employed. In an alternate embodiment, two or more cartridges containing different scents could be loaded into cradle 912. For instance, a first scent could be diffused through front openings 922, a second scent could be diffused through rear openings 926, and a mixture of the first and second scents could be diffused through arcuate slot 916. In other embodiments, front face 920 or rear face 924 could be void of its associated openings (i.e., front openings 922 and rear openings 926, respectively).

Examples: Experimental Validation

Figure 24:
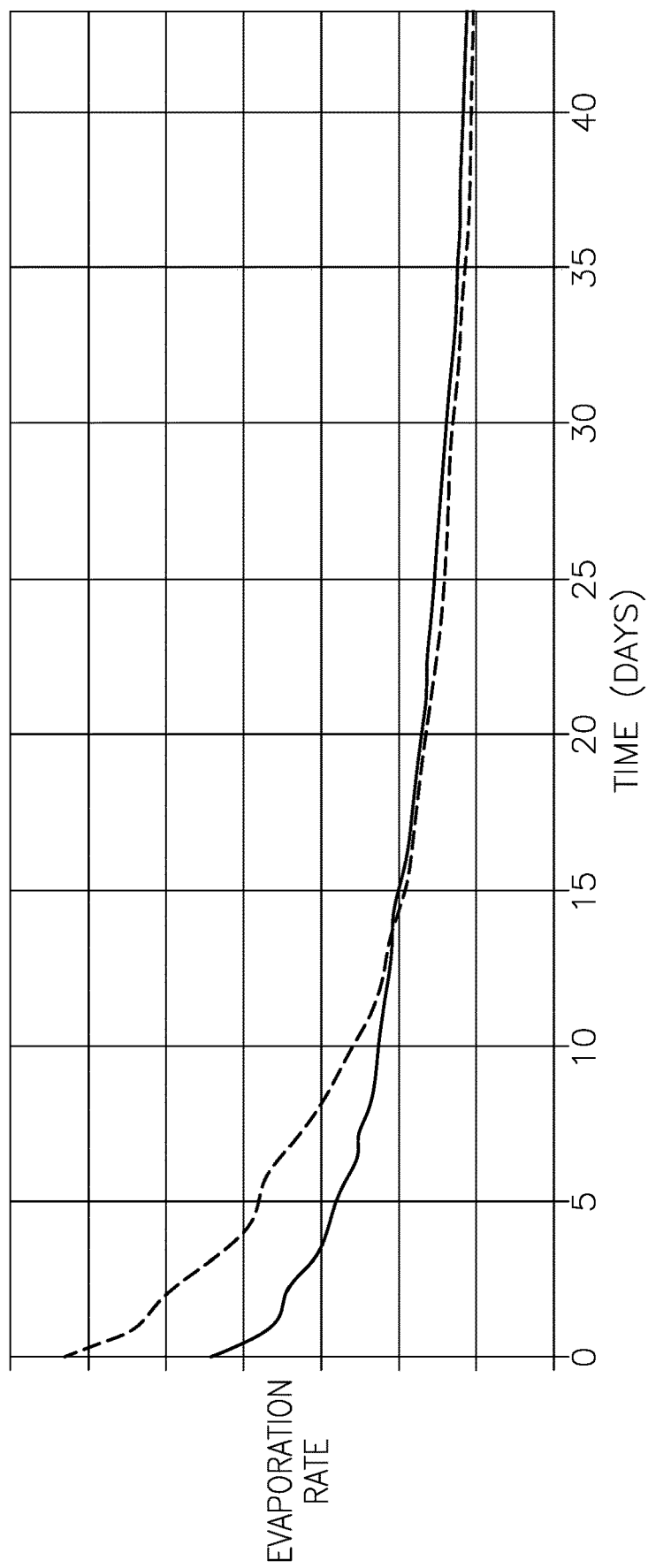
FIG. 24 is a graph illustrating diffusion curves in accordance with an embodiment of the present invention utilizing a particular scent.

FIG. 24 is a graphical representation of diffusion curves comparing the scent insert of the present invention (solid line) with a commercial diffusion-type air freshener. For comparison, the scent diffusion curve of the present invention has been multiplied by a factor of three, while the compared product had an initial mass eleven times larger than that of the scent insert made in accordance with an embodiment of the present invention. In this test, the inventive insert had a ratio of 1.85 grams of scent per gram of the insert. At the conclusion of this test, the ratio was 1.65. The samples were carrying equivalent scents.

Figure 25:
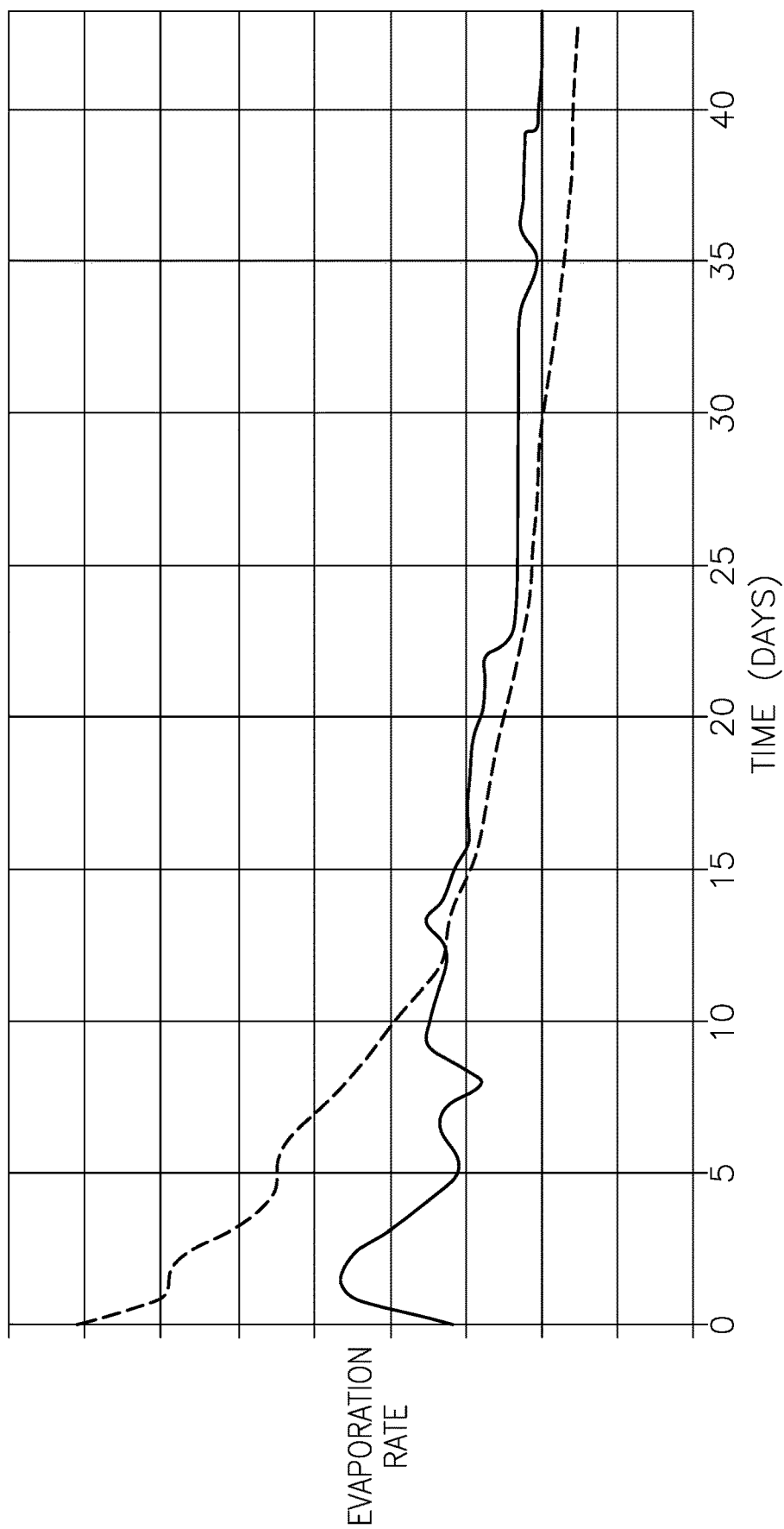
FIG. 25 is a graph illustrating diffusion curves in accordance with an embodiment of the present invention utilizing a different scent.

FIG. 25 is a graphical representation of diffusion curves comparing the scent insert of the present invention (solid line) with a commercial diffusion-type air freshener for a different scent. For comparison, the scent diffusion curve of the present invention has been multiplied by a factor of eight, while the compared product sample had an initial mass fifteen times larger than that of the scent insert made in accordance with an embodiment of the present invention. In this test, the inventive insert had a ratio of 0.78 grams of scent per gram of the insert. At the conclusion of this test, the ratio was 0.72. The samples were carrying equivalent scents.

Figure 26:
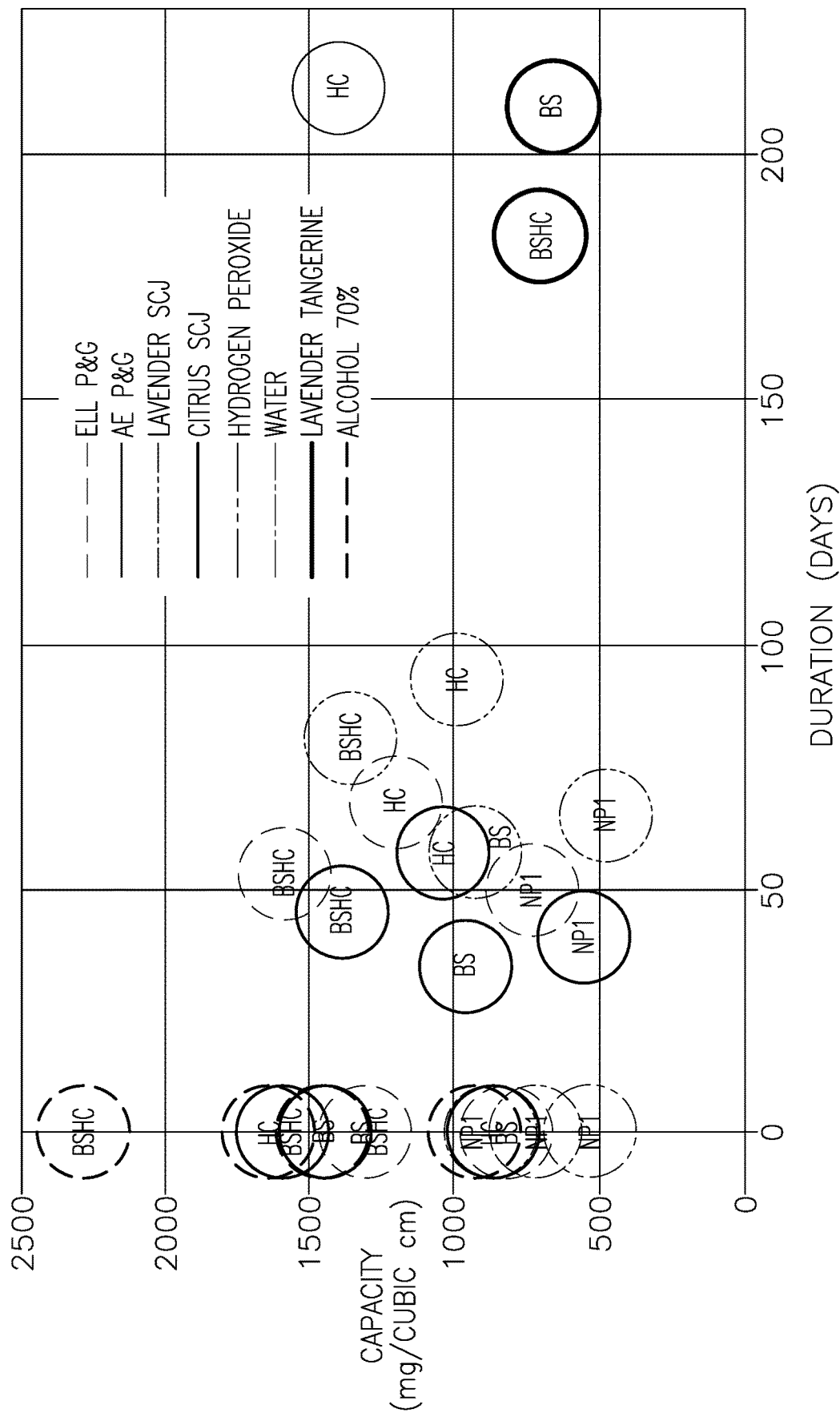
FIG. 26 is a graphical summary characterizing the performance of various hydrophilic scented materials relative to their pore sizes and densities.

FIG. 26 illustrates the performances of various hydrophilic scented materials. This chart offers a compilation of data showing the impacts of pore size and density of the hydrophilic core material when used with various odorants as well as water and alcohol. No enclosing membrane was present during these tests. The circles labeled NP1 are constructed with a typical known process. The circles labeled BSHC were a thinner material with greater pores per inch and higher density of hydrophilic material compared to the NP1 material. The circles labeled BS were a thinner material with greater pores per inch but having the typical density of the NP1 hydrophilic material. The circles labeled HC were the typical material NP1 but with higher density hydrophilic material.

Figure 27:
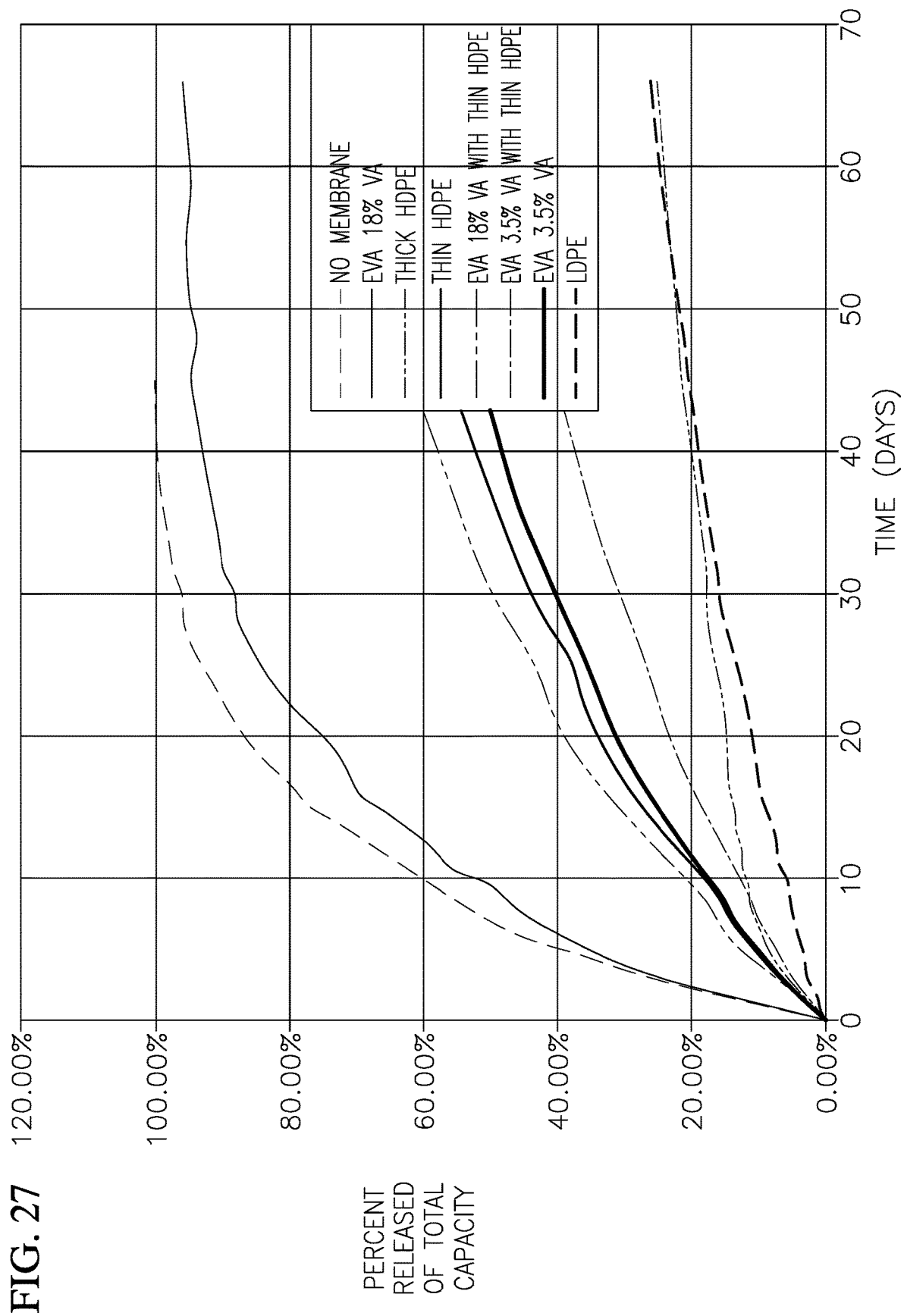
FIG. 27 is a graph illustrating release of scent over time for different membrane materials in accordance with embodiments of the present invention.

FIG. 27 shows the effect of selecting various membrane materials for the release of scent over time. The tests were conducted with a commercial oil formulation as the scent. It should be noted that this formulation was not optimized for diffusion in the tested materials, foam or membranes. Across all categories, relatively linear diffusion characteristics were seen for approximately the first 40% of scent emitted. The data demonstrate that high vinyl acetate concentrations in EVA and/or thinner layers increase diffusion rate and reduce active life. In contrast, lower vinyl acetate concentrations in EVA and/or thicker layers decrease diffusion rate, while increasing active life. In this manner, the scent dispensing parameters can be modulated depending on the intended application.

Many, if not all, of the scent-dispensing devices disclosed herein can be adapted for use in connection with smell retraining therapy, which typically involves the utilization of four specific scents, namely, "clove," "rose," "lemon," and "eucalyptus." The clinically recommended protocol calls for a patient to smell each of these four scents for fifteen seconds twice a day for several weeks to several months. While many, if not all, of the scent-dispensing devices disclosed herein can be adapted for use as a smell (i.e., olfactory) retraining aid, the scent dispensers disclosed in aforementioned U.S. Pat. No. 8,544,766 are especially adapted for such use by providing them in the form of a kit containing one or more sets of four scent dispensers. Each set would include a scent dispenser containing a corresponding one of the scents recommended for smell retraining therapy. In other words, and by way of example, such a kit would include: (i) a scent dispenser provided with an essential oil having a "clove" scent, (ii) a scent dispenser provided with an essential oil having a "rose" scent, (iii) a scent dispenser provided with an essential oil having a "lemon" scent, and (iv) a scent dispenser provided with an essential oil having a "eucalyptus" scent. A user following the aforementioned smell retraining protocol could then diffuse these four scents in a dry air formulation without any appreciable adulteration of the diffused scent.

Reference will now be made to the exemplary embodiments of the present invention illustrated in FIGS. 32-37 and described in connection therewith. Wherever practicable, similar or like reference numbers may be used in the figures and may indicate similar or like functionality. The figures depict the exemplary embodiments of the present invention for purposes of illustration only. One skilled in the art will readily recognize from the following description that alternative embodiments of the structures and methods illustrated in FIGS. 32-37 may be employed, without departing from the objects of the invention described hereinabove.

Figure 32:
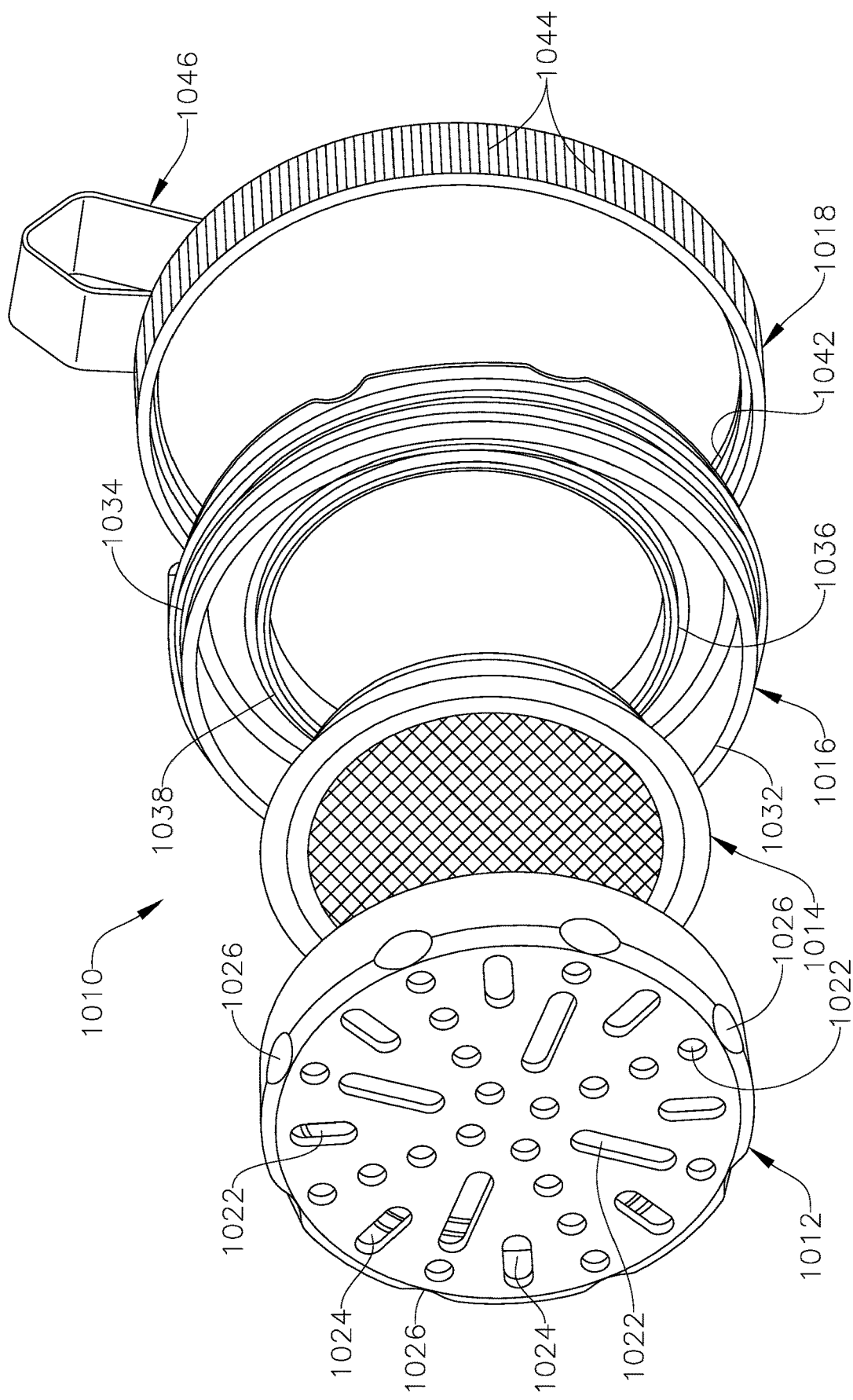
FIG. 32 is an exploded view of a scent dispenser/absorber constructed in accordance with an exemplary embodiment of the present invention, the scent dispenser/absorber being shown in an "on" (i.e., scent dispensing/absorbing) condition or position.
Figure 33:
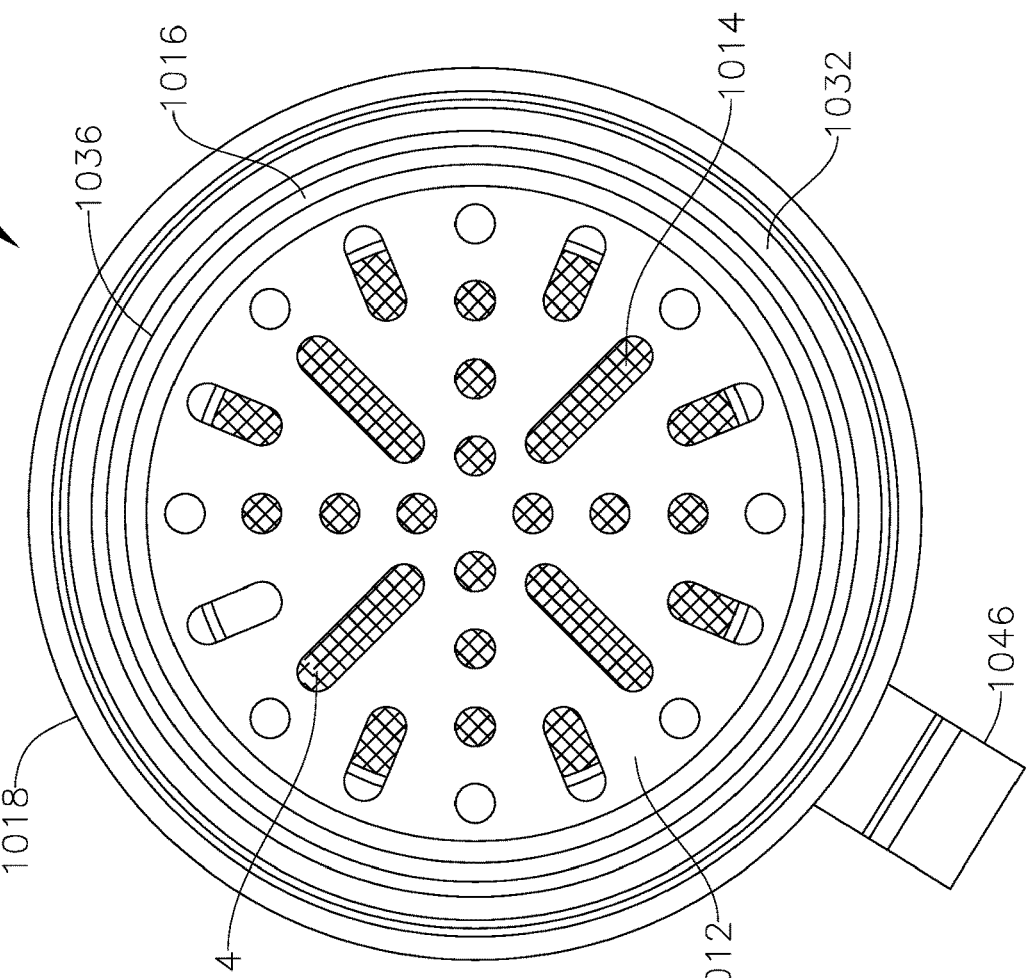
FIG. 33 is a front perspective view of the scent dispenser/absorber of FIG. 32 in its "on" condition.
Figure 34:
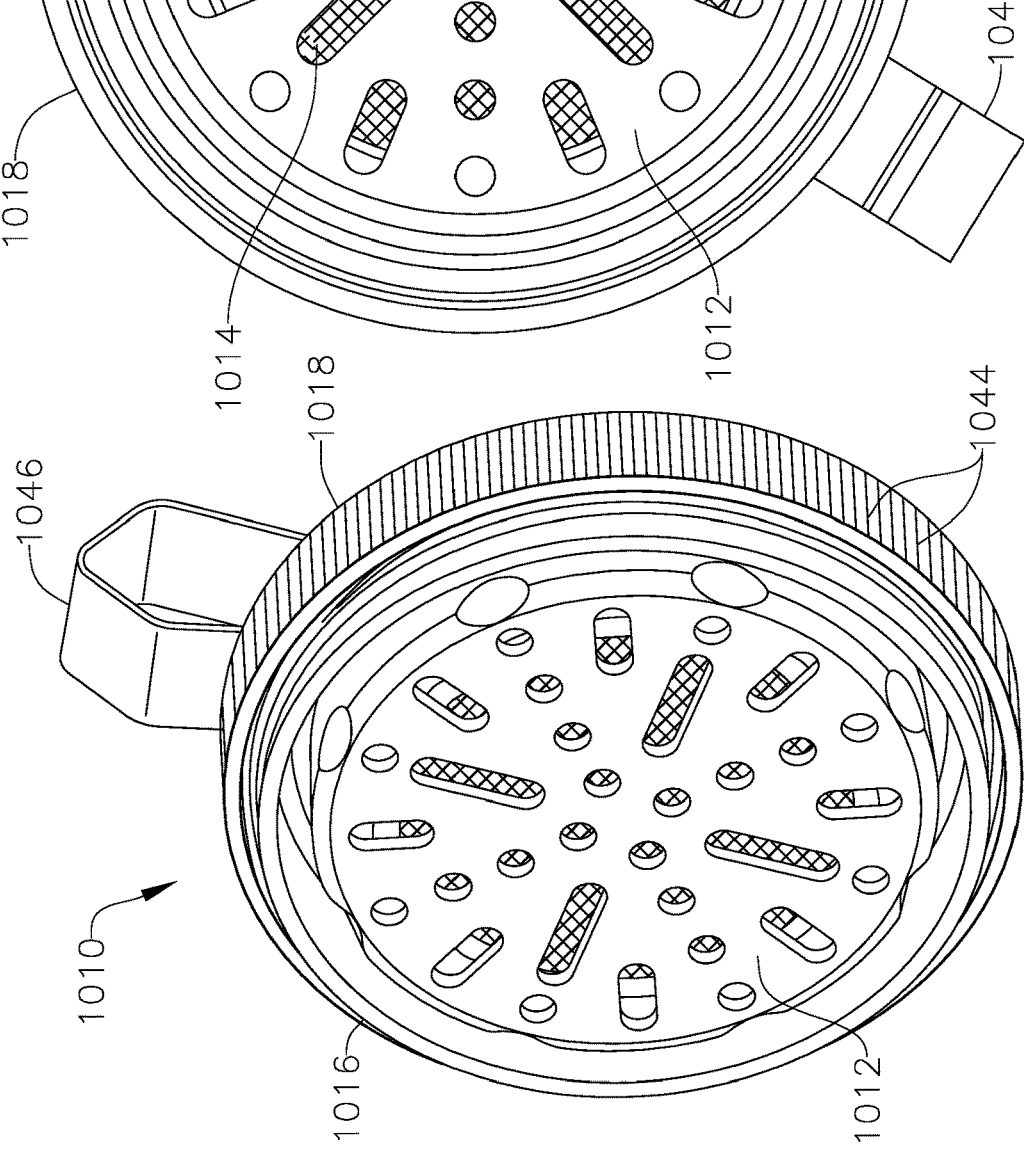
FIG. 34 is a plan view, looking from the front, of the scent dispenser/absorber of FIG. 33.
Figure 35:
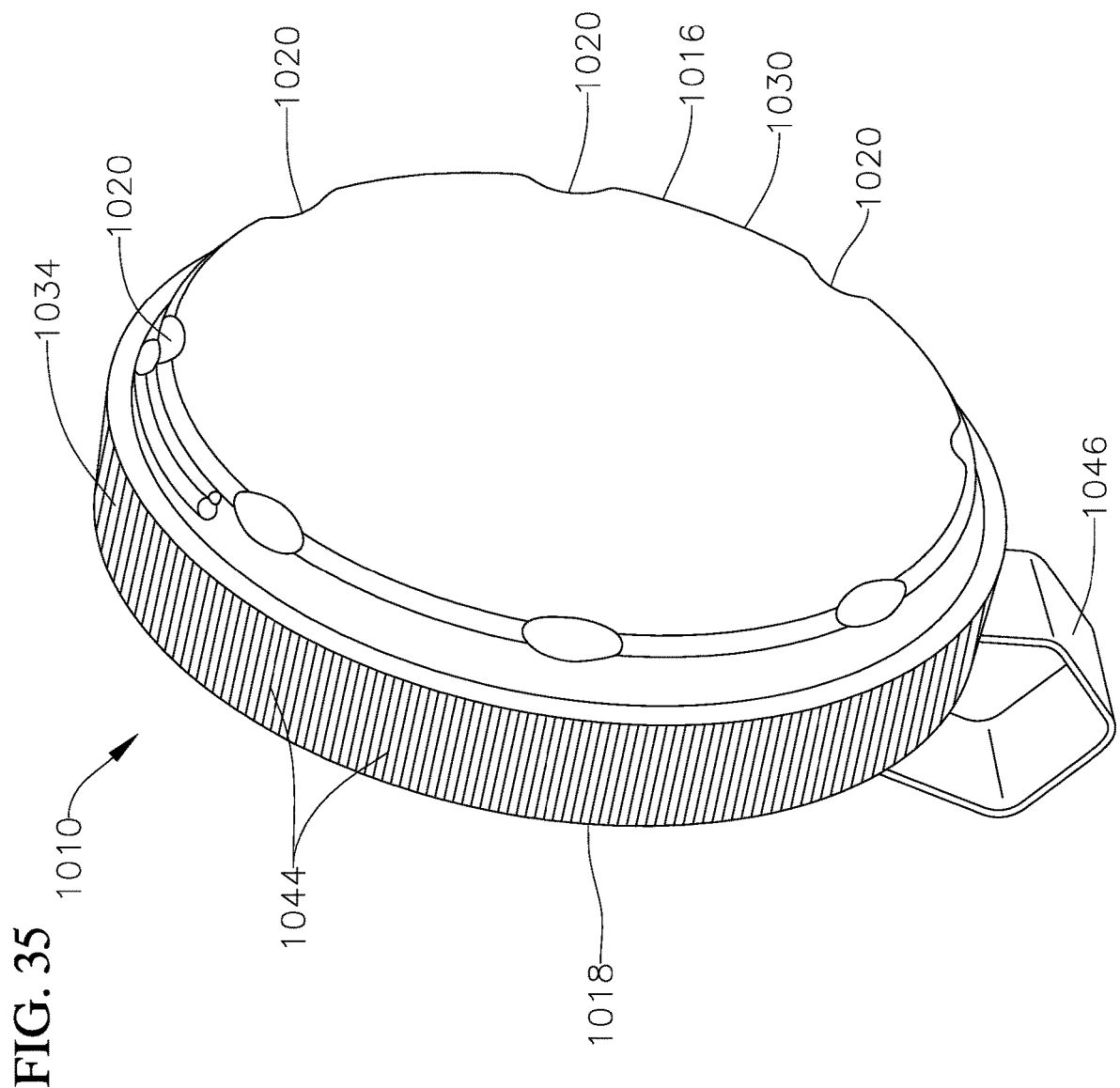
FIG. 35 is a rear perspective view of the scent dispenser/absorber of FIG. 32 in an "off" (i.e., non-dispensing/non-absorbing) condition or position.
Figure 37:
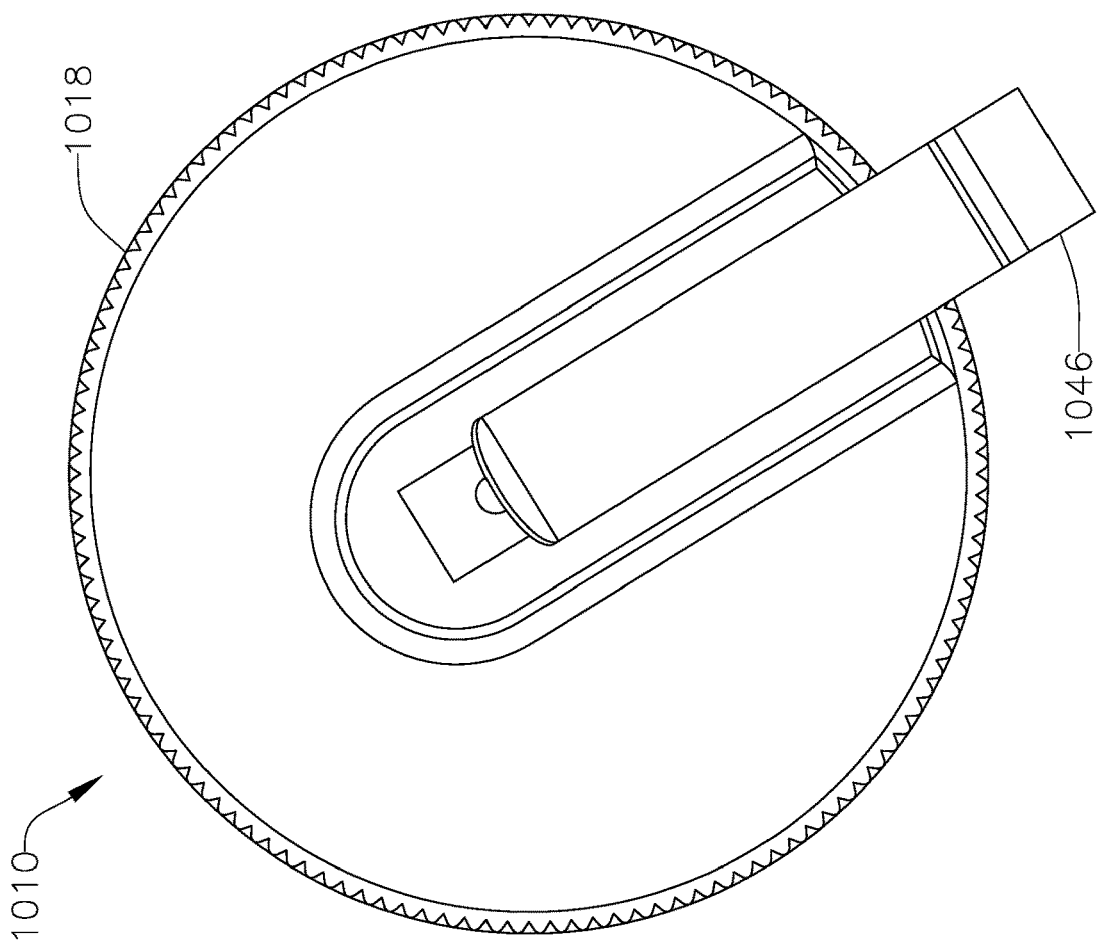
FIG. 37 is a plan view, looking from the front or rear, of the scent dispenser/absorber shown in FIGS. 32-36.
Figure 36:
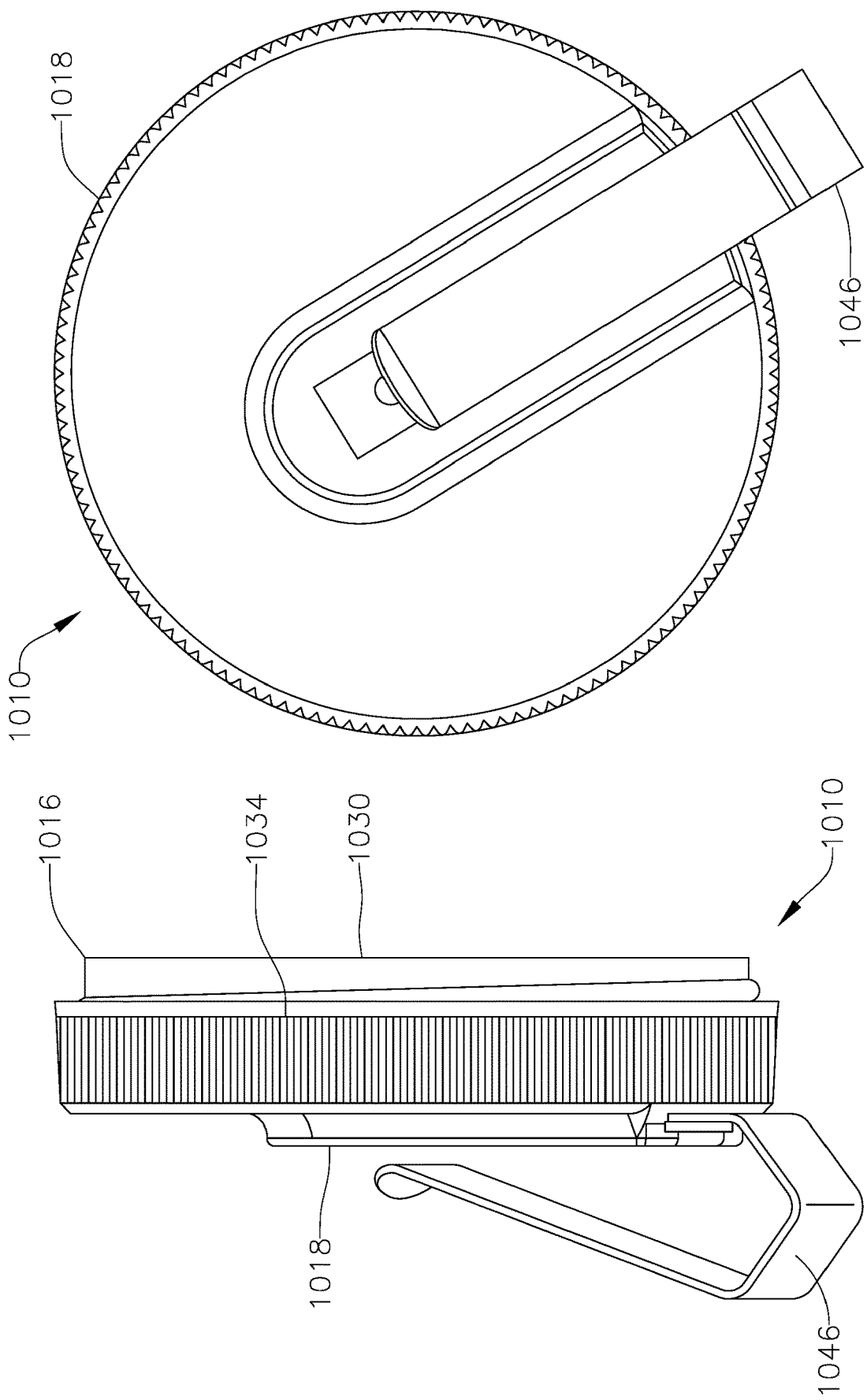
FIG. 36 is a side elevational view of the scent dispenser/absorber of FIG. 35.

Referring now to FIG. 32, an exploded view of a scent dispenser/absorber 1010 is shown. Specifically, the parts illustrated in FIG. 32 are ordered to show their orientation when scent dispenser/absorber 1010 is in its "on" condition. Accordingly, as shown in FIG. 33, the scent dispenser/ absorber 1010 includes, as viewed from left to right, a vented cage 1012, a scent cartridge 1014, a base 1016, and a lid 1018.

When lid 1018 is removed from base 1016, which includes finger grips 1020 to facilitate such removal, scent cartridge 1014 is exposed to the environment via a plurality of vents 1022 in cage 1012. Thus, when the scent dispenser/absorber 1010 is in use in its "on" condition, the scent cartridge 1014 communicates with the outside environment via the vents 1022 in the cage 1012. In a scent-dispensing mode, the vents 1022 allow scent to migrate from the scent cartridge 1014 to the surrounding environment. Conversely, in a scent-absorbing mode, the vents 1022 allow scent to migrate from the surrounding environment to the scent cartridge 1014. For reasons to be detailed later, cage 1012 can include internal threads 1024, as well as a plurality of finger grips 1026.

Scent cartridge 1014 is adapted to be receivable in an open end 1028 of base 1016, opposite a closed end 1030 of base 1016. The base 1016 also includes an annular sidewall 1032 having external threads 1034, for purposes to be described hereinbelow. In an embodiment, closed end 1030 of the base 1016 contains a raised annular rim 1036, which includes external threads 1038 adapted to threadably mate with the internal threads 1024 of the cage 1012. This can be via a "screw-on" and "screw off" mechanism of attachment, in which case, finger grips 1026 would aid the user in attaching and detaching cage 1012 from base 1016. It should be understood that any alternate means for attaching/detaching cage 1012 from base 1016 could be employed, including snap-fit and bayonet mechanisms. Annular rim 1036 defines a compartment 1040 so that at least one scent cartridge 1014 can be locked into compartment 1040 via attachment of cage 1012 to base 1016.

It is through the disposition of lid 1018 that the scent dispenser/absorber 1010 can be changed from its off position to its on position and vice-versa. More particularly, the lid 1018 has internal threads 1042 adapted to threadably mate with an adjacent set of the external threads 1034 located proximal the open end 1028 of the base 1016, thereby removably joining the lid 1018 to the open end 1028 of the base 1016. This form of attachment would be via a "screw on" and "screw off" mechanism. To facilitate such attachment and detachment, lid 1018 can include ridges/knurls 1044 to improve a user's grip. However, the same form of joinder may be accomplished via any number of known joining methods, such as dimples, snap fits, press fits, notches, friction fits, pins, magnets, etc. Lid 1018 and/or base 1016 can be made from glass, polypropylene or related materials with similar properties.

Through removal of the lid 1018 from the open end 1028 of the base 1016, the scent-dispenser/absorber 1010 is put into its "on" position. However, for convenience, lid 1018 can be screwed onto closed end 1030 of base 1016 by mating its internal threads 1042 with an adjacent set of the external threads 1034 located proximal the closed end 1030 of the base 1016, thus providing a convenient disposition of lid 1018 while maintaining scent dispenser/absorber 1010 in its "on" condition.

As indicated above, the cage 1012 operates to secure scent cartridge 1014 within compartment 1040 of base 1016. In some embodiments, the cage 1012 and/or base 1016 can be sized and shaped to hold multiple scent cartridges holding the same scent, or different scents. For the purpose of preventing intermingling of scents, especially in the case of cartridges holding different scents, a thin, disc-like divider (not shown) can be removably placed between adjacent scent cartridges. Such a divider would ideally be impermeable to scent molecules. Removal of the divider can shift the scent dispenser/absorber 1010 from a single-scent mode to a composite mode wherein different scents are intermingled and dispensed as a customized scent. In another embodiment, the relative positioning of the cartridges can be switched to select which scent cartridge is being diffused into the environment (i.e., atmosphere). In a further embodiment, one of the scent cartridges can be adapted for a scent-diffusing mode, while another scent cartridge is adapted for a scent-absorbing mode. In such a configuration, the relative positioning of the scent cartridges can be chosen to switch the scent dispenser/absorber 1010 from a scent-diffusing mode to a scent-absorbing mode and vice-versa.

In one embodiment, the scent cartridge 1014 comprises reticulated hydrophobic polyurethane foam (Product No. RT030CHRSC1) from Ionac (Woodbridge INOAC Technical Products, 100 Carol Place, Moonachie, NJ 07074), which material provides the scaffolding for the scent cartridge 1014. It is a desirable material for the scaffolding of the scent cartridge 1014 because scent molecules only weakly interact with it. Due to the fact that polyurethane molecules are not volatile at typical pressures and temperatures, the odorant scent released from the scent cartridge 1014 will not be adulterated by the scaffolding (i.e., the aforementioned polyurethane foam).

To prepare the scent cartridge 1014, the foam or scaffolding material can be coated with a thin layer of prepolymer, such as Dow Chemical's HYPOL JM 5005, which can then be reacted with water molecules to form a hydrophilic polyurethane surface coating. The large hydrophilic polyurethane molecules are non-volatile and do not contribute to the scents produced. The hydrophilic polyurethane is polar in nature and has a degree of affinity for scent molecules.

As the hydrophilic polyurethane surface coating is curing, $CO_2$ out gassing results in a larger surface area. On the surface of the reticulated material, the scent molecules adhere along the hydrophilic polyurethane surface due to their polar interactions. There is a large surface area available for evaporation and a "headspace" within the material that generally contains a high level of "dry air" scented vapor. Through this process, the scent cartridge 1014 can release a high-quality representation of the original scent, while ensuring that the scent lasts a long time. Various thicknesses (e.g., ⅜") and pore sizes (e.g., 30 pores per inch) of reticulated base material are possible.

The result is that when the scent dispenser/absorber 1010 is switched to its "on" condition, as described above, a faithful iteration of the original odorant scent will be released for sampling or other purposes. In other words, the aforementioned sampling step is carried out in an environment in which essentially ambient air contains scent molecules, but no liquid. Thus, the scent dispenser/absorber 1010 allows scents to be stored, transported and sampled in a non-liquid form, the sampling being performed in a "passive" manner.

While the scent cartridge 1014 has been described with reference to a particular embodiment thereof, it should be understood by those skilled in the art that various changes may be made and equivalents may be substituted without departing from the true spirit and scope of the present invention. For instance, the scent dispenser/absorber 1010 is adapted for use with other types of scent capturing and diffusing media such as the scent cell disclosed in U.S. Patent Application Publication No. 2017/0312380 (see especially Paragraphs [0048] to [0050]), U.S. Pat. No. 8,544,766 (see especially Column 6, lines 30-59) and U.S. Pat. No.

6,617,014, all of which patent publications are incorporated herein by reference in their entireties.

In addition, many modifications may be made to the scent cartridge 1014 described herein to adapt it to a particular situation, use or application without departing from the overall objective, spirit and/or scope of the present invention. For instance, the scent cartridge 1014 could be replaced by a scent cartridge adapted to absorb and/or adsorb a volatile scented substance, while allowing the ready passage of air therethrough. In some other embodiments, the scent cartridge 1014 could contain an amount of volatile scented substance, such as those used in perfumes, for attracting game, for calming a pet, as diet aids, for aroma therapy, for medical applications, or for other uses which are known or may become known, such as providing cannabis-derived and/or hemp-derived scents, fragrances, etc. In some embodiments, the scent cartridge 1014 would be designed such that the scented substance may be added directly to the scent cartridge 1014 to replenish or change the scent.

By way of further example, the scent cartridge 1014 may be made of any material that can carry and release volatile scented substances. In some embodiments, the scent cartridge 1014 could be made of an absorbent fibrous material or closed cell foam having air passages penetrating therethrough. In other embodiments, the scent cartridge 1014 could be made of an open-cell foam that presents an appreciable ratio of surface area to volume of foam, with higher ratios typically being preferred. In such embodiments, the foam may be a hydrophilic foam or have a hydrophilic material exposed at the surfaces of its cells. Other suitable embodiments could utilize an open-cell foam composite made of substantially hydrophobic foam to provide structure to the composite and substantially hydrophilic foam exposed at the surfaces of its cells, such as the foam described in U.S. Pat. No. 6,617,014, whose disclosure is incorporated herein by reference in its entirety.

In yet other embodiments, the scent cartridge 1014 may comprise a nonwoven fibrous material substrate coated with, for example, a substantially hydrophilic foam coating which is exposed at the surface and in interstitial spaces within the nonwoven fibrous material. The interstitial spaces within the nonwoven fibrous material form air passages penetrating therethrough to allow the flow of air. Examples of suitable nonwoven fibrous materials include, without limitation, cotton, felt, silk, or combinations thereof. As will be recognized by persons of ordinary skill in the relevant art, such embodiments would be useful when the volatile scented substances employed to impart scent or alternative odor to the scent cartridge 1014 are of the types that may react with and degrade some hydrophobic foams (see, e.g., U.S. Pat. No. 8,544,766, which is incorporated herein by reference in its entirety). One possible process for producing such a scent cartridge involves contacting a substrate of nonwoven fibrous material with a prepolymer emulsion and then polymerizing or curing the emulsion. By way of further example, the substrate can be dipped or immersed in the prepolymer emulsion, which can also be applied by brushing or otherwise coating onto the substrate. In an embodiment of such a process, the substrate of nonwoven fibrous material may be provided as a sheet or block and then coated with the prepolymer emulsion, followed by polymerization or curing of the emulsion to form the substantially hydrophilic foam on the nonwoven fibrous substrate. The substrate can then be cut into appropriately sized and shaped pieces to produce the desired scent cartridge.

In other embodiments, the scent cartridge 1014 could take the form of a square patch (e.g., 1" by 1"), or any other convenient shape. As a patch, it could be covered by fabric or be bare. In certain embodiments, it could be carried in a pocket of a user's clothes, or can even be integrated into the garments themselves, whether the clothes are for a human or an animal. A main objective of such embodiments is to provide a scented element that does not wick onto the clothes themselves. By way of example, insect-repellant scents in clothes could be useful for gardeners, while anti-seasickness scents in clothes could be useful for sailors and the like. To counteract foul odors, garbage cans and/or diaper bags could be integrated with odor-combatting scents.

The scent cartridge 1014 can be constructed in accordance with still further embodiments thereof. For instance, another alternate scent cartridge arrangement is disclosed in U.S. Provisional Patent Application Ser. No. 63/028,433, which is incorporated herein by reference.

In an embodiment, the replaceable and interchangeable scent cartridges could be provided in combination with replacement cages that would be essentially identical to cage 1012. In other embodiments, the interchangeable and replaceable scent cartridges would not be associated with a replacement cage and would instead be adapted to be swapped into the cage 1012 of a user's previously purchased scent dispenser/absorber 1010. In one embodiment, this can be done by removing the cage 1012, removing the previous scent cartridge 1014 or replaceable and interchangeable scent cartridge (if any), optionally disinfecting the cage 1012, inserting a new interchangeable and replaceable scent cartridge and reattaching the cage 1012 to the base 1016.

For convenience of use, the lid 1018 includes an attachment clip 1046, which can be removable, such as via magnets on clip 1046 and/or on base 1016. This clip 1046 can allow for scent dispenser/absorber 1010 to be wearable, via attachment to garment(s), and/or to be removably attachable to sun visors on any type of vehicles (e.g., cars, boats and planes). In embodiments in which base 1016 is magnetized, the scent dispenser/absorber 1010 can also be removably coupled to a metal surface, such as on a refrigerator or in a car.

In yet another embodiment of the present invention, the inventive scent dispenser could be combined with certain scent-dispensing embodiments disclosed hereinabove. Specifically, scent dispenser/absorber 1010 of the present application could be removably coupled or permanently fixed within skirt-like ring 28 of FIGS. 1-4. In such a combination, scent dispenser/absorber 1010 could operate as described hereinabove when the scent dispenser of FIG. 1 is in a closed state, by selectively removing/replacing lid 1018. At the same time, a second scent dispensing functionality could be achieved by inverting cap 27 to activate a second scent-dispensing mode, with the same scent or a different scent as that provided by scent dispenser/absorber 1010. In the first instance (i.e., closed state), the scent cartridge 20 is housed in internal chamber 26 and scent dispenser/absorber 1010 of the present invention is external. In the second configuration (i.e., second scent dispensing functionality), scent cartridge 20 is external and scent dispenser/absorber 1010 of the present invention is housed inside internal chamber 26.

It will be understood that the embodiments described hereinabove are merely exemplary and that a person skilled in the art may make many variations and modifications without departing from the spirit and scope of the present invention. For instance, besides the "passive" embodiments described above, "active" (i.e., driven) embodiments of the present invention are also possible. Furthermore, the present invention is not necessarily limited to "dry air" embodiments. All such variations and modifications are intended to be included within the scope of the present invention.

What is claimed is:

1. Apparatus for diffusing scent, comprising a housing having an open end, a closed end opposite said open end, and an interior chamber between said open and closed ends of said housing; a replaceable, scent-diffusing cartridge positionable within said interior chamber of said housing, said scent-diffusing cartridge being adapted for non-active, dry air scent diffusion in which scent molecules can be passively emitted in non-droplet form; and invertible lid adapted for selective and sequential attachment to said open end and/or said closed end of said housing such that said scent-diffusing cartridge can be selectively isolated from and exposed to an exterior environment surrounding said apparatus, wherein said scent-diffusing cartridge is isolated from the exterior environment when said lid is in a non-inverted position and attached to said open end of said housing, and wherein said scent-diffusing cartridge is exposed to the exterior environment when said lid is in an inverted position and attached to one of said open and closed ends of said hosing; a diffuser forming a portion of a compartment configured to removably receive said scent-diffusing cartridge, said diffuser configured to allow the transmission of scent molecules therethrough to the external environment when said lid is in said inverted position, and said diffuser being detachable from said apparatus when said lid is in said inverted position to thereby permit access to said scent-diffusing cartridge for removal and/or replacement thereof, wherein said lid is attachable to said open end of said housing in said non-inverted position, in which position said compartment, said diffuser and said scent-diffusing cartridge are located entirely within said interior chamber of said housing between said lid and said closed end of said housing, and wherein said lid is attachable to said open end of said housing in said inverted position, in which position said compartment, said diffuser and said scent-diffusing cartridge are located externally of said housing.

2. Apparatus according to claim 1, wherein said diffuser is in the form of an elongated cage having a plurality of apertures configured to allow the transmission of scent molecules therethrough.

3. Apparatus according to claim 2, wherein said cage includes a flange configured to attach said cage to said lid.

4. Apparatus according to claim 3, wherein said lid includes a cap configured to cover said open end of said housing when said lid is in said non-inverted position, as well as when said lid is in said inverted position.

5. Apparatus according to claim 4, wherein said flange of said cage is attached to said cap of said lid, whereby said cage is invertible together with said lid.

6. Apparatus according to claim 5, wherein said flange of said cage is releasably attached to said cap of said lid, whereby said scent-diffusing cartridge is removable from said cage when said lid is not in said non-inverted position.

7. Apparatus according to claim 6, wherein said flange of said cage defines an opening configured to permit the removal of said scent-diffusing cartridge from said cage when said lid is not in said non-inverted position.

8. Apparatus according to claim 5, wherein said scent-diffusing cartridge contains a pre-selected scent.

9. Apparatus according to claim 8, wherein said pre-selected scent is that of an essential oil.

10. Apparatus according to claim 8, wherein said pre-selected scent is selected for its ability to attract game.

11. Apparatus according to claim 8, wherein said pre-selected scent is selected for its ability to calm pet animals.

12. Apparatus according to claim 8, wherein said pre-selected scent is selected for its ability to aid medical diagnostics of a patient.

13. Apparatus according to claim 8, wherein said pre-selected scent is selected for its aroma therapy capabilities.

14. Apparatus according to claim 8, wherein said pre-selected scent is selected for its ability to function as a diet aid.

15. Apparatus according to claim 8, wherein said pre-selected scent is selected for its aroma therapy capabilities.

16. Apparatus for diffusing scent, comprising a housing having an open end, a closed end opposite said open end, and an interior chamber between said open and closed ends of said housing; a replaceable, sent-diffusing cartridge positionable within said interior chamber of said housing, said scent-diffusing cartridge being adapted for non-active, dry air scent diffusion in which scent molecules can be passively emitted in non-droplet form; an invertible lid adapted for selective and sequential attachment to said open end and/or said closed end of said housing such that said scent-dispensing cartridge can be selectively isolated from and exposed to an exterior environment surrounding said apparatus, wherein said scent-diffusing cartridge is isolated from the exterior environment when said lid is in a non-inverted position and attached to said open end of said housing, and wherein said scent-diffusing cartridge is exposed to the exterior environment when said lid is in an inverted position and attached to one of said open and closed ends of said housing; and a diffuser forming a detachable portion of a compartment configured to removably receive said scent-diffusing cartridge, said diffuser having at least one surface substantially coextensive with said scent-diffusing cartridge, said at least one surface being provided with a plurality of apertures configured to allow the transmission of scent molecules therethrough to the external environment in a multi-directional configuration when said lid is in said inverted positon, and said diffuser being detachable from said compartment when said lid is in said inverted position to thereby permit access to said scent-diffusing cartridge for the unobstructed removal and/or replacement thereof.

17. Apparatus according to claims 1 or 16, wherein said lid is securely attached to said open end of said housing when said lid is in said non-inverted position.

18. Apparatus according to claim 17, wherein said lid and said housing are attached to each other in an airtight manner when said lid is in said non-inverted position.

19. Apparatus according to claim 18, wherein said lid is threadably attached to said open end of said housing when said lid is in said non-inverted position.

20. Apparatus according to claim 19, wherein said housing includes external threads on said open end thereof and said lid includes internal threads configured to threadably engage said external threads of said housing, said internal and external threads cooperating to threadably attach said lid to said housing when said lid is in said non-inverted position.

21. Apparatus according to claim 19, wherein said lid is loosely attached to said open end of said housing when said lid is in said inverted position.

22. Apparatus according to claim 21, wherein said lid includes a centering ring configured to center said lid on said open end of said housing when said lid is in said inverted position.

23. Apparatus according to claim 19 wherein said lid is threadably attached to said open end of said housing when said lid is in said inverted position.

24. Apparatus according to claim 23, wherein said housing is configured to be receivable in a cupholder of a land, sea or air vehicle.

25. Apparatus according to claim 23, further comprising a gasket positioned between said lid and said open end of said housing when said lid is in said non-inverted position, said gasket being positioned and configured so as to form an airtight seal between said lid and said housing, including said interior chamber thereof, when said lid is in said non-inverted position.

26. Apparatus according to claim 23, wherein said housing includes external threads on said open end thereof and said lid includes first internal threads configured to threadably engage said external threads of said housing when said lid is in said non-inverted position, and second internal threads configured to threadably engage said external threads of said housing when said lid is in said inverted position.

27. Apparatus according to claim 26, wherein said lid includes a cap configured to cover said open end of said housing when said lid is in said non-inverted position, as well as when said lid is in said inverted position; a first annular flange extending from said cap in a first direction; and a second annular flange extending from said cap in a second direction opposite said first direction.

28. Apparatus according to claim 27, wherein said first internal threads are positioned on said first annular flange and said second internal threads are positioned on said second annular flange.

29. Apparatus according to claim 28, wherein said diffuser is in the form of a dome-shaped member having a plurality of apertures configured to allow the transmission of scent molecules therethrough.

30. Apparatus according to claim 29, wherein said lid includes a mounting ring extending from said cap in said first direction, said mounting ring attaching said lid to said diffuser, whereby said diffuser is invertible together with said lid.

31. Apparatus according to claim 30, wherein said diffuser is releasably attached to said mounting ring of said lid, whereby said scent-diffusing cartridge is removable from said compartment when said lid is not in said non-inverted position.

32. Apparatus according to claim 31, wherein said interior chamber of said housing is configured so as to store said scent-diffusing cartridge when said scent-diffusing cartridge is not received in said compartment.

33. Apparatus according to claim 31, wherein said scent-diffusing cartridge contains a pre-selected scent.

34. Apparatus according to claim 33, wherein said pre-selected scent is that of an essential oil.

35. Apparatus according to claim 33, wherein said pre-selected scent is selected for its ability to attract game.

36. Apparatus according to claim 33, wherein said pre-selected scent is selected for its ability to calm pet animals.

37. Apparatus according to claim 33, wherein said pre-selected scent is selected for its ability to aid medical diagnostics of a patient.

38. Apparatus according to claim 33, wherein said pre-selected scent is selected for its aroma therapy capabilities.

39. Apparatus according to claim 33, wherein said pre-selected scent is selected for its ability to function as a diet aid.

40. Apparatus according to claim 33, wherein said pre-selected scent is selected for its insomnia therapy capabilities.

41. Apparatus according to claims 1 or 16, wherein said scent-diffusing cartridge includes a reticulated foam composite and a thermoplastic membrane enveloping said reticulated foam composite.

42. Apparatus according to claim 41, wherein said reticulated foam composite comprises a scaffold which includes a hydrophobic core and a hydrophilic coating applied to said hydrophobic core.

43. Apparatus according to claim 42, wherein said hydrophobic core of said scaffold has a volume in a range of from about 0.1 cubic inches to about 4 cubic inches and a weight in a range of from about 150 milligrams to about 6 grams.

44. Apparatus according to claim 42, wherein said thermoplastic membrane is heat sealed around said scaffold.

45. Apparatus according to claim 42, wherein said hydrophobic core and said hydrophilic coating are made of a foam material.

46. Apparatus according to claim 45, wherein said hydrophobic core has an open cell structure including a plurality of pores defined by a plurality of surfaces.

47. The apparatus of claim 45, wherein said thermoplastic membrane comprises one or more co-polymers selected from the group consisting of HDPE; LDPE; PP and EVA.

48. Apparatus according to claim 47, wherein said one or more co-polymers comprises EVA having a VA concentration in a range of from about 3.5% to about 18.5% of said EVA.

49. Apparatus according to claim 48, wherein said EVA has a thickness in a range of from about 2 millimeters to about 6 millimeters.

50. Apparatus according to claim 47, wherein said one or more co-polymers comprises HDPE having a thickness in a range of from about 1 millimeter to about 6 millimeters.

51. Apparatus according to claim 47, wherein said one or more co-polymers comprises LDPE having a thickness in a range of from about 1 millimeter to about 6 millimeters.

52. Apparatus according to claim 41, wherein said thermoplastic membrane has an inner surface bordering said reticulated foam composite and an outer surface, opposite said inner surface.

53. Apparatus according to claim 52, further comprising liquid odorant disposed in said reticulated foam composite, said reticulated foam composite being adapted to release scent molecules emanating from said liquid odorant.

54. Apparatus according to claim 53, wherein said thermoplastic membrane is permeable to scent molecules emanating from said liquid odorant, such that scent molecules emanating from said liquid odorant and released from said reticulated foam composite are adapted to be diffused through said thermoplastic membrane; and wherein said thermoplastic membrane is impermeable to liquid emanating from said liquid odorant, such that scent molecules diffused through said thermoplastic membrane are dischargeable from said apparatus as dry, but scented, air.

55. Apparatus according to claim 54, wherein scent molecules diffused through said thermoplastic membrane create a relatively low level of residual scent on said outer surface of said thermoplastic membrane, said level of residual scent being dependent upon the evaporation rate of said liquid odorant.

56. Apparatus according to claim 55, wherein scent molecules diffused through said thermoplastic membrane create a first concentration of scent molecules adjacent said outer surface of said thermoplastic membrane, and wherein scent molecules which have not been diffused through said thermoplastic membrane create a second concentration of scent molecules adjacent said inner surface of said thermoplastic membrane, said first concentration of scent molecules being less than said second concentration of scent molecules.

57. Apparatus according to claim 55, wherein said evaporation rate of said liquid odorant is in a range of from about 5 mg per day to about 25 mg per day and said reticulated foam composite is provided with said liquid odorant in an amount in a range of from about 50 milligrams to about 12 grams.

58. Apparatus according to claim 16, wherein said lid is removably attachable to said open end of said housing when said lid is in said non-inverted position, and said lid is removably attachable to said closed end of said housing when said lid is in said inverted position, said scent-diffusing cartridge being received in said compartment within said interior chamber of said housing when said lid is in said non-inverted position and when said lid is in said inverted position.

59. The apparatus of claim 58, wherein said scent-diffusing cartridge is removable from said compartment and replaceable with another cartridge adapted to function as a scent-absorber.

60. Apparatus according to claim 58, wherein said lid is securely attached to said open end of said housing when said lid is in said non-inverted position, said lid covering said open end of said housing when said lid is in said non-inverted position.

61. Apparatus according to claim 60, wherein said lid and said housing are attached to each other in an airtight manner when said lid is in said non-inverted position.

62. Apparatus according to claim 60, wherein said lid is threadably attached to said open end of said housing when said lid is in said non-inverted position.

63. Apparatus according to claim 62, wherein said lid is securely attached to said closed end of said housing when said lid is in said inverted position.

64. Apparatus according to claim 63, wherein said lid and said housing are attached to each other in an airtight manner when said lid is in said non-inverted position.

65. Apparatus according to claim 64, wherein said lid is threadably attached to said closed end of said housing when said lid is in said inverted position.

66. Apparatus according to claim 65, wherein said housing includes first external threads on said open end thereof and second external threads on said closed end thereof; and wherein said lid includes internal threads configured to be threadably engageable, both selectively and sequentially, with said first and second external threads of said housing, said first internal threads and said external threads cooperating to threadably attach said lid to said open end of said housing when said lid is in said non-inverted position and said second internal threads and said external threads cooperating to threadably attach said lid to said closed end of said housing when said lid is in said inverted position.

67. Apparatus according to claim 58, wherein said housing has a base forming said closed end of said housing and an annular rim extending from said base into said interior chamber of said housing, said annular rim being removably attached to a vented cage and cooperating therewith to form said compartment.

68. Apparatus according to claim 67, further comprising an attachment clip coupled to said lid and/or to said base of said housing.

69. The apparatus of claim 67, wherein said lid includes knurls configured to facilitate detachment of said lid from said housing.

70. Apparatus according to claim 67, wherein said vented cage includes finger grips configured to facilitate detachment of said vented cage from said annular rim of said base.

71. The apparatus of claim 58, wherein said housing is configured to be receivable in a cupholder of a land, sea or air vehicle.

72. Apparatus according to claim 58, wherein said scent-diffusing cartridge contains a pre-selected scent.

73. Apparatus according to claim 72, wherein said pre-selected scent is that of an essential oil.

74. Apparatus according to claim 72, wherein said pre-selected scent is selected for its ability to attract game.

75. Apparatus according to claim 72, wherein said pre-selected scent is selected for its ability to calm pet animals.

76. Apparatus according to claim 72, wherein said pre-selected scent is selected for its ability to aid medical diagnostics of a patient.

77. Apparatus according to claim 72, wherein said pre-selected scent is selected for its aroma therapy capabilities.

78. Apparatus according to claim 72, wherein said pre-selected scent is selected for its ability to function as a diet aid.

79. Apparatus according to claim 72, wherein said pre-selected scent is selected for its insomnia therapy capabilities.

80. Apparatus according to claim 58, wherein said scent-diffusing cartridge includes a reticulated foam composite and a thermoplastic membrane enveloping said reticulated foam composite.

81. Apparatus according to claim 80, wherein said thermoplastic membrane has an inner surface bordering said reticulated foam composite and an outer surface, opposite said inner surface.

82. Apparatus according to claim 81, further comprising liquid odorant disposed is said reticulated foam composite, said reticulated foam composite being adapted to release scent molecules emanating from said liquid odorant.

83. Apparatus according to claim 82, wherein said thermoplastic membrane is permeable to scent molecules emanating from said liquid odorant, such that scent molecules emanating from said liquid odorant and released from said reticulated foam composite are adapted to be diffused through said thermoplastic membrane; and wherein said thermoplastic membrane is impermeable to liquid emanating from said liquid odorant, such that scent molecules diffused through said thermoplastic membrane are dischargeable from said apparatus as dry, but scented, air.

84. Apparatus according to claim 83, wherein scent molecules diffused through said thermoplastic membrane create a relatively low level of residual scent on said outer surface of said thermoplastic membrane, said level of residual scent being dependent upon the evaporation rate of said liquid odorant.

85. Apparatus according to claim 84, wherein scent molecules diffused through said thermoplastic membrane create a first concentration of scent molecules adjacent said outer surface of said thermoplastic membrane, and wherein scent molecules which have not been diffused through said thermoplastic membrane create a second concentration of scent molecules adjacent said inner surface of said thermoplastic membrane, said first concentration of scent molecules being less than said second concentration of scent molecules.

86. Apparatus according to claim 84, wherein said evaporation rate of said liquid odorant is in a range of from about 5 mg per day to about 25 mg per day and said reticulate foam composite is provided with said liquid odorant in an amount in a range of from about 50 milligrams to about 12 grams.

87. Apparatus according to claim 80, wherein said reticulated foam composite comprises a scaffold which includes a hydrophobic core and a hydrophilic coating applied to said hydrophobic core.

88. Apparatus according to claim 87, wherein said thermoplastic membrane is heat sealed around said scaffold.

89. Apparatus according to claim 87, wherein said hydrophobic core of said scaffold has a volume in a range of from about 0.1 cubic inches to about 4 cubic inches and a weight in a range of from about 150 milligrams to about 6 grams.

90. Apparatus according to claim 87, wherein said hydrophobic core and said hydrophilic coating are made of a foam material.

91. Apparatus according to claim 90, wherein said hydrophobic core has an open cell structure including a plurality of pores defined by a plurality of surfaces.

92. The apparatus of claim 90, wherein said thermoplastic membrane comprises one or more co-polymers selected from the group consisting of HDPE; LDPE; PP and EVA.

93. Apparatus according to claim 92, wherein said one or more co-polymers comprises EVA having a VA concentration in a range of from about 3.5% to about 18.5% of said EVA.

94. Apparatus according to claim 93, wherein said EVA has a thickness in a range of from about 2 millimeters to about 6 millimeters.

95. Apparatus according to claim 92, wherein said one or more co-polymers comprises HDPE having a thickness in a range of from abut 1 millimeter to about 6 millimeters.

96. Apparatus according to claim 92, wherein said one or more co-polymers comprises LDPE having a thickness in a range of from about 1 millimeter to about 6 millimeters.

97. Apparatus for diffusing scent, comprising a housing having an open end, a closed end opposite said open end, and an interior chamber between said open and closed ends of said housing; a replaceable, scent-diffusing cartridge positionable within said interior chamber of said hosing, said scent-diffusing cartridge being adapted for non-active, dry air scent diffusion in which scent molecules can be passively emitted in non-droplet form; an invertible lid adapted for selective and sequential attachment to said open end and/or said closed end of said housing such that said scent-diffusing cartridge can be selectively isolated from and exposed to an exterior environment surrounding said apparatus, wherein said scent-diffusing cartridge is isolated from the exterior environment when said lid is in a non-inverted position and attached to said open end of said housing, and wherein said scent diffusing cartridge is exposed to the exterior environment when said lid is in an inverted position and attached to one of said open and closed ends of said housing; and a diffuser forming a portion of a compartment configured to removably receive said scent-diffusing cartridge, said diffuser configured to allow the transmission of scent molecules therethrough to the external environment when said lid is in said inverted position, and said diffuser being detachable from said apparatus when said lid is in said inverted position to thereby permit access to said scent-diffusing cartridge for removal and/or replacement thereof, wherein said scent-diffusing cartridge includes a reticulated foam composite and a thermoplastic membrane enveloping said reticulated foam composite, said reticulated foam composite comprising a scaffold including a hydrophobic core and a hydrophilic coating applied to said hydrophobic core, and wherein said thermoplastic membrane is heat sealed around said scaffold.

98. Apparatus according to claim 97, wherein said hydrophobic core and said hydrophilic coating are made of a foam material.

99. Apparatus according to claim 98, wherein said hydrophobic core has an open cell structure including a plurality of pores defined by a plurality of surfaces.

100. Apparatus for diffusing scent, comprising a housing having an open end, a closed end opposite said open end, and an interior chamber between said open and closed ends of said housing; a replaceable, scent-diffusing cartridge positionable within said interior chamber of said housing, said scent-diffusing cartridge being adapted for non-active, dry air scent diffusion in which scent molecules can be passively emitted in non-droplet form; and invertible lid adapted for selective and sequential attachment to said open end and/or said closed end of said housing such that said scent-diffusing cartridge can be selectively isolated from and exposed to an exterior environment surrounding said apparatus, wherein said scent-diffusing cartridge is isolated from the exterior environment when said lid is in a non-inverted position and attached to said open end of said housing, and wherein said scent diffusing cartridge is exposed to the exterior environment when said lid is in an inverted position and attached to one of said open and closed ends of said housing; and a diffuser forming a portion of a compartment configured to removably receive said scent-diffusing cartridge, said diffuser configured to allow the transmission of scent molecules therethrough to the external environment when said lid is in said inverted position, and said diffuser being detachable from said apparatus when said lid in in said inverted position to thereby permit access to said scent-diffusing cartridge for removal and/or replacement thereof, wherein said scent-diffusing cartridge includes a reticulated foam composite and a thermoplastic membrane enveloping said reticulated foam composite, said reticulated foam composite comprising a scaffold including a hydrophobic core and a hydrophilic coating applied to said hydrophobic core; wherein said hydrophobic core and said hydrophilic coating are made of a foam material, and wherein said thermoplastic membrane comprises one or more co-polymers selected from the group consisting of HDPE; LDPE; PP and EVA.

101. Apparatus according to claim 100, wherein said one or more co-polymers comprises EVA having a VA concentration in a range of from about 3.5% to about 18.5% of said EVA.

102. Apparatus according to claim 101, wherein said EVA has a thickness in a range of from about 2 millimeters to about 6 millimeters.

103. Apparatus according to claim 100, wherein said one or more co-polymers comprises HDPE having a thickness in a range of from about 1 millimeter to about 6 millimeters.

104. Apparatus according to claim 100, wherein said one or more co-polymers comprises LDPE having a thickness in a range of from about 1 millimeter to about 6 millimeters.

105. Apparatus for diffusing scent, comprising a housing having an open end, a closed end opposite said open end, and an interior chamber between said open and closed ends of said housing; a replaceable, scent-diffusing cartridge positionable within said interior chamber of said housing, said scent-diffusing cartridge being adapter for non-active, dry air scent diffusion in which scent molecules can be passively emitted in non-droplet form; an invertible lid adapted for selective and sequential attachment to said open end and/or said closed end of said housing such that said scent-diffusing cartridge can be selectively isolated from and exposed to an exterior environment surrounding said apparatus, wherein said scent-diffusing cartridge is isolated from the exterior environment when said lid is in a non-inverted position and attached to said open end of said housing, and wherein said scent diffusing cartridge is exposed to the exterior environment when said lid is in an inverted position and attached to one of said open and closed ends of said housing; and a diffuser forming a portion of a compartment configured to removably receive said scent-diffusing cartridge, said diffuser configured to allow the transmission of scent molecules therethrough to the external environment when said lid is in said inverted position, and said diffuser being detachable from said apparatus when said lid is in said inverted position to thereby permit access to said scent-diffusing cartridge for removal and/or replacement thereof, wherein said scent-diffusing cartridge includes a reticulated foam composite and a thermoplastic membrane enveloping said reticulated foam composite, said reticulated foam composite comprising a scaffold including a hydrophobic core and a hydrophilic coating applied to said hydrophobic core, and wherein said hydrophobic core of said scaffold has a volume in a range of from about 0.1 cubic inches to about 4 cubic inches and a weight in range of from about 150 milligrams to about 6 grams.

106. Apparatus for diffusing scent, comprising a housing having an open end, a closed end opposite said open end, and an interior chamber between said open and closed ends of said housing, scent-diffusing cartridge positionable within said interior chamber of said housing, said scent-diffusing cartridge being adapted for non-active, dry air scent diffusion in which scent molecules can be passively emitted in non-droplet form; and invertible lid adapted for selective and sequential attachment to said open end and/or said closed end of said housing such that said scent-diffusing cartridge can be selectively isolated from and exposed to an exterior environment surrounding said apparatus, wherein said scent-diffusing cartridge is isolated from the exterior environment when said lid is in a non-inverted position and attached to said open end of said housing, and wherein said scent diffusing cartridge is exposed to the exterior environment when said lid is in an inverted position and attached to one of said open and closed ends of said housing; and a diffuser forming a portion of a compartment configured to removably receive said scent-diffusing cartridge, said diffuser configured to allow the transmission of scent molecules therethrough to the external environment when said lid is in said inverted position, and said diffuser being detachable from said apparatus when said lid is in said inverted position to thereby permit access to said scent-diffusing cartridge for removal and/or replacement thereof, wherein said scent-diffusing cartridge includes a reticulated foam composite and a thermoplastic membrane enveloping said reticulated foam composite, and wherein said thermoplastic membrane has in inner surface bordering said reticulated foam composite and an outer surface, opposite said inner surface.

107. Apparatus according to claim 106, further comprising liquid odorant disposed in said reticulated foam composite, said reticulated foam composite being adapted to release scent molecules emanating from said liquid odorant.

108. Apparatus according to claim 107, wherein said thermoplastic membrane is permeable to scent molecules emanating from said liquid odorant, such that scent molecules emanating from said liquid odorant and released from said reticulated foam composite are adapted to be diffused through said thermoplastic membrane; and wherein said thermoplastic membrane is impermeable to liquid emanating from said liquid odorant, such that scent molecules diffused through said thermoplastic membrane are dischargeable from said apparatus as dry, but scented, air.

109. Apparatus according to claim 108, wherein scent molecules diffused through said thermoplastic membrane create a relatively low level of residual scent on said outer surface of said thermoplastic membrane, said level of residual scent being dependent upon the evaporation rate of said liquid odorant.

110. Apparatus according to claim 109, wherein scent molecules diffused through said thermoplastic membrane create a first concentration of scent molecules adjacent said outer surface of said thermoplastic membrane, and wherein scent molecules which have not been diffused through said thermoplastic membrane create a second concentration of scent molecules adjacent said inner surface of said thermoplastic membrane, said first concentration of scent molecules being less than said second concentration of scent molecules.

111. Apparatus according to claim 109, wherein said evaporation rate of said liquid odorant is in a range of from about 5 mg per day to about 25 mg per day and said reticulated foam composite is provided with said liquid odorant in an amount in a range of from about 50 milligrams to about 12 grams.

* * * * *

UNITED STATES PATENT AND TRADEMARK OFFICE
CERTIFICATE OF CORRECTION

| | | |
|---|---|---|
| PATENT NO. | : 12,290,618 B2 | Page 1 of 1 |
| APPLICATION NO. | : 18/634727 | |
| DATED | : May 6, 2025 | |
| INVENTOR(S) | : Corey Oliver et al. | |

It is certified that error appears in the above-identified patent and that said Letters Patent is hereby corrected as shown below:

In the Claims

Column 27, Line 11, please amend Claim 1 as follows:
-- passively emitted in non-droplet form; an invertible lid --

Column 28, Line 9, please amend Claim 15 as follows:
-- 15. Apparatus according to Claim 8, wherein said pre-selected scent is selected for its insomnia therapy capabilities. --

Column 34, Line 14, please amend Claim 100 as follows:
-- passively emitted in non-droplet form; an invertible lid --

Column 35, Line 30, please amend Claim 106 as follows:
-- non-droplet form; an invertible lid adapted for selective --

Signed and Sealed this
Thirtieth Day of September, 2025

John A. Squires
*Director of the United States Patent and Trademark Office*